United States Patent
Ferro, Jr. et al.

(10) Patent No.: US 11,367,530 B1
(45) Date of Patent: *Jun. 21, 2022

(54) HEALTH TESTING AND DIAGNOSTICS PLATFORM

(71) Applicant: EMED LABS, LLC, Miami, FL (US)

(72) Inventors: Michael W. Ferro, Jr., Palm Beach, FL (US); Sam Miller, Hollywood, FL (US); Marco Magistri, Miami, FL (US); Colman Thomas Bryant, Fort Lauderdale, FL (US); Adam Charles Carlson, Miami, FL (US); Zachary Carl Nienstedt, Wilton Manors, FL (US); Chris Ensey, Fort Lauderdale, FL (US)

(73) Assignee: EMED LABS, LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/677,606

(22) Filed: Feb. 22, 2022

Related U.S. Application Data

(63) Continuation of application No. 17/452,746, filed on Oct. 28, 2021, now Pat. No. 11,289,196, which is a
(Continued)

(51) Int. Cl.
*G16H 40/67* (2018.01)
*G06T 7/70* (2017.01)
(Continued)

(52) U.S. Cl.
CPC .......... *G16H 40/67* (2018.01); *A61B 5/7465* (2013.01); *G06F 3/0482* (2013.01);
(Continued)

(58) Field of Classification Search
CPC ........ G16H 40/67; G16H 10/40; G16H 40/20; G16H 50/20; G16H 80/00; A61B 5/7465;
(Continued)

(56) References Cited

U.S. PATENT DOCUMENTS

| 7,176,936 B2 | 2/2007 | Sauer et al. |
| 7,491,198 B2 | 2/2009 | Kockro |

(Continued)

FOREIGN PATENT DOCUMENTS

| CN | 103153248 | 6/2013 |
| CN | 105266897 | 1/2016 |

(Continued)

OTHER PUBLICATIONS

Office Action for U.S. Appl. No. 17/453,746 dated Jan. 5, 2022 in 15 pages.
(Continued)

*Primary Examiner* — Stella L. Woo
(74) *Attorney, Agent, or Firm* — Knobbe, Martens, Olson & Bear, LLP

(57) ABSTRACT

Systems and methods for providing a universal platform for at-home health testing and diagnostics are provided herein. In particular, a health testing and diagnostic platform is provided to connect medical providers with patients and to generate a unique, private testing environment. In some embodiments, the testing environment may facilitate administration of a medical test to a patient with the guidance of a proctor. In some embodiments, the patient may be provided with step-by-step instructions for test administration by the proctor within a testing environment. The platform may display unique, dynamic testing interfaces to the patient and proctor to ensure proper testing protocols and accurate test result verification.

20 Claims, 40 Drawing Sheets

Related U.S. Application Data continuation of application No. 17/452,726, filed on Oct. 28, 2021.

(60) Provisional application No. 63/179,864, filed on Apr. 26, 2021, provisional application No. 63/156,012, filed on Mar. 3, 2021, provisional application No. 63/136,575, filed on Jan. 12, 2021.

(51) Int. Cl.
| | |
|---|---|
| *G06Q 50/20* | (2012.01) |
| *G09B 19/00* | (2006.01) |
| *H04N 7/15* | (2006.01) |
| *G06F 3/0482* | (2013.01) |
| *A61B 5/00* | (2006.01) |
| *G06V 20/40* | (2022.01) |
| *H04L 65/403* | (2022.01) |
| *G16H 40/20* | (2018.01) |
| *G16H 80/00* | (2018.01) |
| *G16H 10/40* | (2018.01) |
| *G16H 50/20* | (2018.01) |
| *H04L 65/1069* | (2022.01) |

(52) U.S. Cl.
CPC ............ *G06Q 50/205* (2013.01); *G06T 7/70* (2017.01); *G06V 20/41* (2022.01); *G09B 19/003* (2013.01); *G16H 10/40* (2018.01); *G16H 40/20* (2018.01); *G16H 50/20* (2018.01); *G16H 80/00* (2018.01); *H04L 65/1069* (2013.01); *H04L 65/403* (2013.01); *H04N 7/15* (2013.01); *G06T 2207/10016* (2013.01)

(58) Field of Classification Search
CPC ....... G06F 3/0482; G06Q 50/205; G06T 7/70; G06T 2207/10016; G06V 20/41; G09B 19/003; H04L 65/1069; H04L 65/403; H04N 7/15

See application file for complete search history.

(56) References Cited

U.S. PATENT DOCUMENTS

| | | | |
|---|---|---|---|
| 7,662,113 B2 | 2/2010 | Pearl et al. | |
| 8,108,190 B2 | 1/2012 | Riener et al. | |
| 8,253,778 B2 | 8/2012 | Atsushi | |
| 8,314,815 B2 | 11/2012 | Navab et al. | |
| 8,485,038 B2 | 7/2013 | Sengupta et al. | |
| 8,611,988 B2 | 12/2013 | Miyamoto | |
| 8,713,130 B2* | 4/2014 | Logan | H04L 65/60 434/362 |
| 8,768,022 B2 | 7/2014 | Miga et al. | |
| 8,814,691 B2 | 8/2014 | Haddick et al. | |
| 8,911,358 B2 | 12/2014 | Koninckx | |
| 8,948,935 B1 | 2/2015 | Peeters et al. | |
| 8,982,156 B2 | 3/2015 | Maggiore | |
| 9,030,446 B2 | 5/2015 | Mistry et al. | |
| 9,082,319 B2 | 7/2015 | Shimada et al. | |
| 9,111,383 B2 | 8/2015 | Fein et al. | |
| 9,256,711 B2 | 2/2016 | Horseman | |
| 9,262,743 B2 | 2/2016 | Heins et al. | |
| 9,285,871 B2 | 3/2016 | Geisner et al. | |
| 9,338,622 B2 | 5/2016 | Bjontegard | |
| 9,345,957 B2 | 5/2016 | Geisner et al. | |
| 9,380,177 B1 | 6/2016 | Rao et al. | |
| 9,424,761 B2 | 8/2016 | Tuchschmid et al. | |
| 9,498,132 B2 | 11/2016 | Maier-Hein et al. | |
| 9,547,917 B2 | 1/2017 | Zamer | |
| 9,563,266 B2 | 2/2017 | Banerjee et al. | |
| 9,600,934 B2 | 3/2017 | Odessky et al. | |
| 9,606,992 B2 | 3/2017 | Geisner et al. | |
| 9,648,436 B2 | 5/2017 | Kraft | |
| 9,788,714 B2 | 10/2017 | Krueger | |
| 9,836,888 B2 | 12/2017 | Skidmore | |
| 9,877,642 B2 | 1/2018 | Duret | |
| 9,886,458 B2 | 2/2018 | Jung et al. | |
| 9,892,561 B2 | 2/2018 | Choukroun et al. | |
| 9,898,662 B2 | 2/2018 | Tsuda et al. | |
| 9,916,002 B2 | 3/2018 | Petrovskaya et al. | |
| 9,972,137 B2 | 5/2018 | Petrovskaya et al. | |
| 10,013,896 B2 | 7/2018 | Feins et al. | |
| 10,052,026 B1 | 8/2018 | Tran | |
| 10,106,172 B2 | 10/2018 | Wingfield et al. | |
| 10,108,266 B2 | 10/2018 | Banerjee et al. | |
| 10,127,734 B2 | 11/2018 | Stroila | |
| 10,156,900 B2 | 12/2018 | Publicover et al. | |
| 10,197,803 B2 | 2/2019 | Badiali et al. | |
| 10,216,957 B2 | 2/2019 | Jung et al. | |
| 10,231,614 B2 | 3/2019 | Krueger | |
| 10,295,815 B2 | 5/2019 | Romanowski et al. | |
| 10,322,313 B2 | 6/2019 | McKirdy | |
| 10,346,889 B1 | 7/2019 | Reiss et al. | |
| 10,386,918 B2 | 8/2019 | Shin | |
| 10,430,985 B2 | 10/2019 | Harrises et al. | |
| 10,474,233 B2 | 11/2019 | Swaminathan et al. | |
| 10,524,715 B2 | 1/2020 | Sahin | |
| 10,535,202 B2 | 1/2020 | Schmirler et al. | |
| 10,540,776 B2 | 1/2020 | Tran et al. | |
| 10,559,117 B2 | 2/2020 | Kaeser et al. | |
| 10,593,092 B2 | 3/2020 | Solomon | |
| 10,643,210 B2 | 5/2020 | Smith et al. | |
| 10,660,522 B2 | 5/2020 | Redei | |
| 10,664,572 B2 | 5/2020 | Bitran et al. | |
| 10,758,209 B2 | 9/2020 | Boctor et al. | |
| 10,788,791 B2 | 9/2020 | Gelman et al. | |
| 10,802,695 B2 | 10/2020 | Daniels et al. | |
| 10,824,310 B2 | 11/2020 | Acharya et al. | |
| 10,832,488 B2 | 11/2020 | Petrovskaya et al. | |
| 10,849,688 B2 | 12/2020 | Rios et al. | |
| 10,885,530 B2 | 1/2021 | Mercury et al. | |
| 10,888,389 B2 | 1/2021 | Draelos et al. | |
| 10,892,052 B2 | 1/2021 | Jordan et al. | |
| 10,910,016 B2 | 2/2021 | Rothschild et al. | |
| 10,932,705 B2 | 3/2021 | Muhsin et al. | |
| 10,943,407 B1 | 3/2021 | Morgan et al. | |
| 10,945,807 B2 | 3/2021 | Gibby et al. | |
| 10,957,111 B2 | 3/2021 | Weisman et al. | |
| 10,984,910 B2 | 4/2021 | Burkholz et al. | |
| 10,991,190 B1* | 4/2021 | Luthra | G16H 50/80 |
| 10,991,461 B2 | 4/2021 | Divine et al. | |
| 11,004,271 B2 | 5/2021 | Cvetko et al. | |
| 11,017,694 B2 | 5/2021 | Buras et al. | |
| 11,152,093 B1 | 10/2021 | Hopen, Sr. et al. | |
| 11,289,196 B1* | 3/2022 | Ferro, Jr. | G09B 19/003 |
| 2007/0048723 A1* | 3/2007 | Brewer | G09B 7/02 434/350 |
| 2009/0004055 A1 | 1/2009 | Darrigrand et al. | |
| 2009/0263775 A1 | 10/2009 | Ullrich | |
| 2010/0121156 A1 | 5/2010 | Yoo | |
| 2010/0159434 A1 | 6/2010 | Lampotang et al. | |
| 2011/0207108 A1* | 8/2011 | Dorman | G09B 9/00 434/350 |
| 2012/0053955 A1 | 3/2012 | Martin et al. | |
| 2013/0096937 A1 | 4/2013 | Campbell et al. | |
| 2013/0253339 A1* | 9/2013 | Reyes | G06Q 10/06 600/549 |
| 2013/0344470 A1* | 12/2013 | Morgan | G09B 7/00 434/350 |
| 2014/0160264 A1 | 6/2014 | Taylor et al. | |
| 2014/0253590 A1 | 9/2014 | Needham et al. | |
| 2014/0304335 A1 | 10/2014 | Fung et al. | |
| 2016/0125765 A1 | 5/2016 | Meretei et al. | |
| 2016/0292378 A1 | 10/2016 | Saric | |
| 2016/0371884 A1 | 12/2016 | Benko et al. | |
| 2017/0103440 A1 | 4/2017 | Xing et al. | |
| 2017/0115742 A1 | 4/2017 | Xing et al. | |
| 2017/0146801 A1 | 5/2017 | Stempora | |
| 2017/0173262 A1 | 6/2017 | Veltz | |
| 2017/0323062 A1 | 11/2017 | Djajadiningrat et al. | |
| 2018/0039737 A1 | 2/2018 | Dempers et al. | |
| 2018/0092595 A1 | 4/2018 | Chen et al. | |

(56) References Cited

U.S. PATENT DOCUMENTS

| | | |
|---|---|---|
| 2018/0140362 A1 | 5/2018 | Cal et al. |
| 2018/0173913 A1 | 6/2018 | Pulitzer et al. |
| 2018/0197624 A1 | 7/2018 | Robaina et al. |
| 2018/0225982 A1* | 8/2018 | Jaeh .................. G09B 5/00 |
| 2018/0253840 A1 | 9/2018 | Tran |
| 2018/0353073 A1 | 12/2018 | Boucher et al. |
| 2019/0000564 A1 | 1/2019 | Navab et al. |
| 2019/0005195 A1 | 1/2019 | Peterson |
| 2019/0020651 A1 | 1/2019 | Soon-Shiong et al. |
| 2019/0025919 A1 | 1/2019 | Tadi et al. |
| 2019/0064520 A1 | 2/2019 | Christensen |
| 2019/0073110 A1* | 3/2019 | Bradley .................. G06F 3/048 |
| 2019/0139318 A1 | 5/2019 | Tierney et al. |
| 2019/0179584 A1 | 6/2019 | Masters |
| 2019/0206134 A1 | 7/2019 | Devam et al. |
| 2019/0216452 A1 | 7/2019 | Nawana et al. |
| 2019/0259483 A1 | 8/2019 | Potts |
| 2019/0261914 A1 | 8/2019 | Davis et al. |
| 2019/0266663 A1 | 8/2019 | Keeler et al. |
| 2019/0378080 A1 | 12/2019 | Srinivasan et al. |
| 2019/0380790 A1 | 12/2019 | Fuchs et al. |
| 2019/0391638 A1 | 12/2019 | Khaderi et al. |
| 2020/0000401 A1 | 1/2020 | Dullen |
| 2020/0020171 A1 | 1/2020 | Hendricks et al. |
| 2020/0073143 A1 | 3/2020 | Macnamara et al. |
| 2020/0101367 A1 | 4/2020 | Tran et al. |
| 2020/0152339 A1 | 5/2020 | Pulitzer et al. |
| 2020/0207501 A1 | 7/2020 | Urquhart et al. |
| 2020/0211291 A1 | 7/2020 | Miller et al. |
| 2020/0226758 A1 | 7/2020 | Carnes et al. |
| 2020/0250389 A1 | 8/2020 | Pulitzer et al. |
| 2020/0303044 A1* | 9/2020 | Stephen ............... G06K 7/1417 |
| 2020/0312038 A1 | 10/2020 | Samec et al. |
| 2020/0337631 A1 | 10/2020 | Sahin |
| 2020/0342679 A1 | 10/2020 | Soon-Shiong |
| 2020/0405257 A1 | 12/2020 | Samec et al. |
| 2020/0409159 A1 | 12/2020 | Samec et al. |
| 2021/0022810 A1 | 1/2021 | Mahfouz |
| 2021/0058485 A1 | 2/2021 | Devam et al. |
| 2021/0086989 A1 | 3/2021 | Luxford |
| 2021/0183507 A1 | 6/2021 | Shaya |
| 2021/0326474 A1* | 10/2021 | Sparks .................. G16H 10/60 |
| 2021/0350883 A1* | 11/2021 | Li .......................... G16H 50/20 |
| 2021/0358068 A1 | 11/2021 | Boszczyk et al. |
| 2022/0020236 A1 | 1/2022 | Luthra et al. |

FOREIGN PATENT DOCUMENTS

| | | |
|---|---|---|
| KR | 10-2008-0012745 | 2/2008 |
| KR | 10-2018-0068703 | 6/2018 |
| WO | WO 2021/044064 A1 | 3/2021 |
| WO | WO 2021/171226 A2 | 9/2021 |

OTHER PUBLICATIONS

International search report and Written opinion for PCT Application No. PCT/US2021/057116 dated Feb. 21, 2022 in 9 pages.

Uber expands options for prescription delivery with ScriptDrop, Mar. 24, 2021, Uber.com Blog (Year: 2021).

Office Action for U.S. Appl. No. 17/452,966 dated Feb. 18, 2022 in 42 pages.

Baruah, Basant, "Augmented reality and QR codes—What you need to know", accessed via wayback machine for Apr. 14, 2021, beaconstac blog.

Zheng, Lixia, "Using Augmented Reality with Interactive Narrative to Help Paediatric Patients Take Prescription Medication", 2020, University College London.

* cited by examiner

FIG. 8

Please confirm the following

Are you free for the next 20 minutes?

○ Yes
○ No

Do you have your test available?

○ Yes
○ No

Is your test in an unopened package?

○ Yes
○ No

What is your date of birth?

[ DD / MM / YYYY ]

SUBMIT

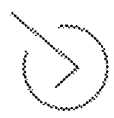
FIG. 9

FIG. 10

Join test session

Please enter your 6-digit meeting code below.

Meeting code

[Enter your meeting code]

SUBMIT CODE

DON'T HAVE A CODE? CLICK HERE

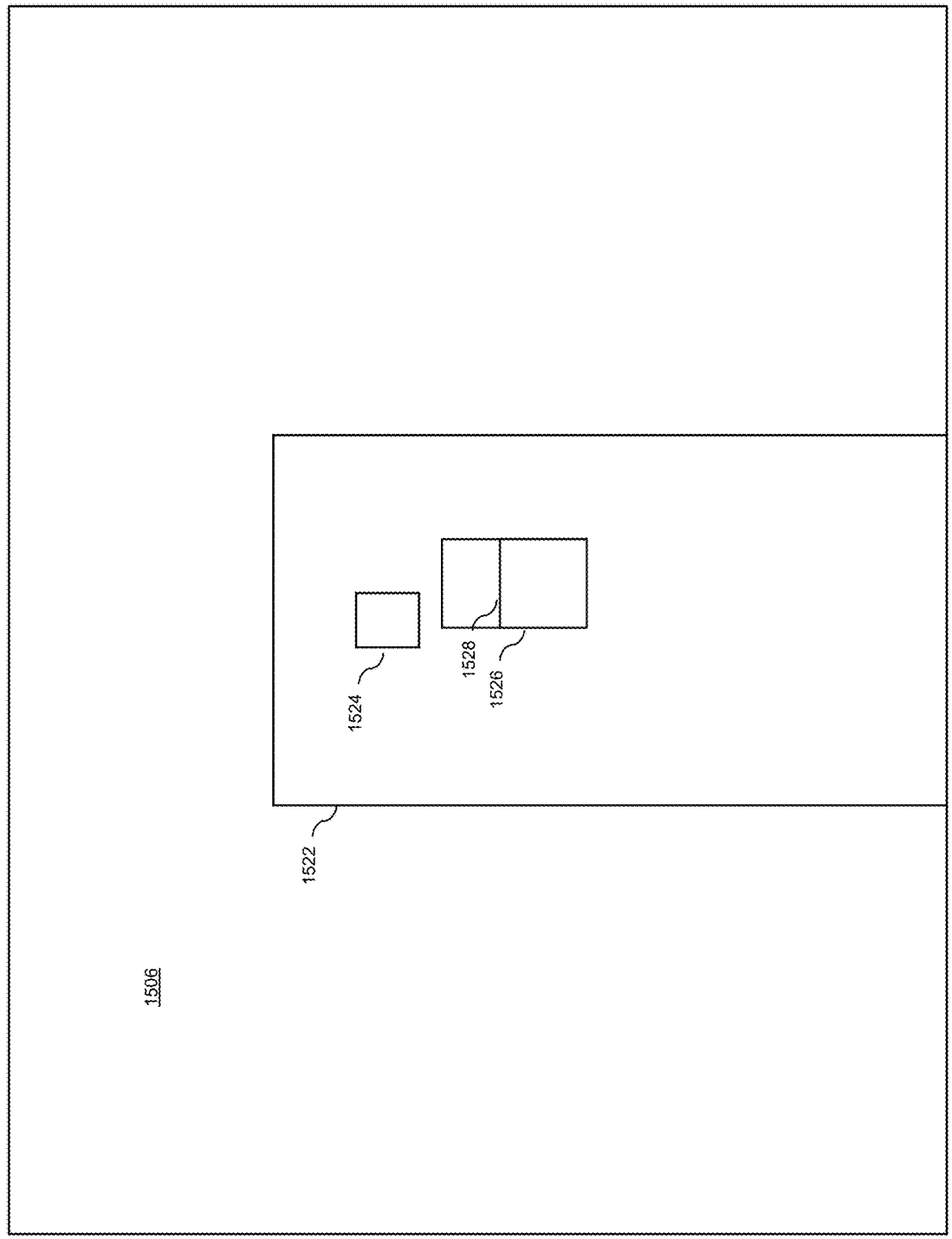

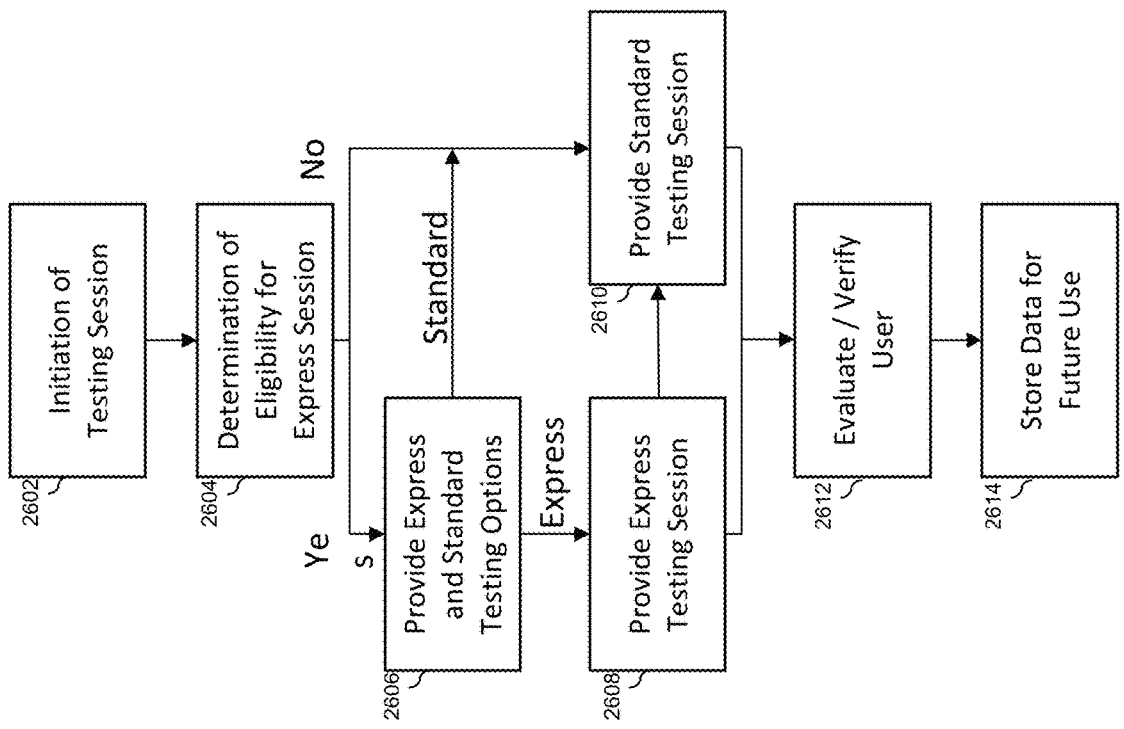

HEALTH TESTING AND DIAGNOSTICS PLATFORM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. application Ser. No. 17/452,746, entitled "HEALTH TESTING AND DIAGNOSTICS PLATFORM," filed Oct. 28, 2021, which is a continuation of U.S. application Ser. No. 17/452,726, entitled "HEALTH TESTING AND DIAGNOSTICS PLATFORM," filed Oct. 28, 2021, which claims the benefit under 35 U.S.C. 119(e) to U.S. Provisional Application No. 63/136,575, entitled "HEALTH TESTING AND DIAGNOSTICS PLATFORM," filed Jan. 12, 2021, to U.S. Provisional Application No. 63/156,012, entitled "HEALTH TESTING AND DIAGNOSTICS PLATFORM," filed Mar. 3, 2021, and to U.S. Provisional Application 63/179,864, entitled "HEALTH TESTING AND DIAGNOSTICS PLATFORM," filed Apr. 26, 2021, each of which is hereby incorporated by reference herein.

BACKGROUND

Field

Some embodiments of the present disclosure are directed to systems and methods for conducting remote health testing and diagnostics.

Description

Use of telehealth to deliver health care services has grown consistently over the last several decades, and has exploded in usage during the Coronavirus disease 2019 (COVID-19) Public Health Emergency (PHE). Telehealth is the distribution of health-related services and information via electronic information and telecommunication technologies. Telehealth allows long-distance patient and health provider contact, care, advice, reminders, education, intervention, monitoring, and remote admissions. In situations such as the COVID-19 PHE, when many medical and hospital resources are devoted to treating the sick, patients are more reluctant to travel to their health provider in-person, and when access to care is restricted, telehealth provides an invaluable resource.

During the COVID-19 pandemic, testing for coronavirus disease (COVID-19) was extremely limited in various places throughout the world, including the United States. Tracing infected individuals was and continues to be an important step in preventing new cases of infectious diseases. In response, the United States Food and Drug Administration (FDA) has authorized various at-home COVID-19 tests.

At-home testing solves some of the problems with in-person testing. For example, health insurance may not be required, travel to a testing site is avoided, and tests can be completed at a patient's convenience. However, at-home testing introduces various additional logistical and technical issues, such as guaranteeing timely test delivery to a patient's home, providing test delivery from a patient to an appropriate lab, ensuring test verification and integrity, providing test result reporting to appropriate authorities and medical providers, and connecting patients with medical providers, who are needed to provide guidance and/or oversight of the testing procedures remotely. These issues are not unique to COVID-19 and will need to be addressed in relation to remote health diagnostic testing generally. Therefore, a novel health and diagnostic platform, which solves the issues associated with at-home health testing, is needed.

SUMMARY

For purposes of this summary, certain aspects, advantages, and novel features of the invention are described herein. It is to be understood that not all such advantages necessarily may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

Health testing and diagnostics platforms are provided herein that can facilitate proctored at-home testing. Users performing at home testing may be guided or assisted by proctors that are available over a communication network. The platform can be optimized such that proctors can supervise the at-home tests of a plurality of users. In some embodiments, users that have gained experience and proficiency with the platform and the at-home tests may be eligible for expedited or express proctoring sessions. Such platforms can, for example, greatly increase the availability of testing, and reduce the spread of infectious diseases, and increase the efficiency of proctors in terms of increasing the number of patients that a proctor can simultaneously monitor.

In a first aspect, a computer-implemented system for a proctored examination platform for a medical diagnostic test is described. The computer-implemented system comprises an electronic storage comprising computer-executable instructions and one or more processors in electronic communication with the electronic storage medium and configured to execute the computer-executable instructions in order to: receive, by the computing system from a user device of a user in communication with the computing system over an electronic network, a request for a proctored examination session for a medical diagnostic test; based on the request, establish, by the computing system, the proctored examination session between the user device of the user and a proctor device of a proctor over the electronic network; receive, by the computing system, image data from at least one imaging device of the user device, the image data comprising at least a view of the user or at least one testing material of a test kit for the medical diagnostic test; identify, by the computing system, at least one feature within the image data received from the imaging device of the user device, the at least one feature comprising at least one of an anatomical feature of the user or at least one testing feature of the at least one testing material of the test kit; generate, by the computing system, user display data for display to the user on a user graphical user interface on a display of the user device, the user display data comprising at least: the image data received from the at least one imaging device of the user device, and at least one computer-generated graphic associated with the identified at least one feature within the image data, wherein the at least one computer-generated graphic is overlaid onto the image data at a position associated with at least one identified feature, and the at least one computer-generated graphic is configured to facilitate at least one step of the medical diagnostic test; generate, by the computing system, proctor display data for display to the proctor on a proctor graphical user interface on a display of the proctor device, the proctor display data comprising at least the image data received from the imaging device of the user device and information associated with the medical diagnostic test; transmit, from the computing system over the electronic network, the user display data to the user device for display on the user graphical user interface on the display of the user device; and transmit, from the computing system, the proctor display data to the proctor device for display on the proctor graphical user interface on the display of the proctor device; whereby the user performs the at least one step of the medical diagnostic test based on the user display data and the proctor monitors performance of the at least one step of the medical diagnostic test based on the proctor display data.

The system can include one or more of the following features in any combination: (a) wherein the proctor display data further comprises the at least one computer-generated graphic associated with the identified at least one feature within the image data, wherein the at least one computer-generated graphic is overlaid onto the image data at a position associated with at least one identified feature, and the at least one computer-generated graphic configured to facilitate at least one step of the medical diagnostic test; (b) wherein identifying the at least one feature within the image data received from the imaging device of the user device comprises analyzing, by the computing system, the image data using a computer vision algorithm configured to detect the at least one feature within the image data; (c) wherein transmitting the user display data to the user device and transmitting the proctor display data to the proctor device occur substantially simultaneously such that the user and the proctor view the image data in a substantially synchronized state; (d) wherein the at least one feature within the image data comprises a nostril of the user; (e) wherein the at least one feature within the image data comprises a test swab; (f) wherein the at least one feature within the image data comprises a portion of a testing material to which a testing solution is to be introduced by the user; (g) wherein the information associated with the medical diagnostic test of the proctor display data comprises an indication of a current testing step of the medical diagnostic test; (h) wherein the information associated with the medical diagnostic test of the proctor display data comprises a testing instruction to be read to the user by the proctor; (i) wherein the proctored testing session comprises an electronic video conference session between the user device and proctor device; (j) wherein the user comprises a first user, the image data comprises first image data, and the computer-implemented system is further configured to receive, by the computing system from a second user device of a second user in communication with the computing system over the electronic network, a second request for a second proctored examination session for a second medical diagnostic test; based on the second request for the second proctored examination session for the second medical diagnostic test, establish the second proctored examination session between the second user device of the second user and the proctor device of the proctor over the electronic network; receive, at the computing system, second image data from at least one second imaging device of the second user device, the second image data comprising at least a second view of the second user or at least one second testing material of a second test kit of the second medical diagnostic test; identify, by the computing system, at least one second feature within the second image data received from the second imaging device of the second user device, the at least one second feature comprising at least one of an anatomical feature of the second user or at least one testing feature of the at least one second testing material of the second test kit; generate, by the computing system, second user display data for display to the second user on a second user graphical user interface on a second display of the second user device, the second user display data comprising at least: the second image data received from the at least one second imaging device of the second user device, and at least one second computer-generated graphic associated with the identified at least one second feature within the second image data, wherein the at least one second computer-generated graphic is overlaid onto the second image data at a position associated with at least one identified second feature, and the at least one second computer-generated graphic is configured to facilitate at least one step of the second medical diagnostic test; generate, by the computing system, second proctor display data for display to the proctor on the proctor graphical user interface on the display of the proctor device, the second proctor display data comprising at least the second image data received from the imaging device of the second user device and second information associated with the second medical diagnostic test; transmit, from the computing system over the electronic network, the second user display data to the second user device for display on the second user graphical user interface on the display of the second user device; and transmit, from the computing system, the second proctor display data to the proctor device for display on the proctor graphical user interface on the display of the proctor device; whereby the second user performs the at least one step of the medical diagnostic test aided by the second user display data and the proctor monitors performance of the at least one step of the second medical diagnostic test aided by the second proctor display data; (k) wherein the proctor graphical user interface is configured to display the first proctor display data and the second proctor display data at the same time such that the proctor monitors the first user and the second user at the same time; and/or other features as described throughout this application.

In another aspect, a computer-implemented system for a multi-session proctored examination platform for a medical diagnostic test is described. The computer-implemented system comprises: an electronic storage medium of a computing system, the electronic storage medium comprising computer-executable instructions; one or more processors of the computing system, the one or more processors in electronic communication with the electronic storage medium, the one or more processors in electronic communication through an electronic network with a first user computing device and a second user computing device, the one or more processors configured to execute the computer-executable instructions stored in the electronic storage medium for implementing the multi-session proctored examination platform for the medical diagnostic test by: receiving, by the computing system, through the electronic network a first user request from a first user for a proctored examination at a first time, the first user request received from the first user computing device; generating, by the computing system, display data for displaying a graphical user interface (GUI) on a display of a proctor device, the display data configured to display to a proctor a first set of two or more phases of the medical diagnostic test and a first phase indicator showing a current phase of the first user in the two or more phases of the medical diagnostic test; transmitting, by the computing system, through the electronic network the display data to the proctor device; receiving, by the computing system, through the electronic network a first video conference connection request from the proctor device; establishing, by the computing system, a first electronic video conference session between the proctor device and the first user computing device; receiving, by the computing system, through the electronic network a second user request from a second user for a proctored examination at a second time, the second user request received from the second user computing device, wherein the second time is later in time than the first time; generating, by the computing system, supplemental display data for displaying the graphical user interface (GUI) on the display of the proctor device, the supplemental display data configured to concurrently display: the first set of two or more phases of the medical diagnostic test and a second phase indicator showing the current phase of the first user in the first set of two or more phases of the medical diagnostic test, and a second set of two or more phases of the medical diagnostic test and a third phase indicator showing the current phase of the second user in the second set of two or more phases of the medical diagnostic test, wherein the second and third phase indicators are at different phases in the two or more phases of the medical diagnostic test; transmitting, by the computing system, through the electronic network the supplemental display data to the proctor device; receiving, by the computing system, through the electronic network a first video conference connection termination request and a second video conference connection request from the proctor device; terminating, by the computing system, the first electronic video conference session between the proctor device and the first user computing device; transmitting, by the computing system, through the electronic network to the first user computing device content data configured to be displayed on the first user computing device; and establishing, by the computing system, a second electronic video conference session between the proctor device and the second user computing device.

The system may include one or more of the following features in any combination: (a) wherein the content data comprises augmented reality content data for showing the first user how to administer the medical diagnostic test; (b) wherein the content data comprises virtual reality content data for showing the first user how to administer the medical diagnostic test; (c) the proctor can simultaneously conduct the second video conference session with the second user while monitoring the first user that is viewing the content data; (d) wherein the monitoring the first user that is viewing the content data comprises transmitting, by the computer system, through the electronic network to the proctor device video data of the first user to ensure that the first user is watching the content data; (e) analyzing, by the computing system, using a computer vision algorithm the video data to detect a medical diagnostic test device and to determine if the medical diagnostic test device has moved, and transmitting, by the computing system, through the electronic network, based on determining that the medical diagnostic test device has moved, an alert notification to the proctor device to notify the proctor that the medical diagnostic test device has moved; (f) receiving, by the computing system, through the electronic network a mute request from the proctor device to mute the proctor for the second electronic video conference session, and an unmute request from the proctor device to unmute the proctor associated with the video data being transmitted to the first user; (g) wherein the third phase indicator is in an earlier phase relative to the second phase indicator; (h) the computing system comprises one or more computing systems; (i) wherein the supplemental display data configured to concurrently display the first set of two or more phases of the medical diagnostic test and the second set of two or more phases of the medical diagnostic test enables the proctor to monitor multiple medical diagnostic test sessions for multiple users; and/or other features as described throughout this application.

In another aspect, a computer-implemented method for a multi-session proctored examination platform for one or more medical diagnostic tests, the computer-implemented is described. The method comprises: receiving, by the computing system, through an electronic network a first user request from a first user for a proctored examination at a first time, the first user request received from a first user computing device; generating, by the computing system, display data for displaying a graphical user interface (GUI) on a display of a proctor device, the display data configured to display to a proctor a first set of two or more phases of a first medical diagnostic test and a first phase indicator showing a current phase of the first user in the two or more phases of the first medical diagnostic test; transmitting, by the computing system, through the electronic network the display data to the proctor device; receiving, by the computing system, through the electronic network a first video conference connection request from the proctor device; establishing, by the computing system, a first electronic video conference session between the proctor device and the first user computing device; receiving, by the computing system, through the electronic network a second user request from a second user for a proctored examination at a second time, the second user request received from a second user computing device, wherein the second time is later in time than the first time; generating, by the computing system, supplemental display data for displaying the graphical user interface (GUI) on the display of the proctor device, the supplemental display data configured to concurrently display: the first set of two or more phases of the first medical diagnostic test and a second phase indicator showing the current phase of the first user in the first set of two or more phases of the first medical diagnostic test, and a second set of two or more phases of a second medical diagnostic test and a third phase indicator showing the current phase of the second user in the second set of two or more phases of the second medical diagnostic test, wherein the second and third phase indicators are at different phases in the two or more phases of the first and second medical diagnostic tests; transmitting, by the computing system, through the electronic network the supplemental display data to the proctor device; receiving, by the computing system, through the electronic network a second video conference connection request from the proctor device; terminating, by the computing system, a video feed from the proctor device in the first electronic video conference session between the proctor device and the first user computing device; and establishing, by the computing system, a second electronic video conference session between the proctor device and the second user computing device, wherein the computing system comprises one or more computer processors and an electronic memory.

The system may include one or more of the following features in any combination: (a) transmitting, by the computing system, through the electronic network to the first user computing device a content data comprising augmented reality content data for showing the first user how to administer the first medical diagnostic test; (b) transmitting, by the computing system, through the electronic network to the first user computing device a content data comprises virtual reality content data for showing the first user how to administer the first medical diagnostic test; (c) wherein the proctor can simultaneously conduct the second video conference session with the second user while monitoring the first user through the first electronic video conference session; (d) wherein the monitoring the first user comprises transmitting, by the computer system, through the electronic network to the proctor device video data of the first user to ensure that the first user is present during the first medical diagnostic test; (e) analyzing, by the computing system, using a computer vision algorithm the video data to detect a medical diagnostic test device and to determine if the medical diagnostic test device has moved, and transmitting, by the computing system, through the electronic network, based on determining that the medical diagnostic test device has moved, an alert notification to the proctor device to notify the proctor that the medical diagnostic test device has moved; (f) receiving, by the computing system, through the electronic network a mute request from the proctor device to mute the proctor for the second electronic video conference session, and an unmute request from the proctor device to unmute the proctor for the first electronic video conference session; (g) wherein the third phase indicator is in an earlier phase relative to the second phase indicator; (h) wherein the computing system comprises one or more computing systems; (i) wherein the supplemental display data configured to concurrently display the first set of two or more phases of the first medical diagnostic test and the second set of two or more phases of the second medical diagnostic test enables the proctor to monitor multiple medical diagnostic test sessions for multiple users; and/or other features as described throughout this application.

BRIEF DESCRIPTION OF THE DRAWINGS

The drawings are provided to illustrate example embodiments and are not intended to limit the scope of the disclosure. A better understanding of the systems and methods described herein will be appreciated upon reference to the following description in conjunction with the accompanying drawings, wherein:

FIG. 8 illustrates an example pre-testing confirmation interface according to some embodiments described herein.

FIG. 9 illustrates an example pre-testing virtual waiting room according to some embodiments described herein.

FIG. 10 illustrates an example unique code submission interface according to some embodiments described herein.

FIG. 15B illustrates another example testing interface according to some embodiments described herein.

FIG. 19 illustrates an example testing summary interface according to some embodiments described herein.

FIG. 20 illustrates an example test distribution interface according to some embodiments described herein.

FIG. 22 illustrates an example testing dashboard interface according to some embodiments described herein.

FIG. 26 illustrates an example flowchart for providing standard testing sessions and/or express testing sessions according to some embodiments described herein.

DETAILED DESCRIPTION

Figure 1:
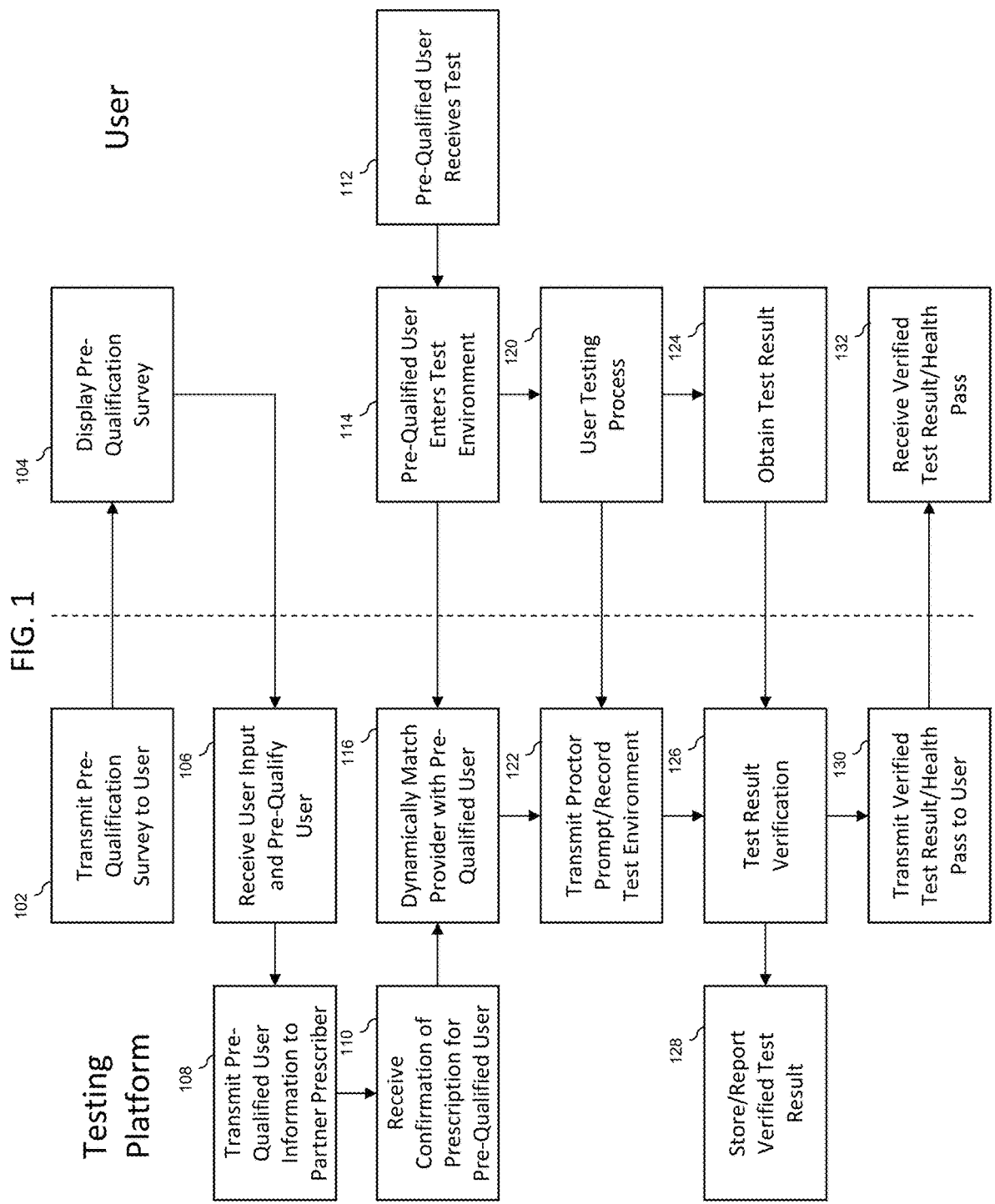
FIG. 1 illustrates an example flowchart of an at-home testing protocol according to some embodiments described herein.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present technology.

Some embodiments herein are directed to a health testing and diagnostics platform for facilitating remote health testing via remote connection of patients and medical providers. At-home medical testing provides various benefits over in-person visits to medical professionals. For example, at-home medical testing provides both safety and convenience to patients and medical providers. In-person visits by individuals with infectious diseases endangers both medical professionals, as well as anyone who encounters the individuals on their way to the in-person visit. At-home testing does not involve personal contact between the patient and any other individuals who may otherwise be at risk. Furthermore, at-home testing is simply more convenient, as neither medical providers nor patients need to leave the safety or comfort of their home in order to administer a test using remote testing platforms.

Additionally, because of advancements in medical and logistics technology, especially as described herein, at-home testing can now be extremely fast. In some cases, diagnostic tests can be administered and read within seconds. Other tests may require a cure time before being read or may require delivery to a laboratory to receive results, but results can still be received within days in most cases.

Applications for at-home medical testing are abundant. For example, at-home testing can be used by travelers in any location to ensure that the traveler is healthy before and/or after arriving at a destination, without having to locate medical care in an unfamiliar locale. Furthermore, at-home testing may prevent the spread of infectious diseases by providing travelers knowledge of when to quarantine or avoid traveling altogether, and to avoid bringing home an infectious disease. At-home testing may also be useful for sensitive individuals such as the elderly and children. At-home testing may provide a better experience for such sensitive individuals, especially in cases in which the testing procedure is uncomfortable or invasive. At-home testing can mean that the test is done in a safe, comfortable, and familiar environment, so sensitive individuals may feel less stressed and worried during their test, allowing testing to proceed more smoothly. In some instances, at-home testing can be performed in a user's home, although this need not be the case in all instances. For example, as used herein, at-home testing can refer to testing performed in other locations outside the home, such as in hotel rooms, airports, or other remote locations where access to an in-person healthcare provider is not available or desirable. Another consideration for at-home testing is privacy. At-home testing can be private and discreet, which is ideal for high-profile individuals or sensitive individuals who want to get tested without leaving their homes. Also, accessibility considerations favor at-home testing. At-home testing is ideal for anyone who has transportation issues or mobility/accessibility considerations.

Considering the advantages of at-home testing, systems and methods for providing a universal platform for at-home health testing and diagnostics are provided herein. In particular, a health testing and diagnostic platform is provided to connect medical providers (such as remotely located medical providers) with patients and to generate a unique, private testing environment. In some embodiments, the testing environment may facilitate administration of a medical test to a patient with the guidance of a proctor. In some embodiments, the proctor may comprise uncertified personnel, certified medical personnel, and/or a proctor for monitoring an algorithm such as computer software, which may administer a medical test. In some embodiments, the computer software is not administering the medical test but rather is monitoring the medical test for abnormalities or deviations or inconsistencies in the administration or performance or procedure of the medical test that is being administered by the uncertified personnel and/or certified medical personnel and/or medical personnel and/or the like. In some embodiments, the patient may be provided with step-by-step instructions for test administration by the proctor within a testing environment. The platform may display unique, dynamic testing interfaces to the patient and proctor to ensure proper testing protocols and/or accurate test result verification.

In some embodiments, the platform may provide mechanisms for user registration and medical test ordering and fulfillment. In some embodiments, the platform may be connected to one or more pharmacies or third-party providers that may approve and fulfill test kit orders. In some embodiments, the platform may provide a testing environment comprising a private communication channel (such as over the internet) between a proctor and a patient. In some embodiments, the testing environment may comprise one or more unique user interfaces that may facilitate seamless testing, submission and verification. In some embodiments, the platform may provide for automatic transmission of verified test results to users, relevant authorities, and third parties. In some embodiments, the platform may generate a unique health card or passport, which may provide an easily accessible and understandable testing summary for a patient and/or third parties.

In some embodiments, the platform may be configured to register, train, and certify medical providers to proctor diagnostic tests using the platform. In some embodiments, proctors may be enabled to initiate testing sessions via a virtual waiting room and interpret test results using tools provided by the one or more unique user interfaces of the platform. In some embodiments, proctors may be enabled to manage more than one test session concurrently via unique multi-session user interfaces generated by the platform, which assist with management and administration of multiple concurrent test sessions.

In some embodiments, the platform may also be configured to provide urgent care to patients in need by collecting symptom and medical data from patients and providing such data to relevant medical professionals and pharmacies. In some embodiments, the platform may facilitate diagnosis of a patient by a third-party medical provider and fulfillment of a drug prescription by a third-party pharmacy, without any of the parties having direct (e.g., physical or in person) contact.

FIG. 1 illustrates an example flowchart of an at-home testing protocol according to some embodiments described herein. In some embodiments, a patient may access the testing platform or a third-party site or application in connection with the testing platform. In some embodiments, upon indicating interest in a medical test, a pre-qualification survey, questionnaire, or online consultation may be transmitted or initiated at 102, in order to assess patient disease risk, eligibility for an at-home test, or other relevant factors, such as travel history, future travel plans, etc. In some embodiments, the user may receive the survey via display on a user device at 104. The user device may comprise, for example, a personal computer, a cellular phone, a smartphone, a laptop, a tablet computer, an e-reader device, an audio player, or another device capable of connecting to and communicating over a network, whether wired or wireless. In some embodiments, the platform may receive user input of survey answers from the user device and attempt to pre-qualify the user based on available guidelines at 106, such as government stipulated testing requirements. In some embodiments, at 106, information can be gathered about the user that may facilitate various functionality of the testing platform. For example, at 106, the user's identity can be verified. Verification of the user's identity can occur in various ways as described further below. In some embodiments, verification of the user's identity comprises checking the users ID (e.g., driver's license or passport). In some embodiments, verification of the user's identity comprises checking the user's identity using a health card or test pass as described further below. In some embodiments, the user's identity is verified using biometrics. Additionally, information about the user may be gathered at this stage which may facilitate matching the user to a proctor within the system in a manner that improves the efficiency of the system. User-proctor matching is described in more detail below. If a patient is pre-qualified, user information gathered during user registration and/or the patient survey may be transmitted by the platform to a third-party test prescriber at 108. In some embodiments, a medical test may not require a prescription, in which case a test could be directly sent to the patient without involvement of a third-party. In some embodiments, the third-party prescriber could be the administrator of the health testing and diagnostic platform.

In some embodiments, at 110, the platform may receive confirmation of a valid prescription of the requested medical test for the patient. The test, along with instructions on how to collect a test sample, may be delivered, for example, via mail, to the patient by the platform administrator or by a third-party. In some embodiments, at 112, a user patient may receive the requested test. Within a prescribed amount of time (or in some cases, an unspecified amount of time), the user patient may enter a test environment of the platform via a user device, such as a personal computer, a cellular phone, a smartphone, a laptop, a tablet computer, an e-reader device, an audio player, or another device capable of connecting to and communicating over a network, whether wired or wireless at 114. Further, the user device at 114 may be the same user device as used at 104 or it may be a different device. For example, the user may access the pre-qualification survey at 104 on a smart phone and then, at 114, enter the test environment on the same smart phone or on a different device, such as a table or laptop. Upon entering the testing environment or a virtual waiting room of the test environment, the platform may manually or automatically match the user patient with a medical provider proctor at 116 to administer the test. The system may provide user-proctor matching in a variety of ways to improve the efficiency and accuracy of the platform. As noted below, various factors of both the users and the proctors may be analyzed to facilitate user-proctor matching.

Upon matching of the user and the proctor, a testing session may begin at 120, with a prompt and testing session being provided to the proctor and a test session recording beginning at 122. In some embodiments, during the testing session, the proctor may guide the user patient through the testing process using provided prompts and tools in order to receive a test result at 124. The proctor and/or the platform may perform validation of the test result using a video feed of the test from the user device or through a static image taken by the user device at 126. In some embodiments, the platform may store the test result in connection with a user profile created for the patient at 128. Furthermore, at 128, the test results may be reported to various government agencies, health authorities, and/or third parties as mandated or desired. In some embodiments, the platform may generate and transmit the verified test result to the patient at 130. In some embodiments, the verified test results may be in the form of a digital health card or "passport" with various information including the test result, date of the test, expiration, and any other relevant details. In some embodiments, the verified test result may be received by the patient via the platform or a third-party website or application at 132.

Figure 2:
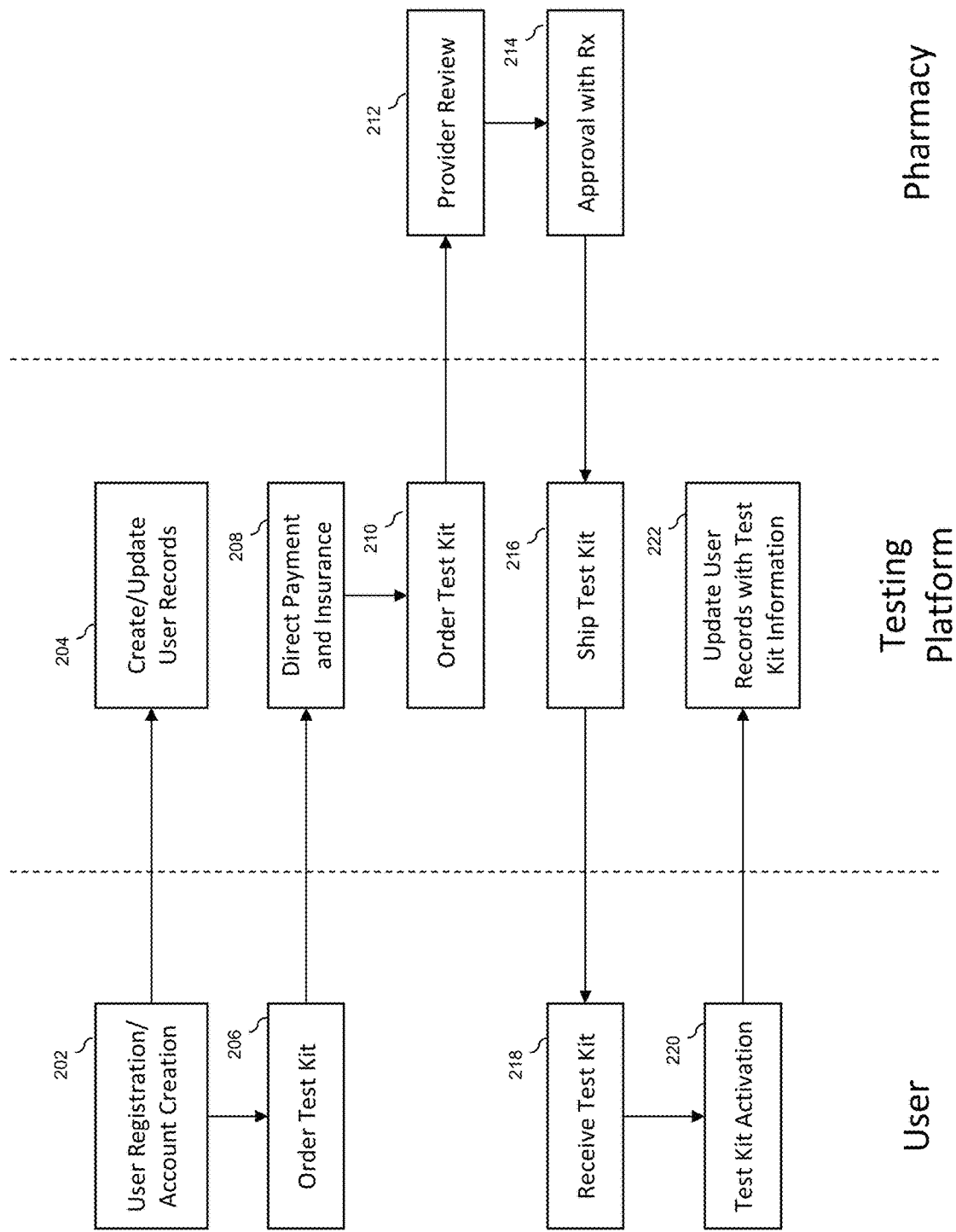
FIG. 2 illustrates an example flowchart of a method for registering a user and ordering a diagnostic test for an at home-testing protocol according to some embodiments described herein.

FIG. 2 illustrates an example flowchart of a method for registering a user and ordering a diagnostic test for an at home-testing protocol according to some embodiments described herein. In some embodiments, a user patient may access the platform and be prompted to register with the platform and create a user account at 202. In some embodiments, registration may involve collection of user data, such as personal information, medical history, and/or insurance information, among others. In some embodiments, registration and/or creation of a user account may result in a user profile creation within a user database of the platform, in which the above information may be stored at 204. In some embodiments, user identity information is verified and stored at 204. In some embodiments, information that will be used to facilitate user-proctor matching can be obtained and stored at 204.

Also, upon creation of a user account, the user may order a test kit at 206, which may involve a pre-qualification process such as that described with respect to FIG. 1. In some embodiments, the platform may process the test order, including payment and/or insurance at 208. Upon completion of the transaction process, the platform may automatically order a test kit, such as through an application programming interface, from a third-party pharmacy at 210. In some embodiments, the pharmacy may review the user information and request at 212 and approve a test kit order at 214. In some embodiments, after approval, a test kit may be shipped to the patient from the pharmacy, from the testing platform, or from a third party at 216. In some embodiments, the patient may receive the test kit at 218 and be prompted to activate the test kit at 220. Activation of the test may involve connecting test identification information with the user profile, in order to ensure that the patient is using the correct test at the time of the testing session. In some embodiments, the health testing and diagnostic platform may update the user profile of the patient with the unique test kit information at 222.

In some embodiments, one or more of the exchanges between the user and the testing platform as described above with reference to one or both of FIGS. 1 and 2 may be made through and/or facilitated by an inline frame or "iFrame" HTML element of a website or web application. In at least some of these embodiments, the website or web application may be hosted by an entity other than that which maintains the testing platform, such as a pharmacy or e-commerce business. Such an iFrame may effectively enable a website, web application, or components thereof that are hosted by the entity that maintains the testing platform to be embedded in the website or web application that is hosted by this other entity. In this way, users of the website or web application hosted by another entity, e.g., a pharmacy or e-commerce business, can quickly and seamlessly connect with the testing platform to order test kits, among other things. In some cases, test kit orders and/or prescription drug orders may be fulfilled at least in part by the other entity. For instance, if the other entity is a pharmacy, then test kit orders and/or prescription drug orders may be made available to users for pickup at their nearest pharmacy branch. Similarly, if the other entity is an e-commerce business, then test kit orders and/or prescription drug orders may be delivered to users by leveraging the business's existing supply chain and logistics infrastructure. In some embodiments, users may have the option to have test kit orders and/or prescription drug orders delivered to them via a shipping service or a courier service for rapid same day delivery.

As an example, the website for "Duncan's Pharmacy" may include an iFrame element that enables users of the website to interface with the entity that maintains the testing platform without having to manually navigate away from and/or back to the Duncan's Pharmacy website. As such, users of the website for Duncan's Pharmacy may be able to easily complete pre-qualification surveys, create accounts with the testing platform, order test kits, and the like. When ordering test kits through the iFrame on the Duncan's Pharmacy website, in some instances, users may be given the option to have the test kits delivered directly to them or pick their test kits up from their nearest location of Duncan's Pharmacy. Other arrangements are possible.

Figure 3:
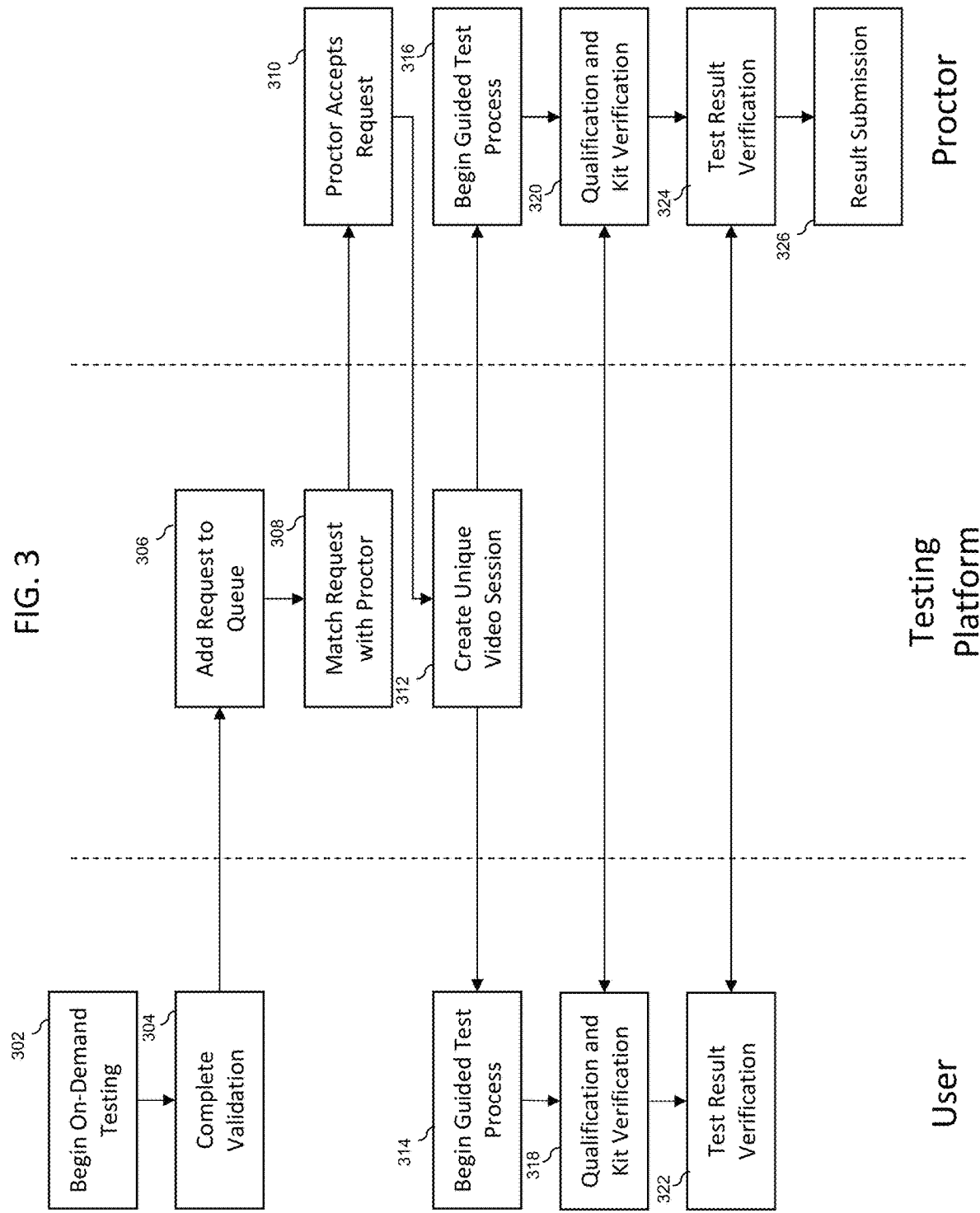
FIG. 3 illustrates an example flowchart of an on-demand testing protocol with a proctor according to some embodiments described herein.

FIG. 3 illustrates an example flowchart of an on-demand testing protocol with a proctor according to some embodiments described herein. In some embodiments, once a test kit has been received and activated by a patient, the patient may access the platform via a user device in order to initiate an on-demand testing session at 302. In some embodiments, the on-demand testing session must be initiated by the patient within a prescribed period of time after receiving or activating the test kit. In some embodiments, initiation of the testing session by the patient may cause the platform to place the patient in a virtual waiting room, where the patient's testing session will be queued at 306 pending a match with an available medical provider proctor at 308 In some embodiments, after the proctor has been matched with the patient or upon manual selection of the patient by the proctor, the proctor may review the patient information and accept the request to begin the testing session at 310. Acceptance of the request may initiate a unique, one-way or two-way video session between the patient and the proctor at 312 provided by the platform. In some embodiments, the video session may involve a guided test process at 314 for the patient on a user device and at 316 for the proctor using a proctor device, which could be a mobile device, laptop, desktop, or other computer device. As a first step in the testing session, the proctor and patient may follow provided on-screen steps to ensure that the patient is verified and qualified at 318, 320, as well as to verify the that the test to be used matches the test information stored in the user profile upon test activation. After verification and qualification, the proctor may guide the patient through a series of steps comprising a testing protocol in order to achieve a test result. In some embodiments, a test result may be verified by the proctor and/or patient at 322, 324. In some instances, test result verification involves a visual inspection of the test kit by the proctor to determine and manually submit the test result. In some embodiments, the verified test result is submitted by the proctor and stored within a test database of the platform at 326.

Figure 4:
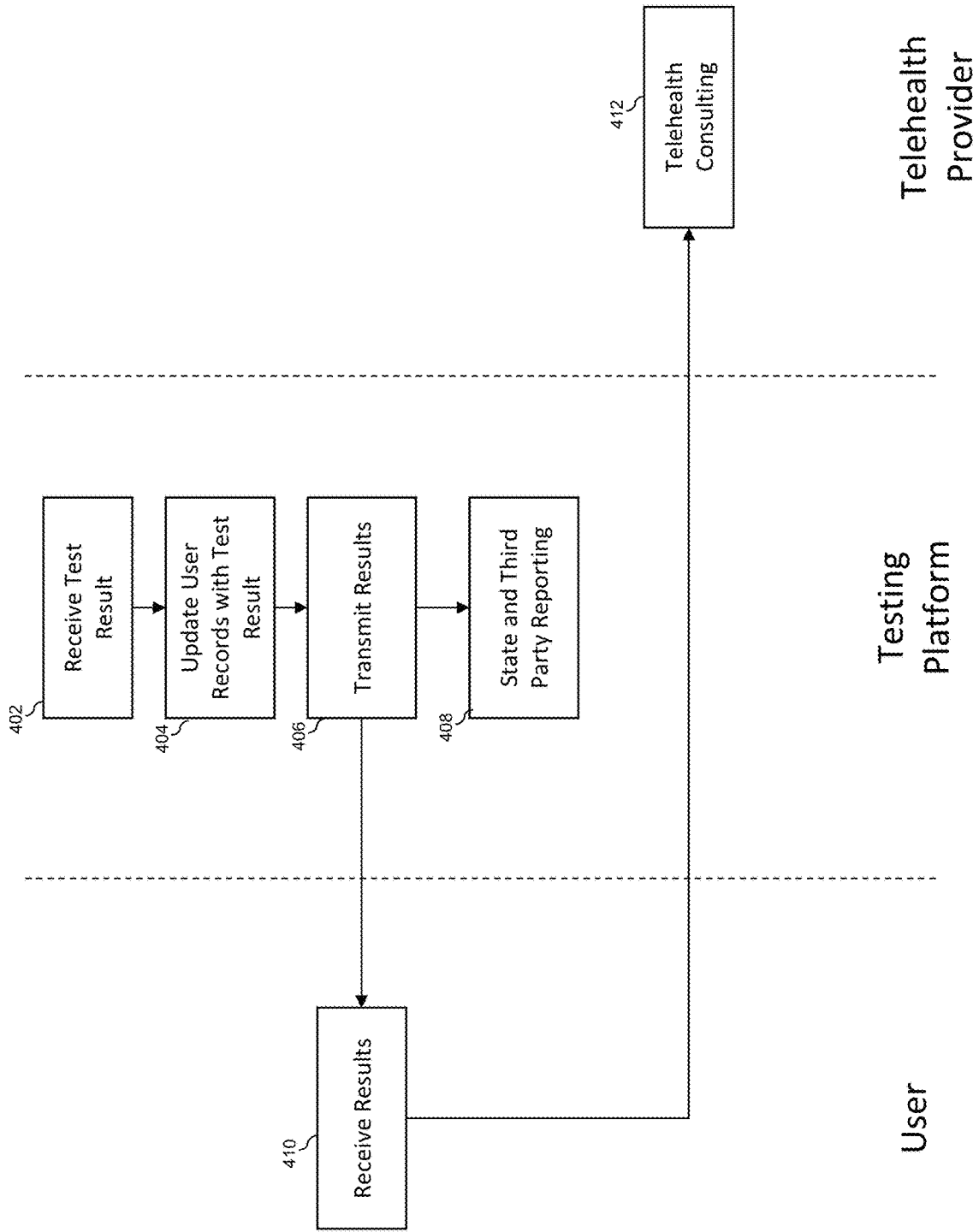
FIG. 4 illustrates an example flowchart of a method of reporting testing results according to some embodiments described herein.

FIG. 4 illustrates an example flowchart of a method of reporting testing results according to some embodiments described herein. In some embodiments, a verified test result may be received by the testing platform at 402 from a testing session completed by a patient and proctor. In some embodiments, the platform may update the user profile with the verified test results at 404. In some embodiments, at 406, the platform may transmit the verified test results to various third-party entities, including national, state, and/or local government entities and third-party entities at 408, and to the user at 410. In some embodiments, transmission of the verified test result to the user may be through a third-party. In some embodiments, the verified test results may be transmitted in the form of a health card or passport, with additional information regarding the test, including the test type, date of the test, test determination or result, or any other relevant information. In some embodiments, in the event of a positive test, the user patient may be referred to a telehealth consultant via the platform or by a third-party at 412.

Figure 5:
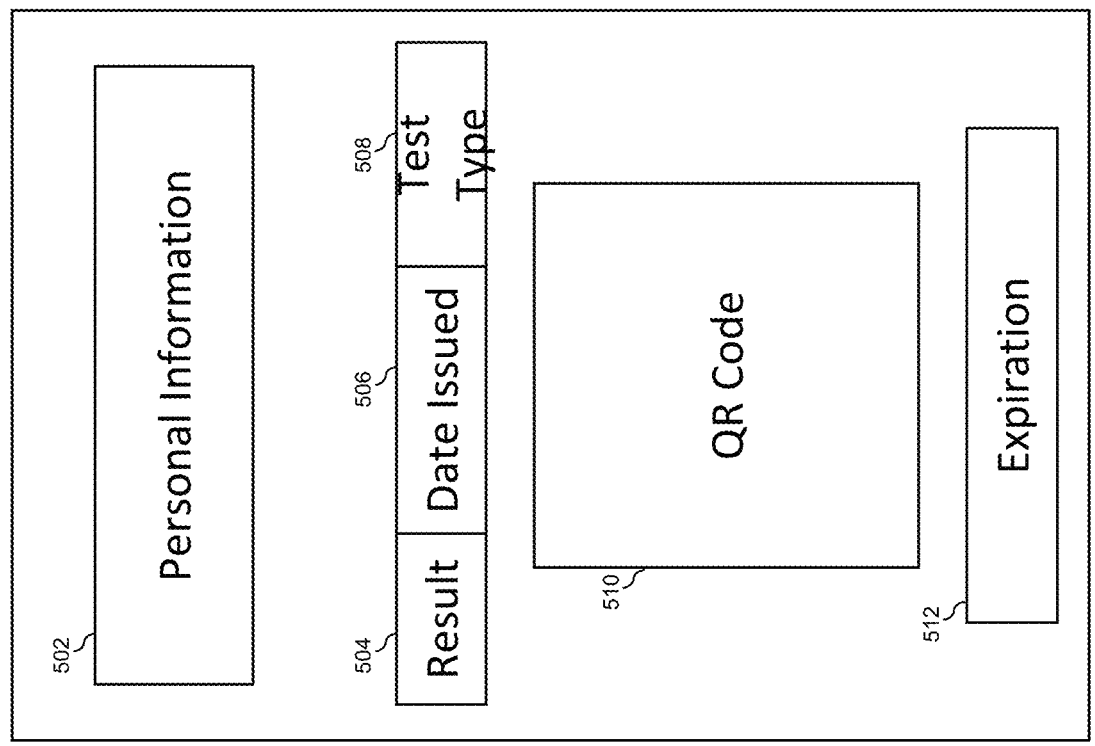
FIG. 5 illustrates an example diagram of a health card according to some embodiments described herein.

FIG. 5 illustrates an example diagram of a health card or test pass according to some embodiments described herein. In some embodiments, as noted above, verified test results may be transmitted to a user patient in the form of a health card, test pass, or health passport. Such a health card may provide an easily accessible summary of test results to a patient and to interested third parties such as government officials, travel authorities, or event organizers/security. In some embodiments, the health card 500 may comprise personal information 502, identifying the user patient by the patient's name, date of birth, photograph, or otherwise. In some embodiments, the health card may also comprise a test result 504, a date of issue of the test result 506, and a test type 508. In addition, the health card may comprise an expiration 512, which may comprise easily accessible information regarding expiration of the dependability of the test result based on health guidelines provided by government entities or otherwise. In some embodiments, the health card 500 may comprise a quick response (QR) code that may direct interested parties to a webpage containing additional information about the patient, the test, the test results, and/or other tests that the patient has undergone. Additional detail regarding test passes is described further below.

Figure 6:
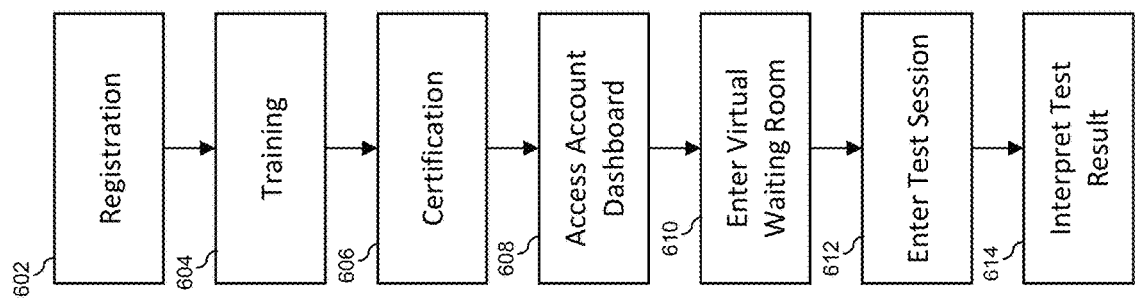
FIG. 6 illustrates an example flowchart for a proctor certification and testing protocol according to some embodiments described herein.

FIG. 6 illustrates an example flowchart for a proctor certification and testing protocol according to some embodiments provided herein. In some embodiments, a medical provider may apply and register to become a proctor for the health testing and diagnostic platform through, for example, a website or mobile application at 602. In some embodiments, the proctor may undergo a training process at 604 in order to prepare the medical provider to manage patient testing sessions and administer at-home medical testing via the platform. Upon passing one or more certification and verification tests, the proctor may be certified by the platform automatically or upon manual approval of an administrator at 606. In some embodiments, once certified, a proctor may gain access to a proctor dashboard at 608, wherein the proctor dashboard may be used to track testing statistics, proctor performance, and initiate test sessions. In some embodiments, initiating a testing session via the dashboard may enter the proctor into a virtual waiting room at 610, where the proctor may select a patient (or patients) for a testing session or be automatically assigned to a patient (or patients). In some embodiments, after verifying patient information, the proctor may enter a test session with the patient(s) at 612. In some embodiments, upon completion of prompts (e.g., step-by-step prompts) comprising the test session protocol, a test result may be obtained, which can be interpreted and submitted by the proctor at 614.

Figure 7:
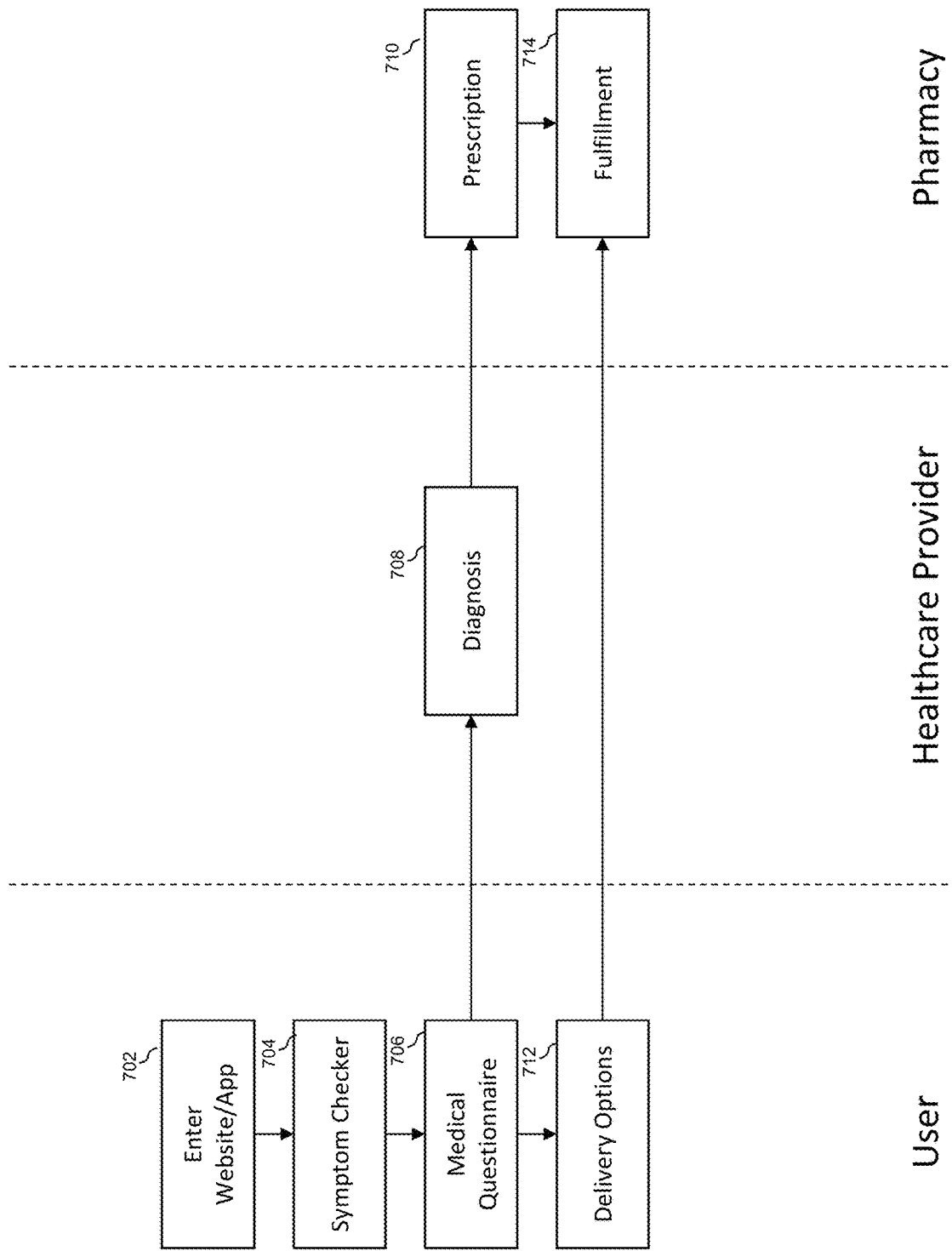
FIG. 7 illustrates an example flowchart for providing urgent care to a patient via a health testing and diagnostic platform according to some embodiments described herein.

FIG. 7 illustrates an example flowchart for providing care to a patient via a health testing and diagnostic platform according to some embodiments provided herein. In some embodiments, in addition to providing a remote medical test environment, the platform may be used to provide general, urgent, or emergency care to a patient through connection of patients to third-party medical providers. In some embodiments, a user patient may enter a website or app of the platform at 702. In some embodiments, the user patient may be prompted to answer a series of questions generated by the platform in order to verify symptoms of and/or other information about the user patient at 704. In addition to the symptom checker, the user patient may also be prompted by the platform to complete a medical questionnaire to provide additional information regarding the patient's condition, health history, and/or other relevant information at 706. In some embodiments, the information gathered at 704 and 706 can include information regarding the user patient's travel history and/or future travel plans. For example, the process of can include presenting the user with questions regarding their travel plans (e.g., "Are you planning to travel into or out of the United States within the next 72 hours?"). The information from the symptom checker and the medical questionnaire may be transmitted automatically at 708 to a third-party or registered healthcare provider. The information may be routed to specific medical providers based on the answers provided by the patient such that medical providers with specific expertise, language skills, and/or location may be selected. In some embodiments, the medical provider may provide a diagnosis to the patient, at 708 which may include one or more drug or test prescriptions at 710 to be fulfilled at 714 via a third-party pharmacy. All of the above steps can be completed by the platform without the patient being physically present with the medical provider or at the pharmacy. In some embodiments, the patient may be prompted to provide delivery information to the platform at 712, which may be automatically transmitted to the pharmacy for fulfillment of the prescription.

As mentioned above, in some embodiments, one or more of the exchanges between the user and the testing platform as described above with reference to one or both of FIGS. 1 and 2 may be made through and/or facilitated by an iFrame of a website or web application. Similarly, in some embodiments, the user may enter the website or app of the platform at 702 in FIG. 7 through an iFrame element provided on a website or web application that is hosted by an entity other than that which maintains the platform, such as a pharmacy or e-commerce business. As such, in these embodiments, one or more of the exchanges between the user and the platform at one or more of 704, 706, and 712 may occur by way of the iFrame.

FIG. 8 illustrates an example pre-testing confirmation interface according to some embodiments. The pre-testing confirmation interface may be displayed to a patient who has indicated that the patient is ready to begin testing. In some embodiments, the pre-testing confirmation interface may comprise various verification questions that are designed to ensure that the patient has the time and materials necessary to being a testing session. For example, it may be required that the patient has at least 20 minutes to administer the test, as well an unopened test package received via mail or otherwise properly obtained. Within the pre-testing confirmation page, the patient may also need to verify personal information, such as their date of birth, in order to proceed to the virtual waiting room and to a testing session.

FIG. 9 illustrates an example pre-testing virtual waiting room according to some embodiments provided herein. In some embodiments, the pre-testing virtual waiting room may be displayed to a patient after completing pre-testing verification and confirmation. In the virtual waiting room, the patient may await dynamic connection with a proctor, who will oversee a testing session with the patient. In some embodiments, once a proctor has selected to begin a test with the patient or is automatically assigned to the patient, a unique activation code may be transmitted to the patient via short message service (SMS), text message, electronic mail (E-mail), voice call, or another electronic communication channel.

FIG. 10 illustrates an example unique code submission interface according to some embodiments provided herein. In some embodiments, a patient may be directed to the unique code submission interface once the patient has been matched with a proctor. In some embodiments, the match may occur after the patient enters a virtual waiting room. In some embodiments, the unique code submission interface may allow the patient to enter a unique activation code for entering a private one-way or two-way communication channel with a proctor. In some embodiments, the unique code submission may initiate testing session between the patient and the proctor.

Figure 11:
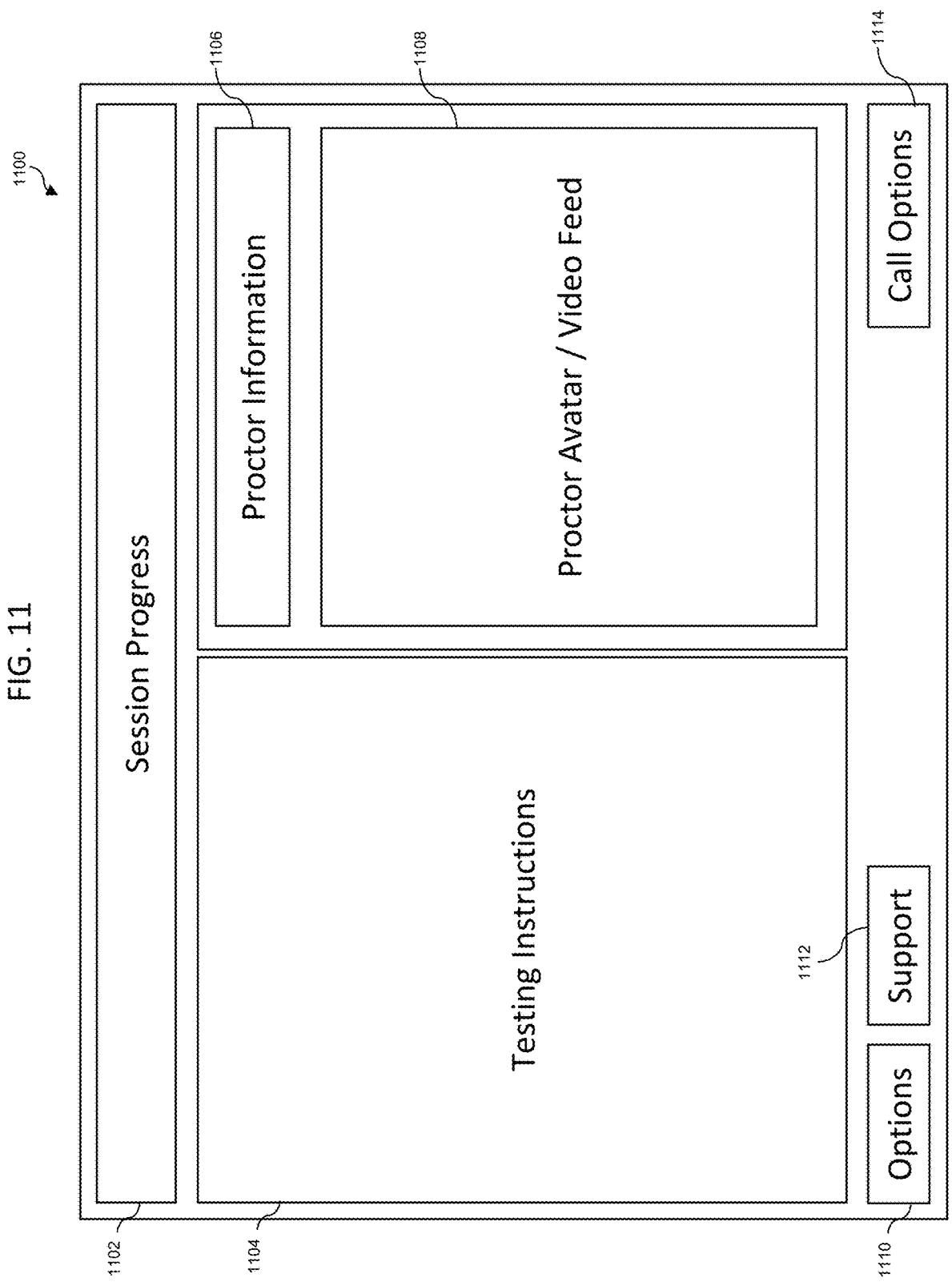
FIG. 11 illustrates an example patient testing interface according to some embodiments described herein.

FIG. 11 illustrates an example patient testing interface according to some embodiments provided herein. The example testing interface 1100 may be displayed to a patient for facilitating one or more medical tests on the patient and provides instructions and tools for self-administering the test and connecting with a proctor, who oversees and provides guidance during the test. The interface may be designed to accurately record a patient test result and to allow the patient to understand the exact step-by-step procedure that must be followed to achieve a successful test result.

In some embodiments, the example testing interface 1100 may comprise a session progress indicator 1102. The session progress indicator 1102 may provide a visual and/or audible indicator of the progress of a testing session. For example, the session progress indicator 1102 may show a step number, a timer, a timeline, or other indicator of progress. The session progress indicator 1102 may assist a patient in determining the current status of the testing session.

In some embodiments, the example testing interface 1100 may comprise testing instructions 1104. In some embodiments, the testing instructions 1104 may comprise step-by-step instructions that the patient must follow in relation to a provided at-home test kit in order to self-administer the test and achieve a valid test result. In some embodiments, the testing instructions 1104 may be read by a patient in addition to audible instructions provided by the platform or manually by a proctor. The proctor may be heard by the patient via a secure communication channel and in some embodiments, may be visible in a live proctor video feed 1108. In other embodiments, a virtual proctor avatar may be shown instead of the proctor video feed. In some embodiments, a prerecorded video may be displayed rather than a live proctor video feed.

In some embodiments, proctor information 1108 may be displayed and provide information to the patient regarding the proctor that is overseeing the testing session, including, for example, the proctor's name, certifications, and a photograph of the proctor, among others.

In some embodiments, the example testing interface 1100 may also comprise one or more options 1110, a support link 1112, and one or more call options 1114. In some embodiments, the options 1110 may comprise general platform options, including accessibility options, video options, and other miscellaneous options. In some embodiments, the support link 1112 may connect the patient to an administrator or other support personnel, in the event that such support is needed. For example, if there is an emergency with the proctor or patient, or there is an issue with testing, the support link 1112 may allow a third-party to join the testing session. The call options 1118 may, for example allow a patient to mute their device microphone or end the testing session.

Figure 12:
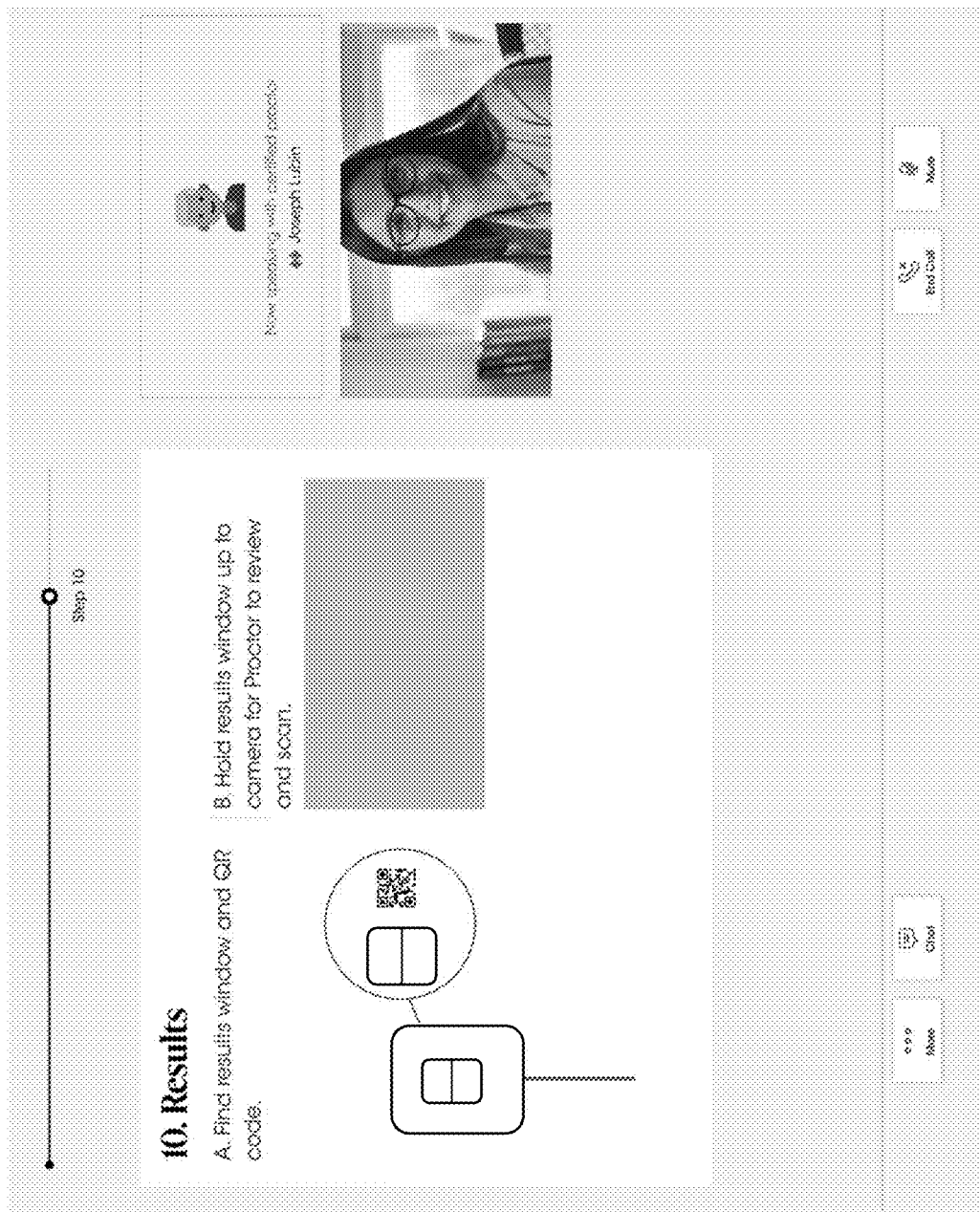
FIG. 12 illustrates another example patient testing interface according to some embodiments described herein.

FIG. 12 illustrates another example patient testing interface according to some embodiments described herein. In some embodiments, the patient testing interface may comprise directions to register a medical test using a camera on the user device. For example, some commercially available diagnostic tests comprise a QR code comprising a data matrix that has an encoded ID. In some embodiments, the platform may perform a scan through the user camera to read the data matrix. In some embodiments, the read data may be sent automatically to the test provider through, for example, an application programming interface. In some embodiments, the delivery and patient data and all other pertinent information may be retrieved from the test provider to verify that the test and patient in the testing session match with the platform records. In some embodiments, the user may be directed to display or scan the code multiple times throughout a testing session in order to verify that the same test is being used throughout an entire session. For example, scanning the code at the start of the testing session, immediately before and after critical testing steps, and/or at the end of the testing session can prevent a user from switching tests midway through the testing session. In some embodiments, the data matrix can also be read, such that a unique code is obtained, which can be compared against all previous codes read by the platform. If a duplicate code is read, the test may be discarded.

Figure 13:
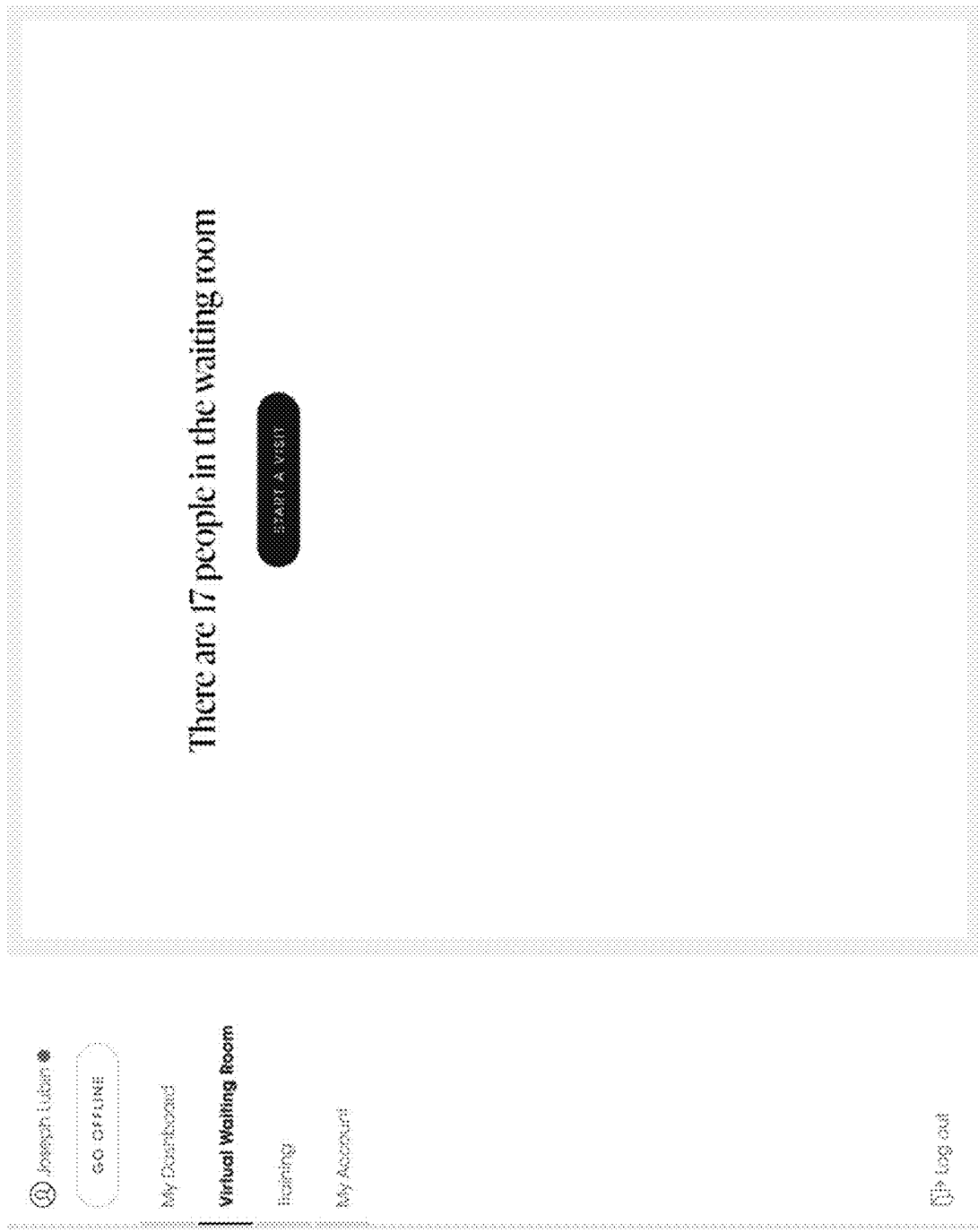
FIG. 13 illustrates an example test initiation interface according to some embodiments described herein.

FIG. 13 illustrates an example test initiation interface according to some embodiments herein. In some embodiments, the test initiation interface comprises a test initiation mechanism and an indicator of the number of patients waiting in a virtual waiting room. Upon, selection of the test initiation mechanism, a test session may begin between a proctor and a patient. In some embodiments, a proctor may be prompted to select a patient from a list of patients in the virtual waiting room. In some embodiments, the proctor may be automatically and dynamically assigned to a patient in the waiting room. In some embodiments, the assignment may be based on proctor location, language ability, medical expertise, or other factors. In other embodiments, the assignment may be made based on wait time of patients.

Figure 14:
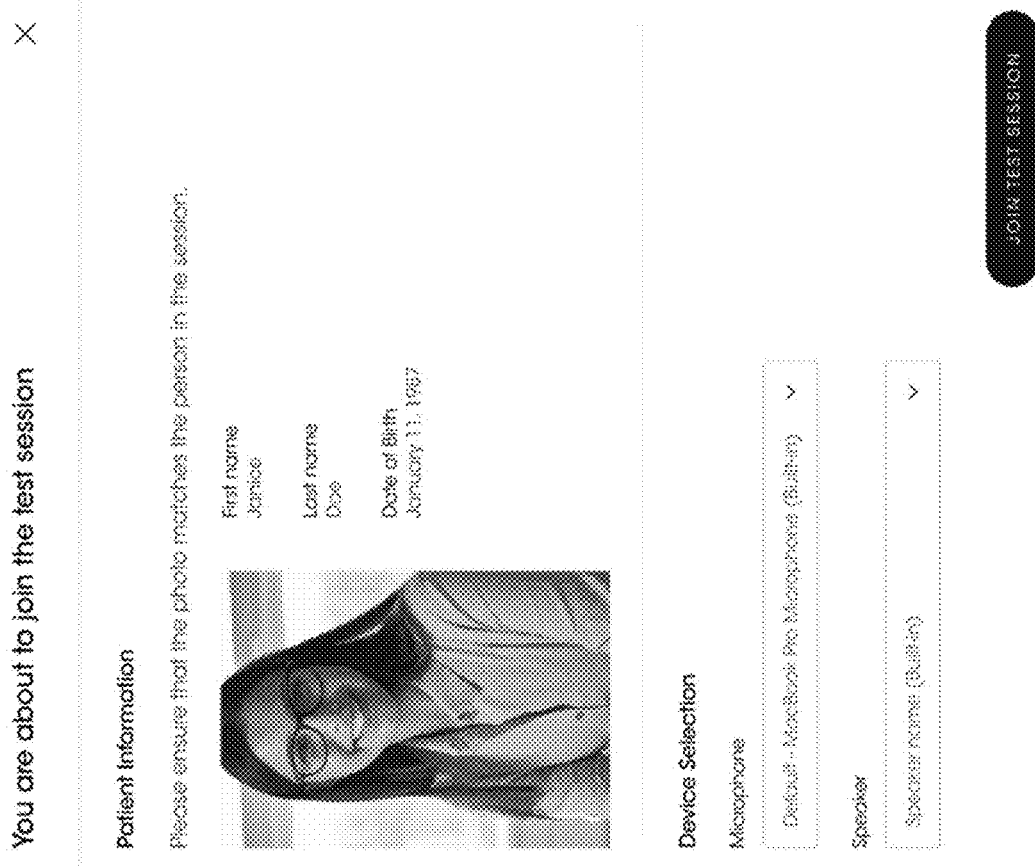
FIG. 14 illustrates an example pre-testing interface according to some embodiments described herein.

FIG. 14 illustrates an example pre-testing interface according to some embodiments herein. In some embodiments, the pre-testing interface of FIG. 14 may be displayed to a proctor upon initiating a test session. The pre-testing interface may comprise patient information, such as the patient's name and date of birth, as well as a photo of the patient. In some embodiments, the proctor may be prompted to verify that the patient that joins the testing session matches the patient shown in the patient photo of the pre-testing interface. In some embodiments, the pre-testing interface may comprise one or more audio/video options, such as options for selecting a microphone and speaker for conducting the testing session.

Figure 15A:
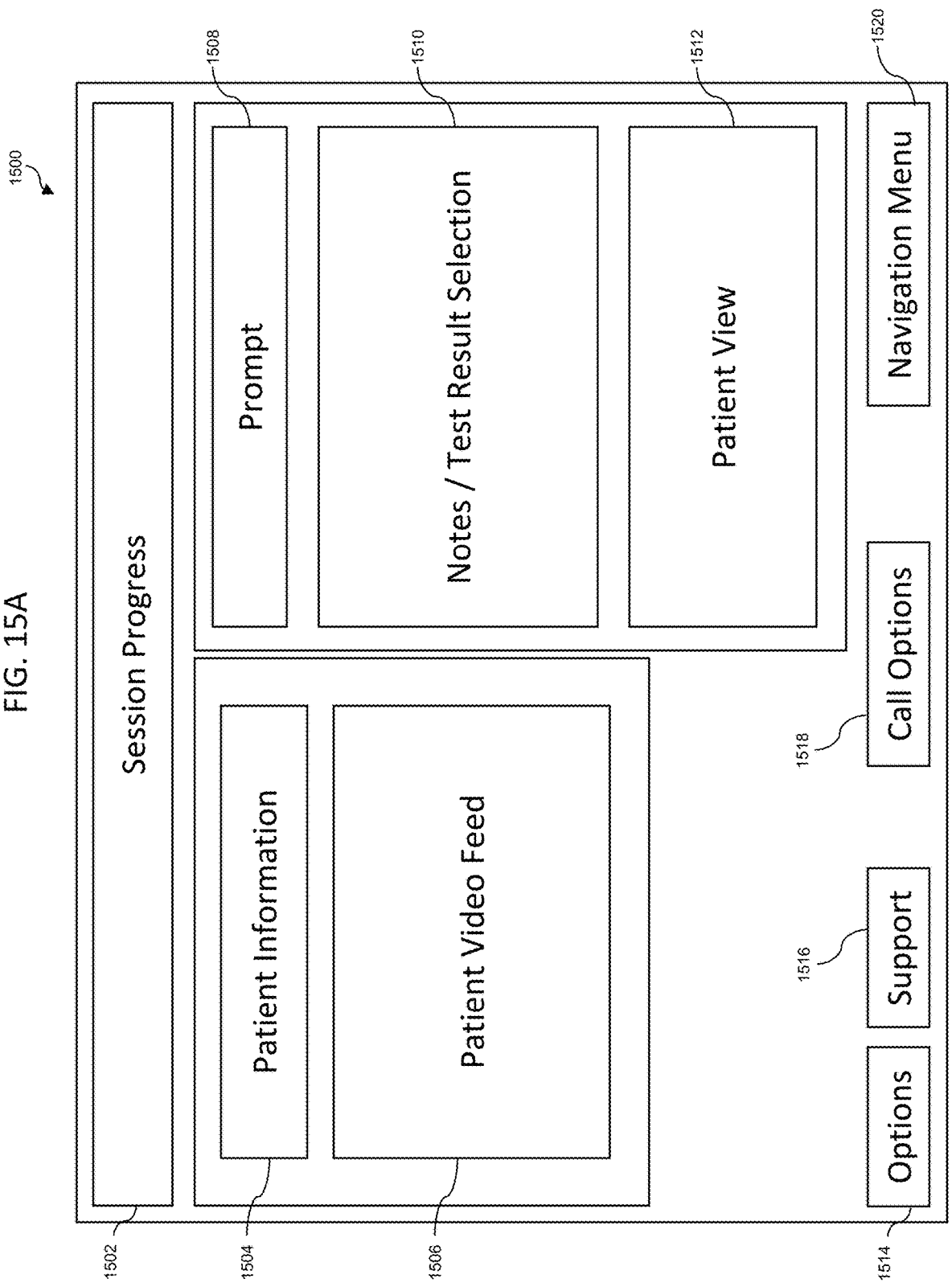
FIG. 15A illustrates an example testing interface according to some embodiments described herein.

FIG. 15A illustrates an example testing interface 1500 according to some embodiments herein. In some embodiments, the example testing interface 1500 may be displayed to a proctor for testing one or more patients and provides tools to facilitate management of testing, including verbal prompts, a video feed of the patent, and a timer and alert mechanism for the test read. The interface may be designed to accurately record a patient test result and to allow the proctor to provide useful information about various issues that may have resulted in a failed result or no result being obtained.

In some embodiments, the example testing interface 1500 may comprise a session progress indicator 1502. The session progress indicator 1502 may provide a visual and/or audible indicator of the progress of a testing session. For example, the session progress indicator 1502 may show a step number, a timer, a timeline, or other indicator of progress. The session progress indicator 1502 may assist a proctor in determining the current status of the testing session, especially in situations in which the proctor is managing multiple testing sessions simultaneously.

In some embodiments, the example testing interface 1500 may comprise patient information 1504 and a patient video feed 1506. The patient information 1504 may provide information to the proctor regarding the patient that is the subject of a testing session, including, for example, the patient's name, date of birth, age, language, and a photograph of the patient, among other types of information. In some embodiments, the patient video feed 1506 may comprise a live video feed of the patient during the testing session. In some embodiments, the patient video feed may comprise a recording of the patient. In some embodiments, the patient video feed 1506 may allow a proctor to monitor a patient and testing session, and to direct the patient regarding the test protocol.

In some embodiments, the example testing interface 1500 may also comprise a prompt/script 1508, a notes/test result section 1510, and a patient view 1512. In some embodiments, the prompt 1508 may comprise a written script for the proctor to audibly read to the patient during the testing session. In some embodiments, the prompt 1508 may automatically update based on the current step of the testing session. In some embodiments, a navigation menu 1520 may be sued by the proctor to move forward and back through the testing steps. In some embodiments, the notes/test result section 1510 may comprise various notes for the proctor's consideration during the current testing step. During interpretation of a test, the notes/test result section 1510 may comprise a guide for test interpretation and/or a mechanism to submit a test result. In some embodiments, the patient view 1512 may comprise a section showing the content that is currently being displayed on a patient's computer. In some embodiments, the patient view 1512 may comprise a copy of the content displayed on the patient's screen or a live stream of the patient's screen.

In some embodiments, a prompt 1508 may comprise a written script on the interface, which will indicate, for each step of or whatever phase of testing the particular patient is in, the words that the proctor will read for that specific step. In some embodiments, the prompt may be automatically read by the health testing and diagnostic platform. In other embodiments, the proctor may read the prompt audibly to the patient. In some embodiments, a prerecorded video or dialogue may be played at specific times during the testing, which will comprise a prerecorded script comprising the prompt 1508. In some embodiments, the prerecorded script may be played under supervision of a proctor.

In some embodiments, the example testing interface 1500 may also comprise one or more options 1514, a support link 1516, and one or more call options 1518. In some embodiments, the options 1514 may comprise general platform options, including accessibility options, video options, and other miscellaneous options. In some embodiments, the support link 1516 may connect the proctor to an administrator or other support personnel, in the event that such support is needed. For example, if there is an emergency with the proctor or patient, or there is an issue with testing, the support link 1516 may allow a third-party to join the testing session. In some embodiments, a substitute proctor may be able to join the testing session to resume testing using, for example, the session progress indicator 1502 and the prompt 1508.

In some embodiments, the health testing and diagnostic platform may assign one or more designated users (e.g., supervisors or others) to have administrator rights and privileges. In some embodiments, an administrator may view the full scope of proctor sessions occurring, including a list of proctors active on the platform and pending test sessions. In some embodiments, an administrator can join into a testing session anonymously and quietly as a third-party overseer, for purposes such as random audits. In some embodiments, administrators may join testing session for joint proctor training or feedback. In some embodiments, in an emergency situation, the support link 1516 may connect the proctor to a customer service team, wherein the customer service team may be sent part of or the whole dataset of a testing session, including the user information, the user picture, and proctor information.

FIG. 15B illustrates another example testing interface according to some embodiments provided herein. In some embodiments, the testing interface may comprise a video feed 1506 comprising an image/video of the patient 1522 or a plurality of images/videos of a plurality of patients. In some embodiments, software, such as machine learning or artificial intelligence software, or non-machine learning or artificial intelligence algorithms (for example, image segmentation analysis, pattern recognition, or the like) or otherwise, may be used to detect elements within the video feed 1506. These elements may include, for example, a patient 1522, a patient reference element 1524, a test 1526, and a test reference element 1528. In some embodiments, the software may be configured to monitor the video feed 1506 to ensure proper test protocol and completion. For example, in some embodiments, the software may utilize image or video recognition algorithms to periodically or continuously measure one or more relative distances and/or movements of the patient reference element 1524 and the test reference element 1528. In some embodiments, the patient reference element 1524 may comprise the patient's nostril, nose, lip, mouth, eye, ear, or any other body part. In some embodiments, the testing reference element 1528 may comprise a line or other visual indicator on the test 1526. In some embodiments, by measuring a horizontal and/or vertical distance and/or movement between the patient reference element 1524 and the test reference element 1528, the software may compare such values against predetermined threshold values to verify proper testing protocols are satisfied, for example, minimum/maximum distance traveled or reached, minimum/maximum number of motions and/or rotations performed. In other embodiments, machine learning and/or artificial intelligence may be used to interpret the patient video feed 1506 to verify testing procedures are completed properly.

Figure 16:
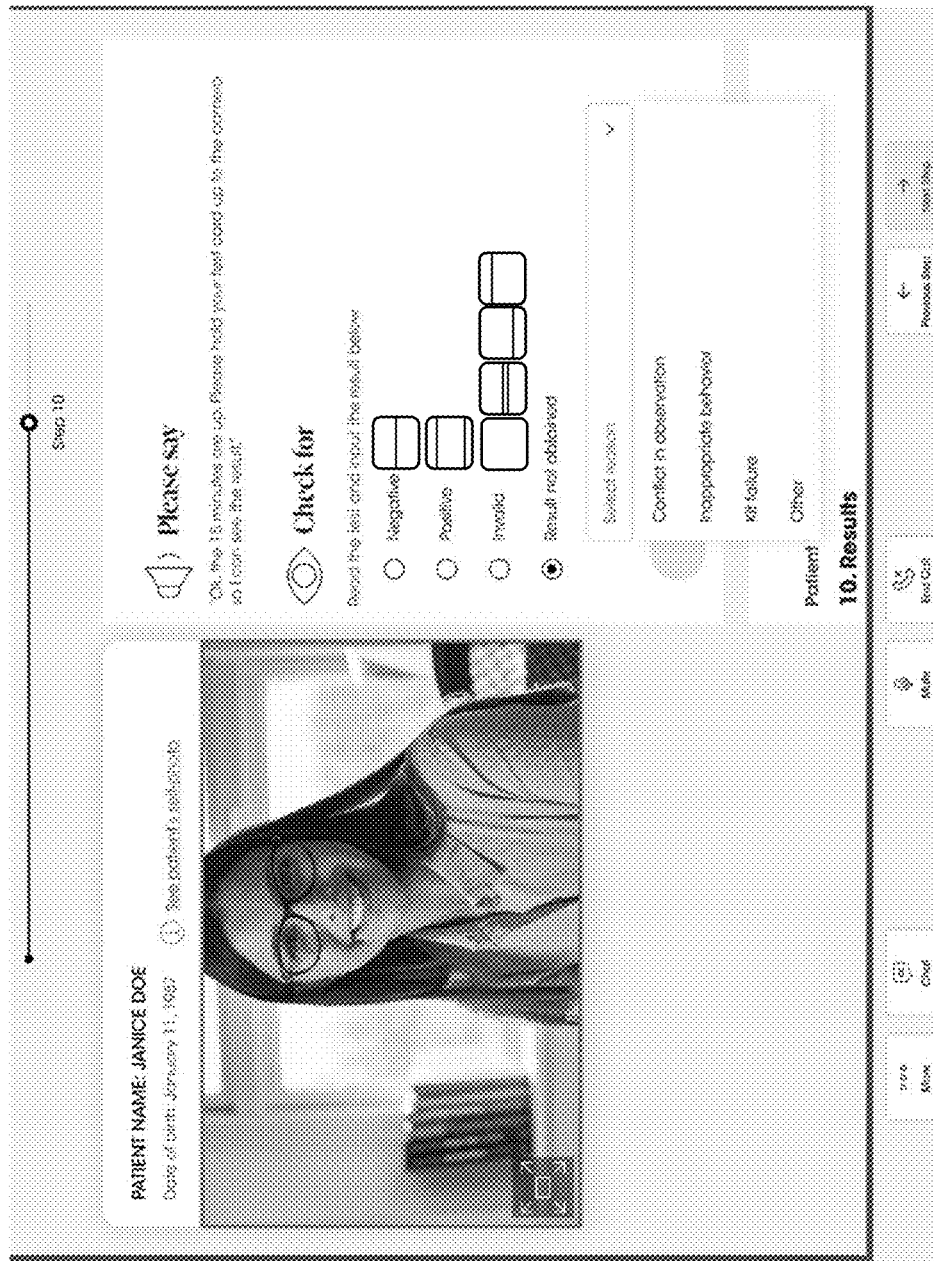
FIG. 16 illustrates an example test analysis and interpretation interface according to some embodiments described herein.

FIG. 16 illustrates an example test analysis and interpretation interface according to some embodiments herein. In some embodiments, during a test or upon completion of a test by a patient, the test may be displayed on a camera of a user device, such that the test and result can be verified. In some embodiments, the test may be verified manually by a proctor viewing the image of the test displayed via the test analysis and interpretation test analysis and interpretation interface. In some embodiments, the health testing and diagnostics platform may record the patient video to verify test integrity.

In some embodiments, the test analysis and interpretation interface may comprise one or more interactive tools, which the proctor may utilize to ensure test integrity. For example, one tool that may be used would be an interactive pen/marker/highlighter that can be used to annotate the patient video feed to guarantee that the test is not moved or altered.

Figure 17:
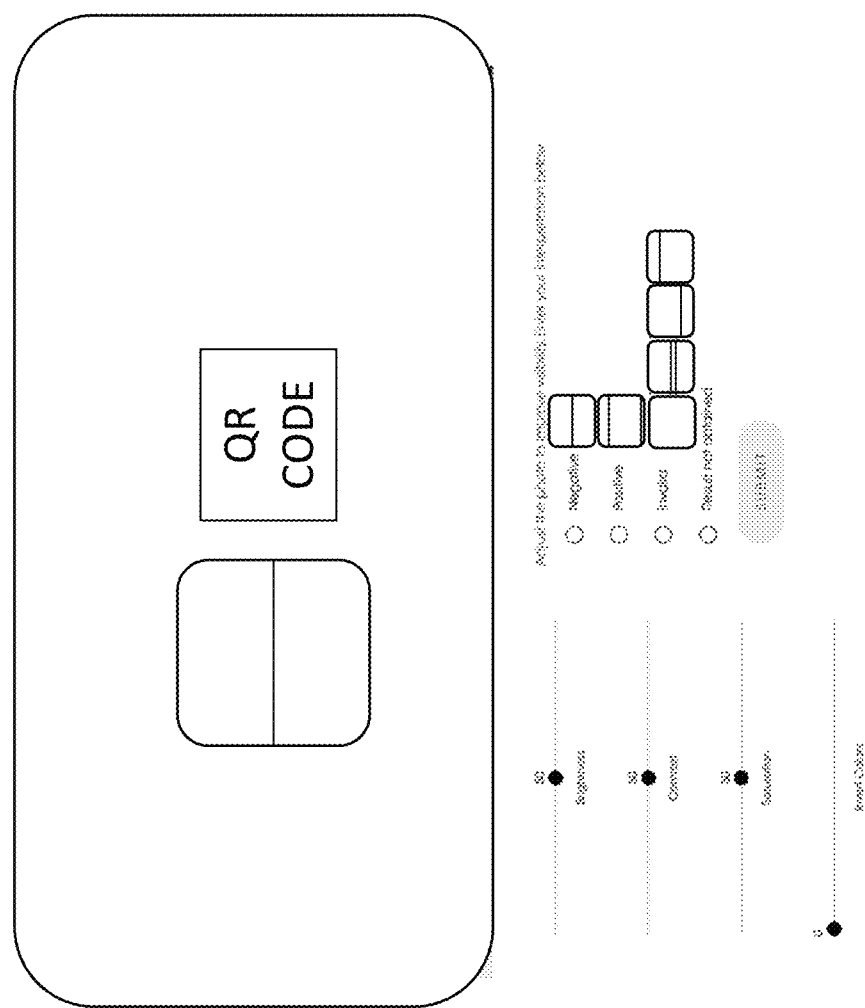
FIG. 17 illustrates another example test analysis and interpretation interface according to some embodiments described herein.

FIG. 17 illustrates another example test analysis and interpretation interface according to some embodiments herein. FIG. 17 illustrates a patient video feed showing a completed test awaiting interpretation. Within the test analysis and interpretation interface, a proctor may view a patient test image/video, interpret a test results, and select the interpreted test results for submission.

In some embodiments, a patient video feed or test image is not optimal such that the result may be difficult to interpret. For example, the patient's video may be too bright or dark, may be blurry, or otherwise lack sufficient visibility. Thus, in some embodiments, the test analysis and interpretation interface may comprise one or more image adjustment tools to manipulate image properties such as the contrast and brightness. The image adjustment tools may be used to adjust the image to enrich the view of the test. Example image adjustment tools include, for example, brightness, contrast, saturation, and color adjusters, among others.

In some embodiments, instead of utilizing live video of a patient test, the health testing and diagnostic platform may capture one or more static images of a patient test from the live video feed. In some embodiments, the static image may be captured directly from the user device of the patient. In some embodiments, the test image can be sent as a full-size file over the internet to the proctor and viewed on the test analysis and interpretation interface. In some embodiments, the image can be adjusted using the one or more image adjustment tools. In some embodiments, using an image captured using the user device may result in an image that has enhanced resolution and clarity relative to using a live image streamed over a video conferencing network. In some embodiments, the image of the test obtained from the user device of a patient may be captured during a patient video session with the proctor, but is not captured from the live video stream.

Figure 18:
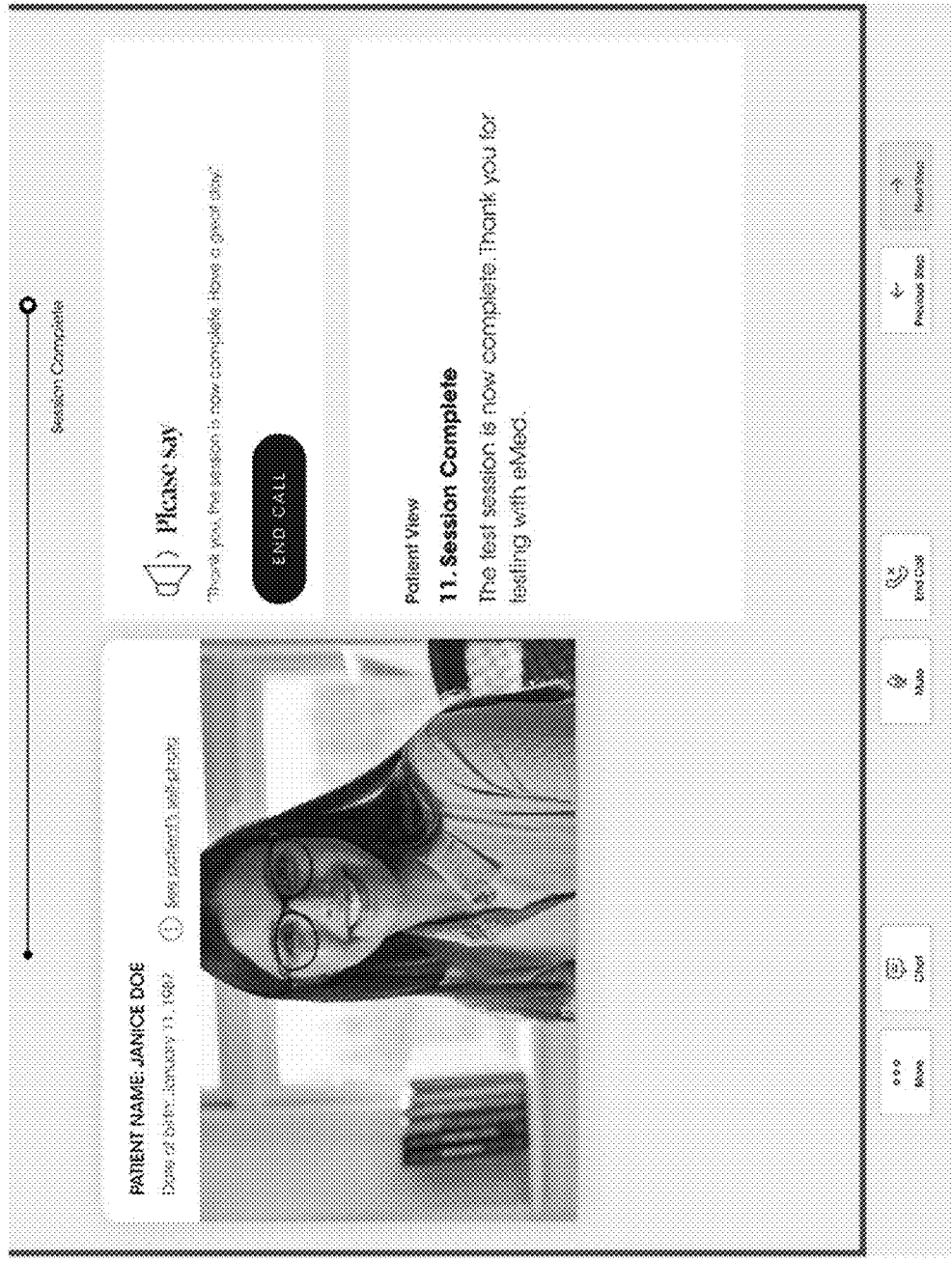
FIG. 18 illustrates an example another example testing interface according to some embodiments described herein.

FIG. 18 illustrates another example testing interface according to some embodiments herein. The testing interface of FIG. 18 illustrates the conclusion of a testing session from the proctor perspective. The testing interface comprises a mechanism for ending the testing session and severing the audio/video channel with the test patient.

Figure 19:
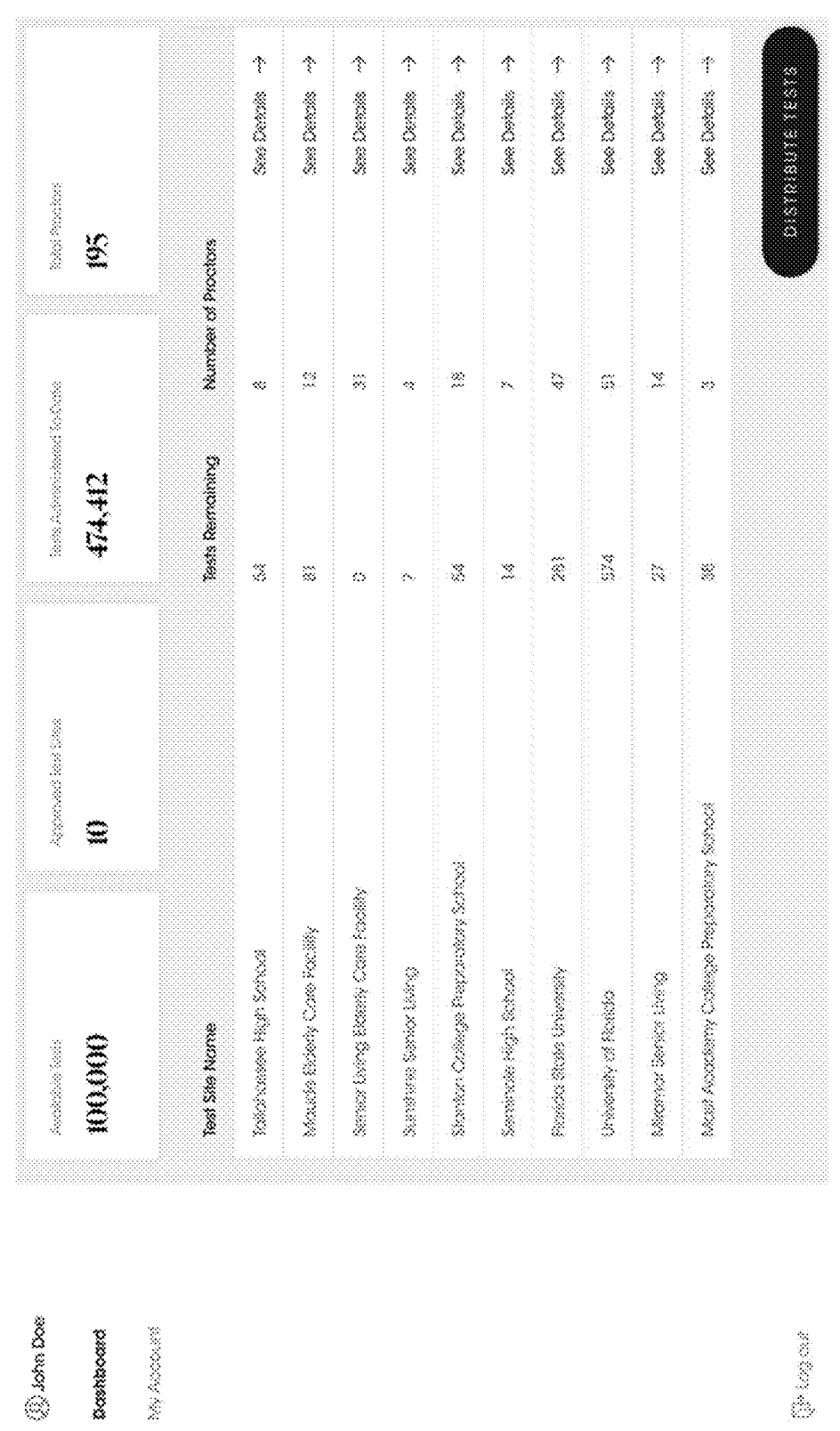

FIG. 19 illustrates an example testing summary interface according to some embodiments provided herein. In some embodiments, the testing summary interface may be used by an administrator, proctor, or health official to analyze testing statistics and distribution across one or more test sites or demographics. For example, the testing summary interface may comprise data including remaining available tests, approved test sites, a number of administered tests, a number of tests, and a distribution of administered tests and proctors across test sites. From the testing summary interface, a user may access a test distribution interface, as described with respect to FIG. 20.

Figure 20:
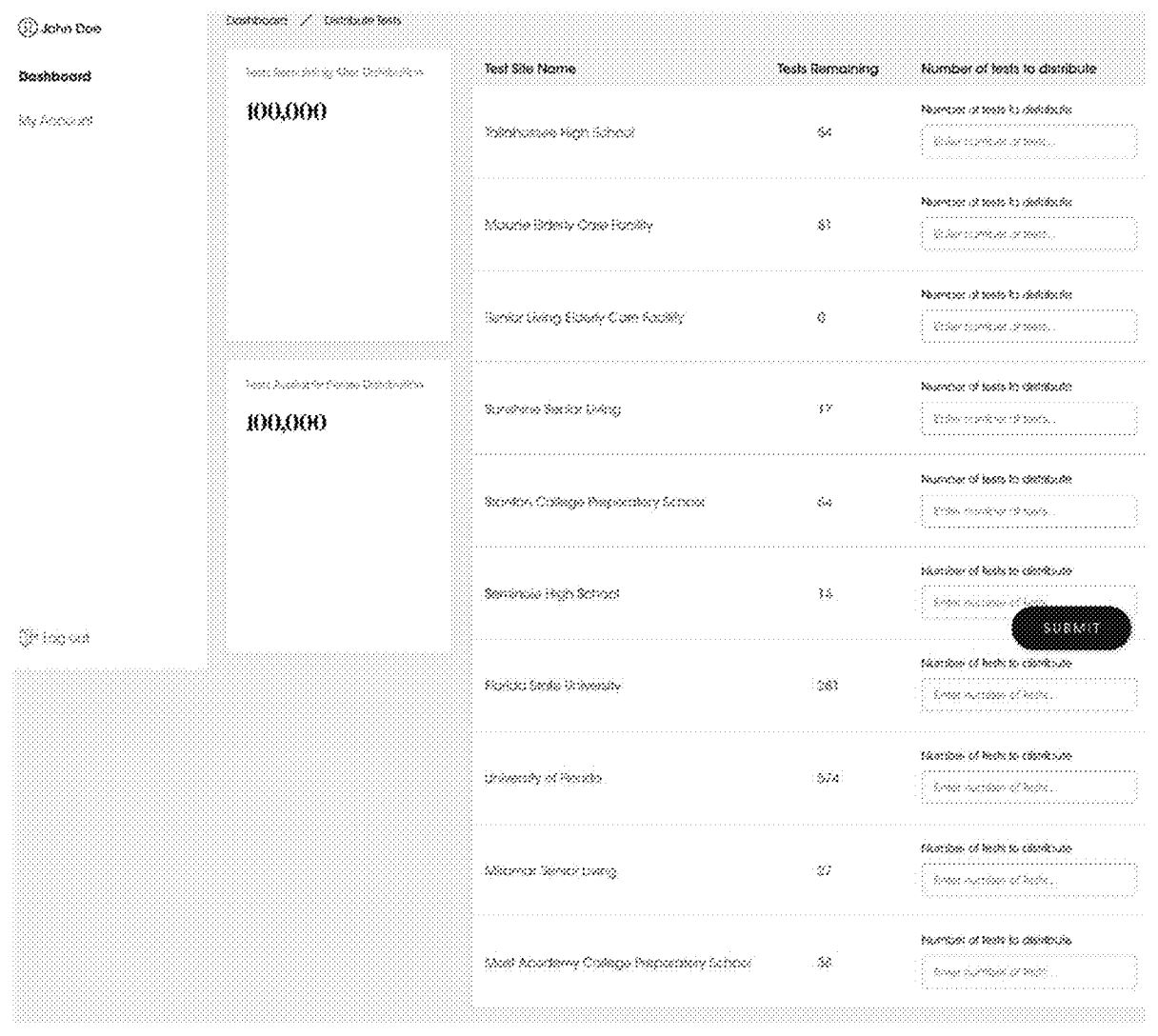

FIG. 20 illustrates an example test distribution interface according to some embodiments provided herein. In some embodiments, the test distribution interface may be used by an administrator, proctor, or health official to distribute available tests among one or more test sites to be administered with or without the health testing and diagnostic platform remote testing protocol. Submission of a test distribution may automatically initiate an order and/or distribution of the submitted tests to the selected test sites.

Figure 21:
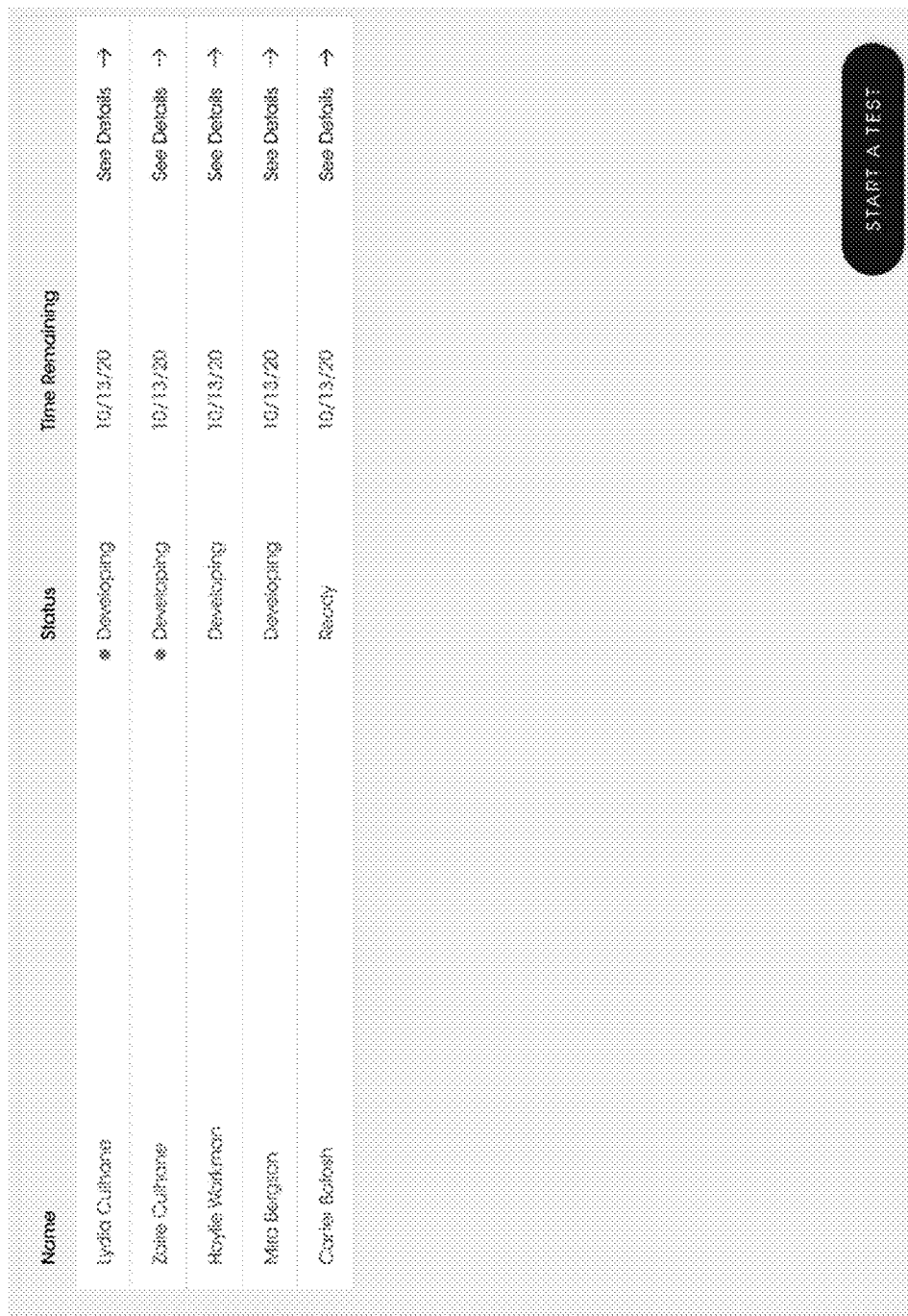
FIG. 21 illustrates an example multi-session management interface according to some embodiments described herein.

FIG. 21 illustrates an example multi-session management interface according to some embodiments provided herein. The multi-session management interface displays one or more pending test sessions, as well as their statuses. The sessions displayed in the multi-session management interface may comprise sessions of patients in a virtual waiting room or currently in a test session. As such, proctors, via the multi-session management interface, may manage pending test sessions and initiate new test sessions as patients and the proctor become available for testing. In some embodiments, the multi-session management interface may be general in that it shows test-ready patients for any test, location, or other parameter. However, in some embodiments, multi-session management interface may be specific to a specific medical test, a specific location, or to patients who speak a certain language, among others.

Figure 22:
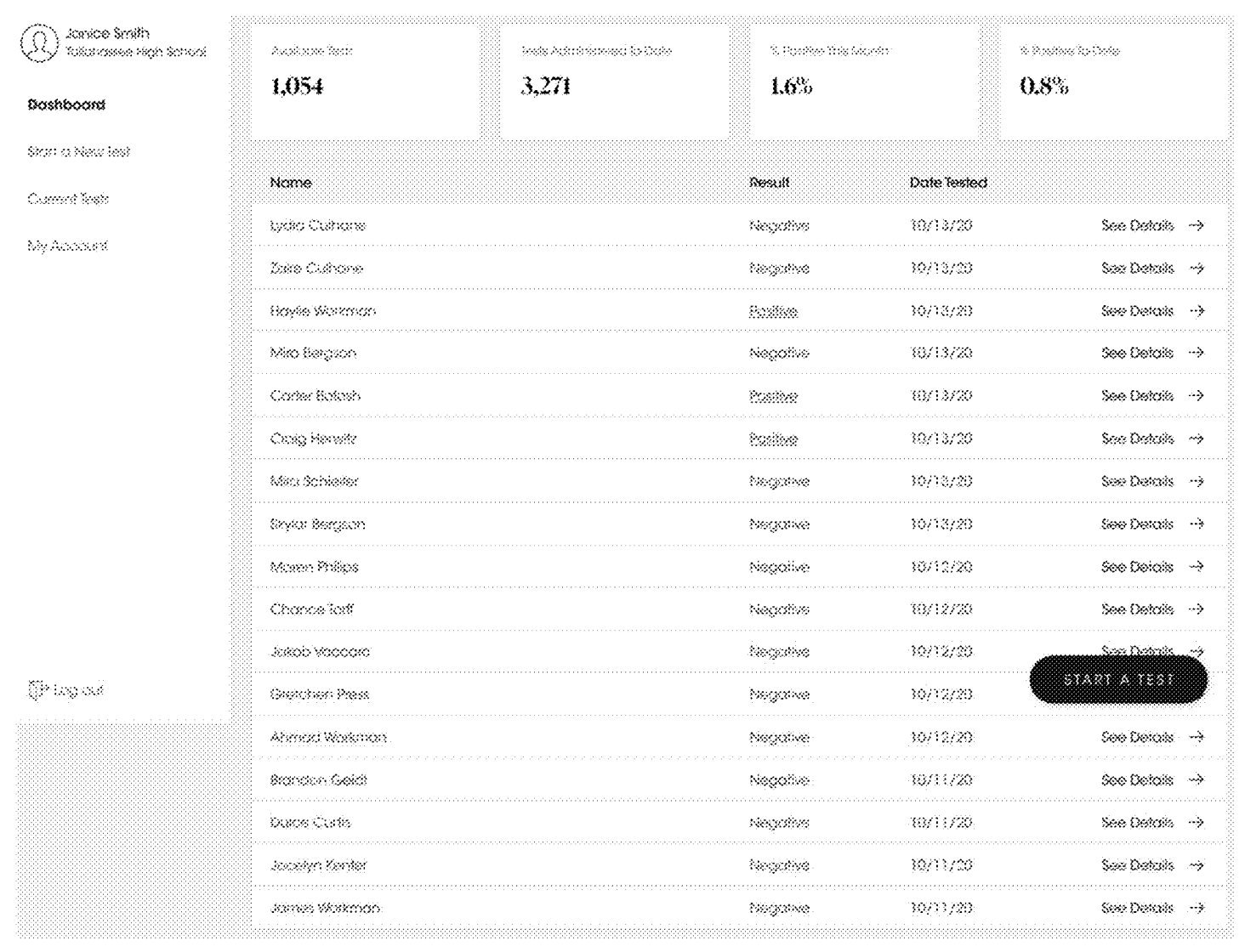

FIG. 22 illustrates an example testing dashboard interface according to some embodiments provided herein. In some embodiments, the testing dashboard interface displays a list of completed test sessions, including test results and other test details such as the date of test completion. In some embodiments, the testing dashboard interface may also comprise one or more test statistics, summarizing the test data for each specific proctor, test type, or test location, among other types of information. For example, the testing dashboard interface may comprise statistics regarding the remaining tests, the completed tests, test result data for a specific time, location, or demographic and overall test result data.

Figure 23:
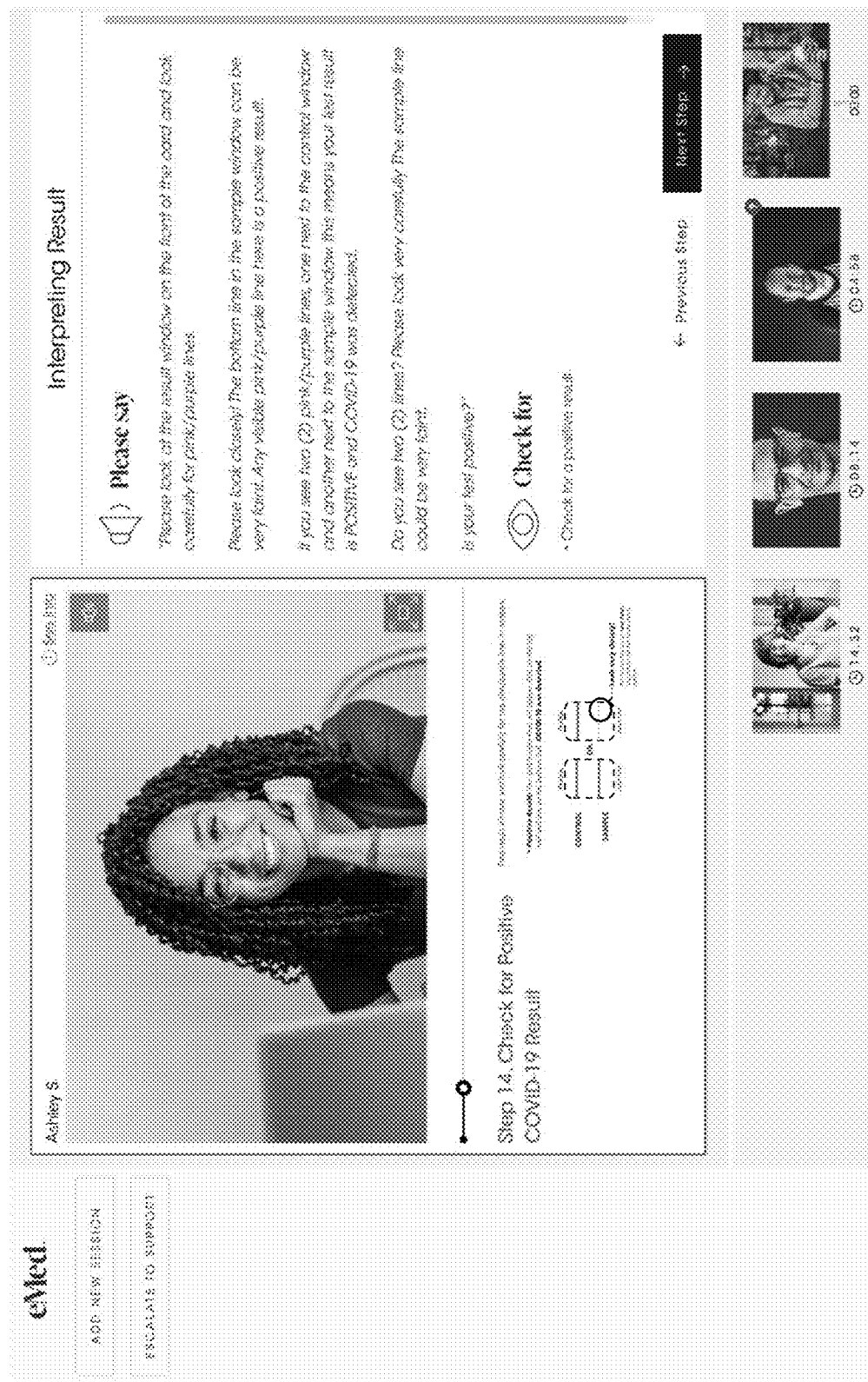
FIG. 23 illustrates an example multi-session testing interface according to some embodiments described herein.

FIG. 23 illustrates an example multi-session testing interface according to some embodiments provided herein. In some embodiments, the multi-session interfaces shown herein may be designed to manage a scenario where a proctor is managing more than one testing sessions simultaneously. In some embodiments, the multi-session interfaces may comprise multiple views that can be displayed, each view representing a one-to-one with a patient. As such, in some embodiments, the proctor is able to interface with a single patient at a point in time, but manage more than one patient testing sessions simultaneously, and switch between those sessions seamlessly. In some embodiments, the multi-session interfaces described herein may facilitate isolated audio/video sessions between multiple patients simultaneously through use of single-channel audio, on-screen session progress indicators, and proctor prompts.

In some embodiments, the multi-session testing interfaces described herein may allow for concurrency of about 2 to about 20 patient testing sessions for a single proctor. In some embodiments, the multi-session testing interfaces may comprise a workflow timeline that identifies patient testing progress for pending testing sessions, such that a proctor can immediately understand the progress of each pending session and switch between each isolated session as needed. For example, for some disease testing, there may be a testing cure time during which the patient and proctor are waiting for the test results. During this time, the multi-session testing interface may allow a proctor to switch an active session to another patient at a different point in the testing process such that multiple sessions can be managed simultaneously. The multi-session interfaces may introduce a supply line of isolated patient video sessions such that the patient sessions are stacked efficiently and proctor availability is maximized. In some embodiments, the multi-session interfaces may comprise a management tool that allows proctors to track the concurrent session timeline and to understand the upcoming timing requirements of each isolated session and the sessions collectively.

In some embodiments, each patient testing session enables a separate audio/video channel such that patients are isolated from each other and cannot hear or see other patient testing sessions, while the proctor may activate each individual patent testing session to communicate directly with each patient. Thus, the audio/video channels for each patient are segmented into separate feeds such that individual sessions are distinctly managed separately with separate session IDs and in such a way that none of the patients can talk to each other or are even aware that multiple sessions are occurring concurrently. In some embodiments, a proctor may activate a specific patient testing session through an activation mechanism on the proctor's screen, such as by selecting a patient video feed. The activation mechanism will open the audio and/or video channel with the specific patient for which the patient testing session has been chosen. This configuration minimizes the risk of exposing sensitive medical or personal data between patients; only the proctor may communicate with each patient. Furthermore, the multi-session interfaces described and shown herein facilitate efficient session switching through visual prompts that allow a proctor to understand the point at which each testing session is currently progressed.

In some embodiments, the multi-session interfaces may comprise individual patient mute mechanisms, which may close the communication channel with an individual testing session, as well as a global mute mechanism, which may close all communication channels between the proctor and all pending testing sessions. In some embodiments, only one patient testing communication channel may be opened at a time, such that a proctor may only communicate with a single patient at a single point in time. For example, opening a communication with one patient may automatically close (e.g., mute) a communication channel with all other patients to ensure that privacy between patients is maintained.

The multi-session interface of FIG. 23 illustrates a proctor view in which the screen is separated into a main session (e.g., the upper portion of the screen) and one or more secondary sessions (e.g., shown in a lower toolbar of the screen below the main session). In some embodiments, the proctor may have an open communication channel to the main session, while the secondary sessions remain muted. In some embodiments, the proctor may be enabled to exchange the main session with one of the secondary sessions by selecting one of the secondary sessions. Selecting one of the secondary sessions may cause display of that secondary session as the main session, and relegate the previous main session to the secondary session toolbar. In some embodiments, the multi-session interfaces may comprise one or more visual cues to indicate to the proctor the status of each patient session and to alert the proctor if attention is needed for any given session. For example, in the illustrated embodiment, such visual cues include an elapsed testing time for each patient, a countdown timer, and a question indicator.

Figure 24:
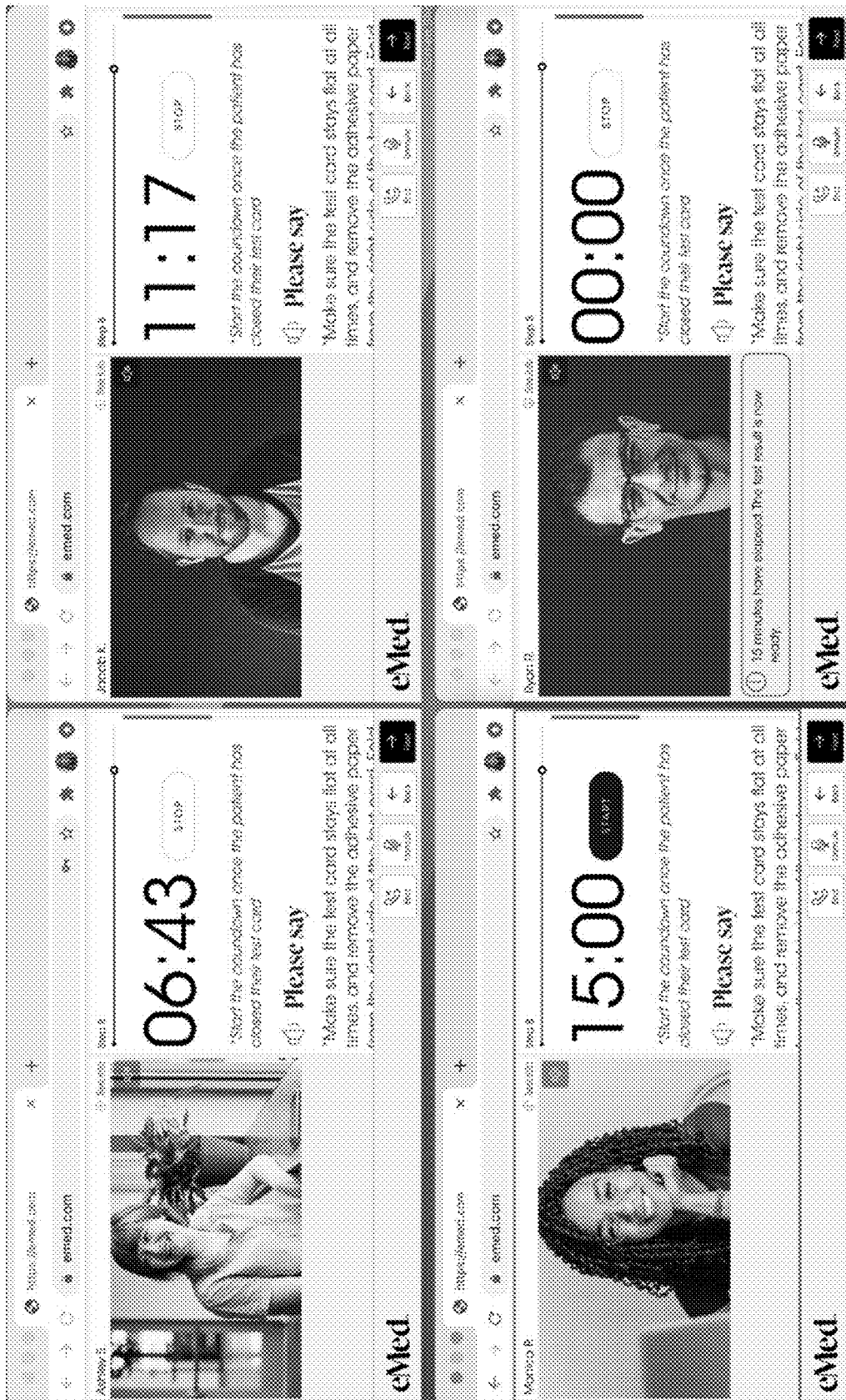
FIG. 24 illustrates another example multi-session testing interface according to some embodiments described herein.

FIG. 24 illustrates another example multi-session testing interface according to some embodiments provided herein. In some embodiments, a multi-session testing interface may comprise a multi-window interface, as shown in FIG. 24. In some embodiments, the multi-window interface may comprise one or more testing interfaces, such as that shown in FIG. 15A. However, in some embodiments, the multi-session testing interface may be enabled to track and manage multiple testing interfaces concurrently. As with the multi-session testing interface of FIG. 23, the interface may be segmented into separate feeds such that individual sessions are distinctly managed separately with separate session IDs and in such a way that none of the patients can talk to each other or are even aware that multiple sessions are occurring concurrently. For example, selecting one window of the one or more windows may open a secure communication channel with the patient of the selected window, and closing any other open communication channels. Also, each window may comprise one or more visual or auditory indicators of test status, such that a proctor can more easily manage the one or more patient test sessions occurring concurrently. In some embodiments, the multi-session testing interface may comprise individual testing sessions, each opened in a separate browser window.

Figure 25A:
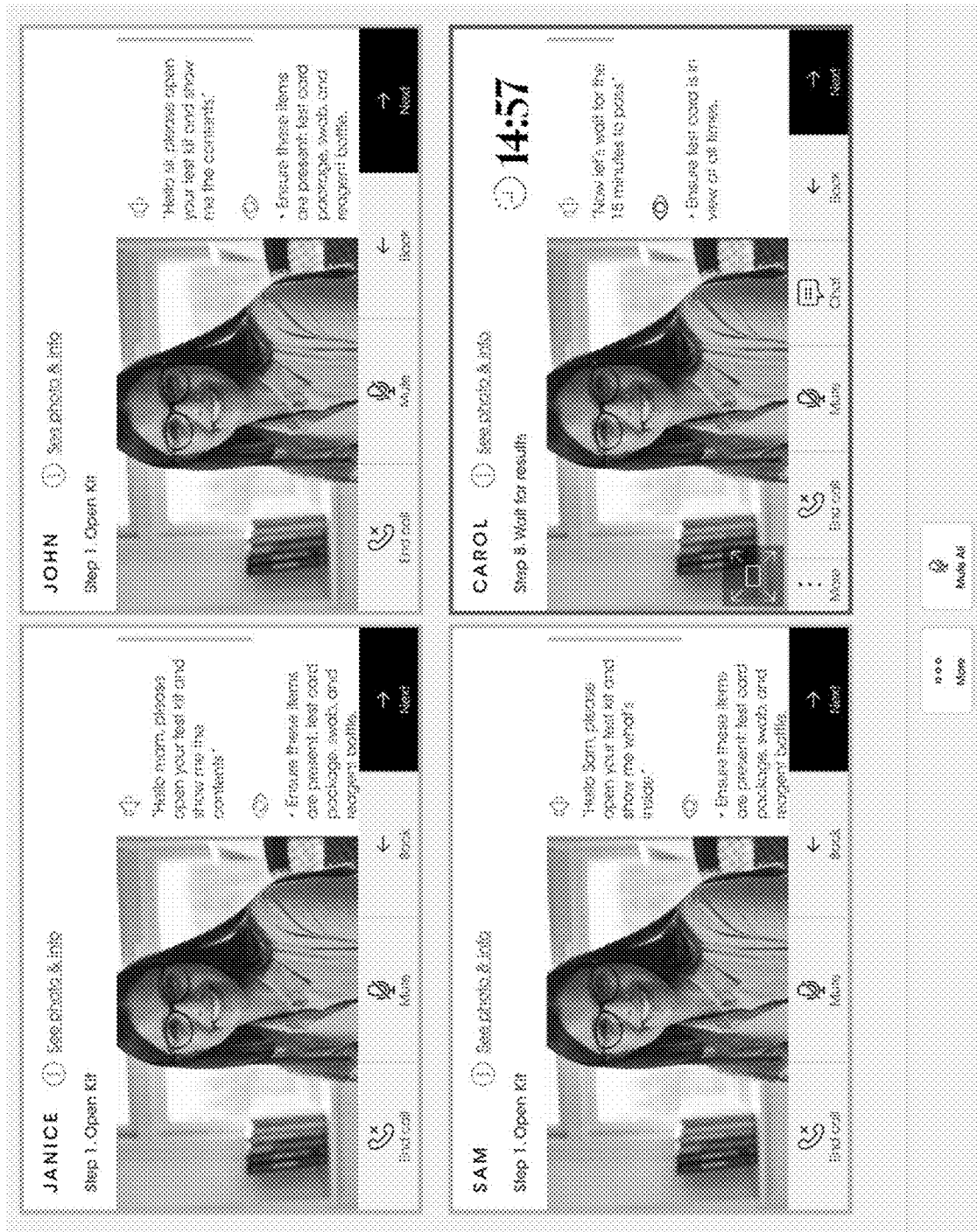
FIG. 25A illustrates another example multi-session testing interface according to some embodiments described herein.

FIG. 25A illustrates another example multi-session testing interface according to some embodiments provided herein. The multi-session testing interface of FIG. 25A may be functionally similar or identical to the interface of FIG. 24, except that the individual testing sessions may be displayed in a single browser window.

Figure 25B:
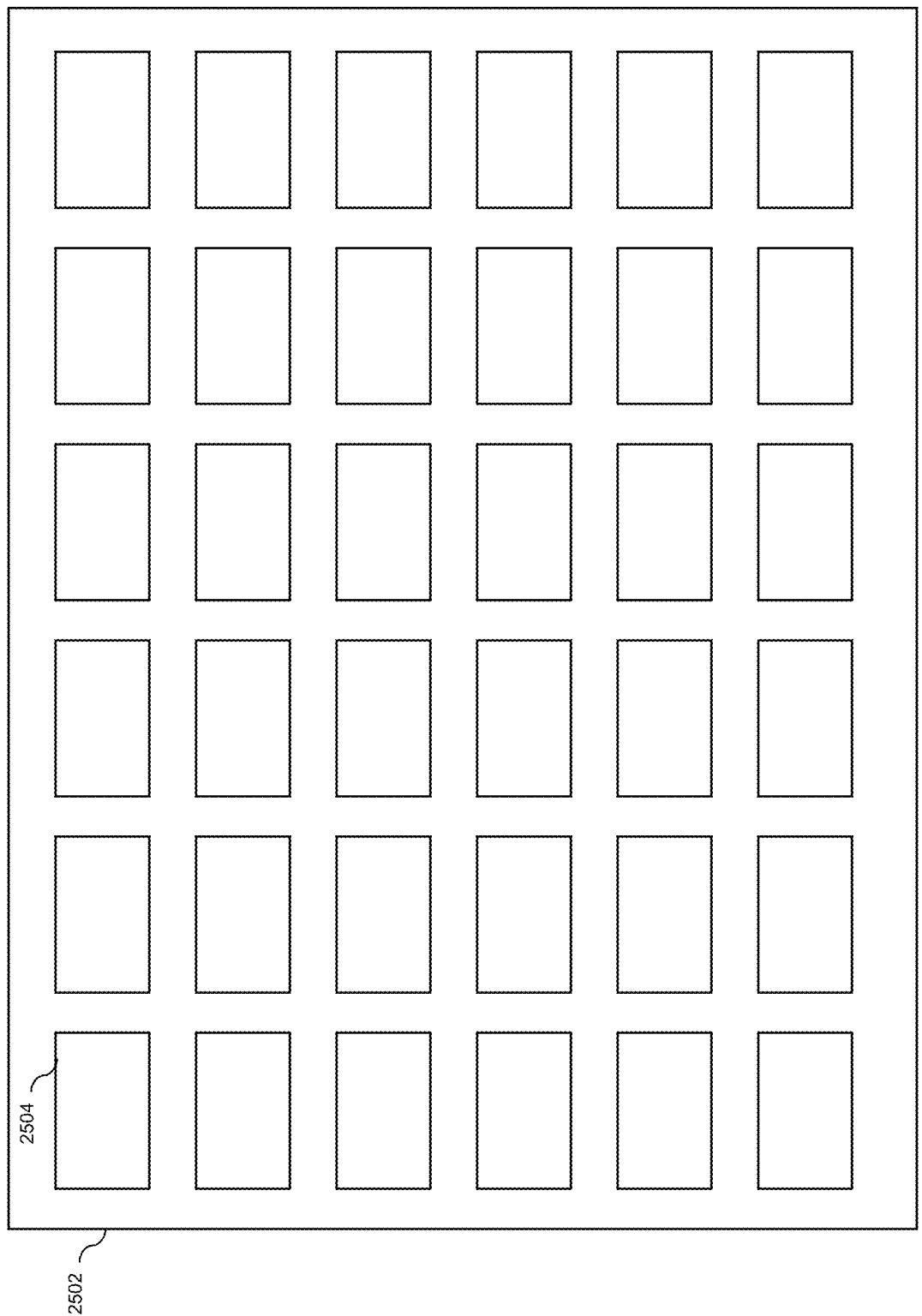
FIG. 25B illustrates another example multi-session testing interface according to some embodiments described herein.

FIG. 25B illustrates another example multi-session testing interface 2502 according to some embodiments. In some embodiments, the testing interface 2502 may comprise one or more patient video feeds 2504. In some embodiments, the patient video feeds 2504 may comprise individual concurrent testing sessions with individual patients. In some embodiments, the individual testing sessions may be automatically highlighted or manually selected by a proctor in order to interact with the patient subject of the highlighted session. In some embodiments, the highlighted session may also pop-out or otherwise enlarge relative to the other sessions, such that the proctor may access relevant information. In some embodiments, a proctor may use the interface 2502 to monitor a computer algorithm, which may be autonomously administering the tests to patients in patient video feeds 2504. In some embodiments, individual sessions may be highlighted by the algorithm for proctor intervention into the testing session. In some embodiments, the proctor may manually intervene in one or more testing sessions by selecting the desired patient video feed 2504.

Figure 25C:
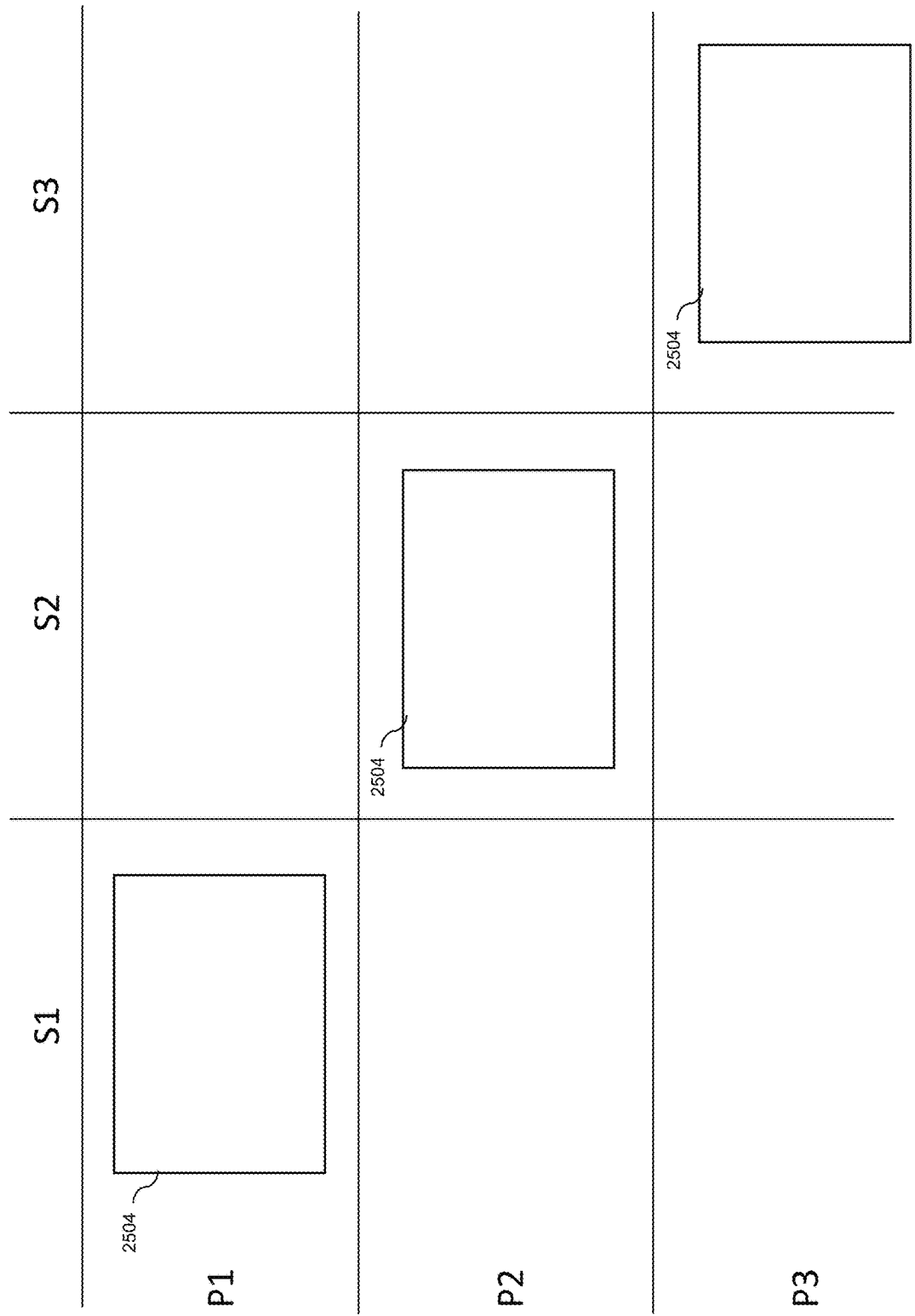
FIG. 25C illustrates another example multi-session testing interface according to some embodiments described herein.

FIG. 25C illustrates another example multi-session testing interface according to some embodiments herein. In some embodiments, the interface may comprise a timeline comprising one or more steps or stages $S_n$, wherein n is an integer representing the stage number in a sequence of stages comprising the test protocol. For example, the interface of FIG. 25C comprises S1, S2, and S3 representing three stages of a testing protocol. In some embodiments, the interface may comprise one or more patient video feeds 2504. The patient video feeds may be located within the interface in such a way as to indicate the testing stage at which the patient is currently undergoing. For example, in the illustrated embodiments, patient 1 (P1) is at stage 1 (S1), patient 2 (P2) is at stage 2 (S2), and patient 3 (P3) is at stage 3 (S3). In some embodiments, the testing interface may be utilized to allow a proctor to monitor one or more concurrent testing sessions. The testing interface may allow the proctor to easily understand the stage at which each testing session is currently undergoing. In some embodiments, the patient video feeds 2504 may change location upon completion of each testing stage, such that the interface is automatically and dynamically updated.

Expedited or Express Proctoring Platforms for At-Home Testing

The platforms and systems described throughout this application can provide a number of advantages relating to the administration and proctoring of at-home health testing and diagnostics. For one, such platforms and systems provide users with the option to perform health testing and diagnostics from the comfort of their own home or otherwise without having to travel to visit a healthcare professional in person. This in itself can provide a number of benefits including, saving time, increasing availability of testing, and decreasing the risk of exposure to and/or spread of an infection disease, among others.

An additional benefit that can be achieved using the platforms and systems described herein is that these can be optimized to provide for a high throughput of user tests, while at the same time minimizing the resources required to run the platform. For example, as described above, the platforms and systems described herein can be configured to allow a single proctor to proctor a plurality of user tests at once. This can provide advantages both for the platform and for the users. For example, the platform can facilitate testing using fewer proctors, thus leading to a reduction in operating costs. At the same time, the testing and diagnostics provided through the system and platforms described herein can still be readily available to a large number of users and wait times for entering a proctored test session can be reduced. Additional advantages achieved by some embodiments described herein may include reduction in costs associated with operating a testing platform (e.g., through a reduction in operating and/or oversight costs) and/or reduction in patient costs (e.g., by having them avoid unnecessary travel costs). Additionally, some embodiments may allow users to multitask while testing, thereby increasing flexibility for the users.

These and other benefits of the platforms and systems described throughout this application can be further achieved or even improved by, in some instances, offering certain users a more streamlined or express test session. As will be described in more detail below, such express test sessions can, for example, require less proctor involvement and/or decrease the duration of the test session for the user when compared with standard (e.g., non-express) test sessions. This can, in some instances, further increase the benefits and advantages associated with the systems and platforms for proctoring at-home health testing and diagnostics by further improving the user experience (e.g., by decreasing test session duration) and/or maximizing the availability and reach of the platform (e.g., by increasing the platform's ability to provide a high number of test sessions using fewer proctors).

Accordingly, in some instances, the platform can be configured to tailor a proctoring session to a user's level of test-taking experience. For example, users with less experience with the test and/or platform can be directed into a standard proctoring session, while users with more experience with the test and/or platform can be directed into an express proctoring session. As an even more specific example, users who are using the platform to take a test for the very first time ("first-time users") may be directed to the standard proctoring session (where, for example, a proctor provides full-fledged step-by-step instructions for taking the test), while users who have previously used the platform to take tests ("repeat users") may be given the option to either participate in (i) the standard proctoring experience, or (ii) an express or expedited proctoring session where the users take the test with reduced proctor participation/intervention.

As will be described in more detail below, various factors can be considered by the system in determining whether to offer or provide a user an express testing session. In some embodiments, the factors used by the systems disclosed herein to determine eligibility for express testing session can include one or more of the following: a test taker's past experience in taking such a test, a test taker's age, a test taker's language skills, a test taker's ability to follow instructions (for example, whether a system detects that the patient has completed certain initial tasks of the test within a certain period of time and/or completed certain initial tasks competently and/or with minimal supervision and/or within a minimum number of attempts, and in some embodiments, one or more of the foregoing factors can be used by the system to enable the system to provide real-time or substantially real-time grading of a user to determine eligibility of the user to take and/or be offered an express testing session), a test taker's computer literacy skills, a test taker's internet connection speed and/or connection quality/stability, a test taker's ability to have a physically present third-party to observe the test taker, an artificial intelligence algorithm used to observe the test taker's skills and/or ability to follow instructions and/or administering the test (for example, the use of artificial intelligence algorithms to determine whether the test taker has inserted a swab to a minimum instructed depth into a nasal cavity (or other orifice), and/or whether a test taker has completed a minimum number of rotations of the swab in the nasal cavity (or other orifice), or the like). In some embodiments, a factor in determining a test taker's eligibility for taking an express testing session can include but is not limited to whether the test taker has paid a necessary fee, and/or the number of other patients in a queue waiting to take a test, and/or the number of available proctors administering tests, and/or whether the test taker has a high priority flag setting in the users profile, and/or whether the user has a time commitment factor (for example, the user is about to board an airplane flight), and/or the location of the user, and/or the local time of a user, and/or whether a doctor has provided expedited instructions, and/or a test takers determined anxiety level, and/or the like. These factors can be selected so that a high degree of testing fidelity and accuracy is maintained. That is, the system may offer express testing sessions only to users for whom, upon consideration of one or more factors associated with the user, the system determines that there is a high probability of the user performing the test accurately with a reduced amount of supervision. At the same time, the system can be optimized such that express testing sessions are still reviewed by proctors and/or other components of the system to ensure sufficient testing accuracy.

Before considering eligibility factors and system requirements for ensuring testing accuracy, several aspects of an express testing session will now be described with the understanding that not each and every aspect need be present in all embodiments and that various modifications are also possible. In general, express testing session can allow a user to perform a test with reduced proctor involvement when compared to standard testing sessions. For example, during a standard testing session, a proctor may walk a user through each step of the process in great detail, including even mundane or simple steps such as opening and arranging the testing materials. By contrast, in some embodiments, during an express testing session, the user may be only engaged by the proctor, if at all, during more complex or critical steps of the test. During an express testing session, for example, a user may be allowed to perform various steps of the test and proctoring session with little-to-no proctor intervention. By decreasing proctor involvement, in some instances, testing duration may be decreased and/or testing capacity of the system can be increased.

In some embodiments, a script or prompts provided to a proctor (to be read to a test-taking user) may be different or customized based on the type of session being proctored. For example, a longer script or set if prompts may be provided for standard testing sessions, while a shorter script of set of prompts may be provided for express testing sessions. For example, in some embodiments, in an express testing session, the proctor may initially instruct the user to (i) perform the test and (ii) let the proctor know when the user is ready to submit their testing results (which may still ultimately be interpreted by the proctor). In this case, proctor engagement with the user is limiting to an initial instruction at the start of the session and verification of the testing result at the end of the testing session. Other levels of proctor involvement can also be provided in an express testing session. For example, in some embodiments, proctor engagement only begins when the user has completed the test and needs for the result to be verified. In these embodiments, proctor involvement may only occur at the end of the testing session. In some embodiments, even though proctor engagement may be limited, one or more proctors may still observe the user throughout the test (or during certain portions of the test) so as to be able to ensure that the test is performed properly and step in with corrective action or additional instructions if necessary.

As another example, proctor involvement can be required only for certain or critical testing steps. In the case of a nose swab, for example, during an express testing session, a proctor may be required to watch the swab occur so as to ensure that a sufficient swab depth is reached. In some embodiments, the user, during an express testing session, may be provided with written and/or prerecorded video or audio instructions and the proctor may only be involved with verifying that the steps are accurately followed. By contrast, in some embodiments of a standard testing session, a live proctor may read or walk a user through the instructions before watching them perform the steps. Decreasing proctor involvement with express testing sessions can increase proctor capacity and improve overall throughput and efficiency of the system, allowing proctors to focus more of their time on new or inexperienced users that are unfamiliar with the process, while allowing repeat or experienced users to perform certain steps on their own.

In some embodiments, during express testing sessions, a user may not be required to remain on camera for the entirety of the session. For example, the user may only be required to appear before the camera immediately before and after taking the test and/or during certain or critical testing steps. In some embodiments, the user may need to appear on camera prior to taking the test in order to verify their identity. In some embodiments, the user may need to appear on camera after taking the test to have the result verified by a proctor. In some embodiments, the user may need to appear on camera during certain or critical testing steps so that the system or a proctor can ensure that these steps are performed with sufficient accuracy. In some embodiments, during an express testing session, the entire session (or certain critical steps) can be recorded such that the testing session can be audited to ensure accuracy. Such auditing can be performed by a person (e.g., a proctor reviewing the video) or by the system (e.g., by using artificial intelligence or machine learning). In some embodiments, during an express testing session that is recorded, certain steps may be required to be viewed live by a proctor. These and other techniques which do not require a live or concurrent connection to the platform and/or a proctor at all steps of the testing session can be beneficial for several reasons. For example, this can permit reduction in power and/or bandwidth consumption. Additionally, these techniques can permit testing where network access is limited and/or unreliable.

In some embodiments, no live proctor interaction with the user may be required at all. This may not mean that no proctor is involved in the test. For example, a proctor may supervise (e.g., watch video of) express testing sessions without interacting with (e.g., speaking to) the user. In such cases, the proctor may only engage with the user when or if proctor engagement is requested by the user and/or if the proctor needs to intervene to ensure that the testing is performed accurately. By not requiring the proctor to interact with users unless interaction is determined to be necessary, a proctor may be able to supervise a higher number of testing procedures at once. This may also provide additional benefits such as widening the range of environments where testing could occur. For instance, if proctors no longer need to be spoken to or heard due to the express testing format, users can take tests more easily in noisy airports, or even at home, work, or other locations without interrupting or disturbing those around them. Additionally, as mentioned above, this can reduce a bandwidth requirement associated with testing, making testing more accessible by allowing more users to take tests on slower and/or less reliable networks, such as 4G or other slower connection speeds.

During express testing sessions, one or more proctors may be on standby to answer any questions that a user might have and provide general testing oversight. Proctors may step-in or otherwise intervene during an express testing session if they spot the user performing a step incorrectly or otherwise require additional information and/or participation from the user. As one example, a proctor may view a plurality of express testing sessions at once and only intervene with any particular user when necessary. In some embodiments, the proctor viewing the plurality of express testing sessions may not be the same proctor as the proctor that intervenes. For example, a proctoring monitoring a plurality of express testing sessions may realize that a certain user needs assistance and flag that user for intervention by another proctor. In some embodiments, an express session proctor may move a user from an express session to a standard session if it is determined that the user needs additional assistance. In some embodiments, an express session proctor may intervene and engage with an express session user directly, as needed, and maintain the user in the express session.

Determination of eligibility for participation in an express testing session can be determined, in some embodiments, using a score-based approach. A wide number of factors can be considered in determining a patient's express testing session eligibility score. For example, during a standard (or even an express) testing session, proctors may "rate" or otherwise provide an indication of their evaluation of a user's test-taking proficiency at the end of the proctoring session. Such ratings can be considered in determining whether future testing sessions of the user are eligible for participation in an express testing session. In some embodiments, proctor scores of user proficiency may be provided on a scale (e.g., a scale of 1-10, where one indicates that a user requires significant assistance and 10 indicates that a user requires little to no assistance, a star-rating system (e.g., 1-5 stars), etc.). In other embodiments, proctor scores of user proficiency may comprises a binary indicator of whether the user is proficient/competent or not. Each system (scale-based or binary) can provide advantages in certain scenarios. For example, a scale-based system may provide data granularity that may allow the system to make more nuanced determinations of eligibility, while the binary system may be simpler to implement for proctors.

In some embodiments, users may also provide an indication of their own proficiency and/or testing comfort upon completion of testing session (express or standard), using either a scale-based or binary system. Of course, care should be taken to ensure that users ratings of themselves are accurate. This can be achieved by, for example, comparing the user-provided score with the proctor-provided score. Alternatively or additionally, the platform may weigh the user's self-ratings against self-ratings of other users in order to calibrate and standardize self-ratings across the user-base. For example, if the user consistently rates themselves highly compared to other similar users (as determined by the system or other proctor-defined skill ratings), the system may adjust the user's self-ratings with a scaling factor to standardize self-ratings across the platform. In some embodiments, a user's self-ratings can also be compared against his or her own past self-ratings. For example, if a user that has an average self-rating of 5 after a number of past tests gives him or herself a self-rating of a 4 in a current test, the system may determine lower the user's express testing eligibility since the change represents a large deviation from past self-scores. This may occur even though a self-rating of 4 for another user, who consistently self-rates at 4, may remain eligible for express testing. Alternatively or additionally, this can be provided using machine learning and/or artificial intelligence by comparing the user-provided score against one or more additional factors determined by the system. Such factors could include for example, machine learning- or artificial intelligence-based analysis of a recorded video of patient's testing session, analysis of durations taken by the user in performing various steps, etc. In some embodiments, the user may be given the opportunity to formally (or informally) attest to the truthfulness and accuracy of their self-evaluation and/or agree to make a good faith effort to complete every test administered on the platform in accordance with the corresponding procedures, requirements, and guidelines.

Alternatively or additionally, a number of other factors could be used to determine the user's score for eligibility to participate in an express testing session. For example, the score could be determined based, at least in part, on a number of times the user has taken the test, how recently the user last took a test, etc. From this, it is apparent that express testing sessions would be beneficial for frequent testers. For example, a frequent traveler may take tests often, becoming very familiar with the process. On the other hand, users who seldom take tests or have not taken a test in a relatively long time may be less familiar with the process, and thus more likely to benefit from being reacquainted with the process by way of the standard testing session. Upon consideration of how many times, how frequently, and/or how recently (possibly in conjunction with proctor-provided and/or user-provided ratings and/or other factors), the system may determine that the user is eligible for participation in an express proctoring session.

In some embodiments, the score may also be determined based, at least in part, on an assessment of how similar a user's current testing environment is to the user's previous testing environment. In general, a user repeating a test in an environment in which they have previously taken the test or an environment similar to an environment in which they have previously taken a test, may be eligible for or receive in increased eligibility score for using an express testing session. To this end, in some embodiments, the user's eligibility score considers the user's IP address and/or GPS data to determine the user's location, which is compared against previous testing locations. Similarly, the type of user device the user is using may be identified and compared to the type of user device that the user has used previously. For example, a user who previously performed the test using a laptop, but is now attempting a test using a mobile phone, may not be eligible for express testing until they have qualified using a mobile phone.

In some embodiments, responses provided during a pre-qualification survey (such as the surveys described above) can also be considered in determining whether a user is eligible for an express testing session. For example, during a prequalification survey a user may verify that he or she is a healthcare professional that is competent to administer their own test. This may qualify the user for an express testing session.

A score for each user can be determined and associated with that user's account. If the score generated for the user exceeds a predetermined threshold at the time the user signs in and attempts to initiate a proctoring session, then the platform can give the user the option to enter an express testing session or to enter a standard testing session. The user's score can be continually updated based on subsequent testing experiences.

A user may, in some cases, be able to test in to establish eligibility for express testing sessions. For example, a user desirous of eligibility for express testing can elect to take a test to show that they are eligible for express testing. Such testing can involve a standard testing session or a modified testing session.

The systems and platforms for at-home health testing and diagnostics described herein can be configured to allow at-home testing for a wide variety of health and diagnostic tests. In some instances, a user score that establishes eligibility for express testing sessions can be specific to a certain test. In other instances, a user score that establishes eligibility for express testing can carry over to different types of tests available on the platform. For example, a user who has taken a nasal swab-based test several times and is eligible to use express testing session for that test may also be eligible to use an express testing session when taking a mouth swab-based test, even, in some cases, for the first time the user takes the mouth swab-based test. In other cases, the user may become eligible for express testing for new tests only after taking the new test using a standard testing session. Still, the user's score could decrease the requirement for the user to become express eligible for the new test. For example, the user (who has experience on the platform with a nose swab-based test) could become eligible to use an express testing session to take the mouth swab-based test after only taking said test once (whereas a user who has never used the platform may be required to successfully take the mouth swab-based test three times before becoming eligible for express testing sessions).

In some instances, however, in some examples, a same user may not enjoy the same eligibility reciprocity/recognition when trying a test that is radically different from the nasal swab-based test, such as a test where blood sample collection is required. For example, a user's express testing session eligibility score may be associated with a specific test (e.g., a nose-swab), a specific type of test (e.g., swab-based, whether nose or mouth, or minimally invasive tests), or with all tests available on the platform. In some embodiments, the user has the option whether to enter an express testing session or a standard testing session when taking a test, such that a qualified user has the opportunity to choose the most convenient and comfortable session for them.

In some cases, a user's express testing session eligibility can be revoked for testing infractions (e.g., performing one or more steps incorrectly, trying to rig the test, submitting fraudulent test results, etc.). This can be done to maintain the integrity of the platform as a whole. Accordingly, even in express testing sessions, it can be important to have a level of oversight and/or verification, which can be provided live (concurrent with the testing session) or after the fact (by, for example, reviewing recording, photos, or other data collected during the testing session). Moreover, the oversight and/or verification can be provided by live (e.g., proctor-based) or artificial intelligence- or machine learning-based review.

For implementations in which a score is generated for each user, a given user's score may be negatively impacted for testing infractions, which could lead to the user's express testing eligibility being revoked (e.g., as the score drops below a predetermined threshold value). More severe infractions can more negatively impact a user's score. Additionally or alternatively, a duration of the revocation could, in some examples, vary based on the severity or nature of the infraction, the user's history of infractions (e.g., a three strikes and you're out type policy), etc. As an example, a user who attempts to submit fraudulent test results may have their express testing eligibility (or even their standard testing eligibility) permanently revoked, while a user who forgets to wash their hands before taking a test may only have their express testing eligibility temporarily suspended (e.g., the user may be required to participate in the standard proctoring session the next time they take a test using the platform, but may regain eligibility immediately thereafter). In some instances, the user may be notified of the reasons associated with loss of express eligibility (or a decrease in their user score) and given opportunities to remediate the cause of the infractions. For implementations in which a score is generated for each user, the extent to which a user's score is negatively impacted by testing infractions may vary based on such factors as type and severity of the infraction.

In some embodiments, users who are already established as eligible for express session testing may be required to participate in the standard proctoring session periodically, even in cases where no testing infractions have incurred. For example, users that would otherwise be eligible for express testing session may be required to participate in the standard proctoring session the next time they take a test using the platform if, for example, the test kit has changed since the last time they took the test (e.g., the packaging has changed, the shape/design of items in the test kit have changed, etc.). As another example, users that would otherwise be eligible for express testing session may be required to participate in the standard proctoring session the next time they take a test using the platform if the testing procedure and/or FDA requirements have changed since the last time they took the test (e.g., users were previously required to add six drops of reagent solution to a test strip, but are now required to add eight drops of reagent to the test strip for enhanced accuracy). As another example, users that would otherwise be eligible for express testing session may be required to participate in the standard proctoring session the next time they take a test using the platform if the proctoring session protocols have changed since the last time they took the test (e.g., users were previously asked to hold the testing materials up to the camera on their laptop to show the proctor their results, but are now required to instead leave the testing materials on the table, snap a photo of the testing materials on their smartphone, and submit the photo to the proctor through a downloaded or web-based version of an application on their smartphone).

Additionally or alternatively, users that would otherwise be eligible for express testing session may be required to participate in the standard proctoring session periodically or randomly to ensure eligibility for express testing.

Although generally having been described as a binary system of express testing sessions and standardized testing sessions, this need not be the case in all embodiments. For example, express testing may involve modification or expedition or one or more of the steps of a standardized testing session. That is, in some embodiments, hybrid testing sessions may be provided that are tailored to the user's level of test-taking experience on a step-by-step basis. Referring once again to the example described above in which users were previously required to add six drops of reagent solution to a test strip, but are now required to add eight drops of reagent to the test strip for enhanced accuracy, in some embodiments, the proctor may only provide the "standard" proctoring experience for the step of the test in which the user is required to add the reagent solution to the test strip, and may otherwise provide an express proctoring experience for the other steps of the test (which have not changed). As another example, an express testing experience can be provided for simpler steps, while a standard, more involved testing experience can be provided for more complex or critical steps. In some embodiments in which an express testing session includes both steps that are not and steps that are directly monitored by a live proctor, the system may be configured to provide a cue (e.g., a visual or audio cue) to identify or distinguish between these steps. For example, when a user arrives at a step that requires proctor involvement, the user may be alerted (via the cue) to wait for proctor engagement.

In some embodiments, a user that has qualified for express testing may be given a "badge" or other indicator that appears next to their username when they become eligible for express testing sessions. In some cases, one set of proctors give standard testing sessions and another set of proctors give express testing sessions. In other cases, proctors may give both standard and express testing sessions simultaneously. In these cases, a badge or visual indicator may help visually distinguish express users from standard users. Additionally, in some embodiments, upon qualification for express testing (or upon disqualification), the user is notified of the change in status. Such notification can occur, for example, during a testing session, after a testing session, or at the start of a subsequent testing session.

FIG. 26 illustrates an example flowchart for providing standard testing sessions and express testing sessions according to some embodiments described herein. At 2602, a testing session is initiated. Initiation of the testing session can be begun by a user, for example, when a user creates or logs into their user account and selects to initiate a test. At 2604, the system, platform, or a proctor may make a determination of the user's eligibility for participation in an express testing session. As described above, this determination may be based on a number of factors using a score-based approach. For example, in some embodiments, one or more scores generated for the user may be evaluated against one or more thresholds to determine the user's eligibility at 2604. If it is determined that the user is eligible for participating in an express testing session, at 2606, the user is presented with options to participate in either an express testing session or a standard testing session. In some embodiments, this step can be omitted and the user can be taken to an express testing session upon determination of qualification. If the user elects to participate in an express testing session, at 2608, the user is provided an express testing session. As described above, in certain scenarios, the user may be removed from an express testing session, for example, if it is determined that more direct proctor supervision is needed (either by the system, a proctor, or the system). In such cases, as indicated by the arrow extending between 2608 and 2610, the user may transition from an express testing session to a standard testing session midtest. As noted above, such express testing session, may involve less, little, or no proctor engagement or involvement when compared with a standard testing session. If the user that has been determined to be eligible for express testing elects to proceed with a standard testing session, at 2610, the user is provided with a standard testing session. Returning to 2604, if it is determined that the user is not eligible for participation in an express testing session, at 2610, the user is provided with a standard testing session. From 2608 (an express testing session) or 2610 (a standard testing session), during or upon completion of the testing session the user is evaluated and/or verified at 2612. Evaluation or verification may provide data that can be used to determine future eligibility for express testing. At 2614, such data can be saved for future use, such that it can be used at 2604 when a subsequent test is initiated to determine eligibility for express testing.

User-Proctor Matching

As described previously, the testing platform described herein can be configured to allow for a plurality of users to perform remote health and diagnostic testing under the supervision of one or more proctors. As users access the platform, they can be matched with certain proctors based on various criteria selected to improve the users' testing experience and/or to improve the efficacy of the proctors. In some embodiments, users accessing the platform are placed in a user pool and proctors accessing the platform are placed in a proctor pool. Various criteria can be determined for each of the users and for each of the proctors. These criteria can then be analyzed to match or assign users to certain proctors. For example, such criteria can be evaluated at 116 of FIG. 1 and/or at 308 of FIG. 3 (described above) in order to match or assign users to proctors.

Users may be matched with or assigned to proctors based at least in part on one or more of a variety of different factors. Such factors may include, for example, the languages spoken by the users and the proctors, user disabilities and/or special needs, user and proctor location, types of tests to be taken or administered, a user's level of technical proficiency, proctor availability, strength of network connection, and/or a level of testing, verification, or scrutiny desired or required.

For example, users may be matched or assigned to a proctor based on a language spoken by the user. The testing platform may be provided in multiple languages and available all over the world. Accordingly, users accessing the platform may speak a variety of different languages. To facilitate testing, proctors may be provided in languages that correspond to the languages of the user. When an English-speaking user accesses the platform, they may be assigned to an English-speaking proctor. When a Spanish speaking user accesses the platform, they may be assigned to a Spanish speaking proctor. This can ensure that the proctored testing session can run as smoothly as possible as communication barriers between the users and the proctors can be reduced.

In some embodiments, the language desired by the user for the proctored testing session may be indicated by the user. For example, when accessing the platform, the user may create a user profile in which the user's language preference is indicated. In some embodiments, multi-lingual users may indicate that they can speak more than one language and may even indicate a proficiency for each language. When matching such users to proctors, each language and proficiency may be evaluated in view of the available proctors in order to find a matching proctor as quickly as possible. For example, if a user indicates that he or she is a native Spanish speaker but is also fluent in English, the platform may first check to see whether a Spanish speaking proctor is available. If a Spanish speaking proctor is available, the user may be matched to the proctor. If a Spanish speaking proctor is not available, the platform may then check whether an English-speaking proctor is available, and if so, match the user with the English-speaking proctor.

In some embodiments, the platform may attempt to automatically determine the user's language. For example, the platform may analyze the user's network connection (e.g., the user's IP address) in an effort to determine where the user is geographically located. If, for example, the user's IP address is associated with a typically English-speaking geographical location, the user may be initially presented with an English-speaking proctor. If the user's IP address is associated with a typically Spanish speaking geographical location, the user may be initially presented with a Spanish speaking proctor. Other factors may also be analyzed in an effort to automatically determine the user's language. For example, an estimate of the user's language may be made based on a top-level domain associated with the testing platform's website accessed by the user. For example, if a user accesses the testing platform at www.[testingplatform].mx (.mx being the top-level domain associated with Mexico), the testing platform may make an initial determination that the user likely speaks Spanish. In such cases where the platform attempts to automatically determine the user's language, the user may be given the option to change to a more preferred language in the event that the automatically determined language is incorrect.

Proctors may also be associated with profiles that provide information about the proctors that is used to match the proctors to the users. A proctor profile can include information about which languages are spoken by each proctor as well as a proficiency score for each language. In some embodiments, proctors can specify which languages they speak as well as their proficiency in each language. In some embodiments, proctors may be required to take language tests to ensure that they are sufficiently proficient to provide a proctored test in a given language. In some embodiments, the platform may analyze proctor performance and adjust a proctors proficiency score for each spoken language. For example, a proctor may indicate that he or she is fluent in English and Spanish. The platform may thus assign both English speaking users and Spanish speaking users to the proctor. The platform may analyze the proctor's proficiency in providing proctored testing sessions in English and Spanish. For example, the platform may track an average testing session length for both the English and Spanish sessions. Upon determination that the proctor takes sufficiently longer to provide a proctored testing session in one language when compared to the other, the platform may lower the user's proficiency score for the slower session language. Additionally or alternatively, the platform may evaluate testing accuracy for each of the proctor's spoken languages. For example, if it is determined that tests administered by the proctor in Spanish generally are more accurate than tests administered by the proctor in English, the platform may assign more Spanish speaking users to the proctor. As a result, the platform may assign more users who speak the proctor's faster language to the proctor in the future. In some embodiments, in addition to or in place of comparing the proctor's proficiency against itself (e.g., comparing the proctor's English proficiency against his or her Spanish proficiency), the platform may also compare the proctor's proficiency against that of other proctors. In this way, the platform can dynamically balance matching users to proctors in the most efficient manner.

Another factor that may be considered by the platform in matching or assigning users to proctors can be disabilities or special needs of the users. For various reasons, some users may require special accommodations in order to take a test. The platform can consider the users' needs and provide the user with a proctor equipped to provide the necessary accommodations. As one example, a user that is hard of hearing or deaf can be assigned to a proctor that is proficient in sign language or to a proctor that is proficient in communicated with the user through text. Users accessing the platform may provide information about any special needs or disabilities as well as desired or necessary accommodations that must be made to facilitate the testing session. For example, such information can be entered during creation of the user's profile or account or gathered during a pre-qualification survey, for example as described at 104 and 106 of FIG. 1. Similarly, proctor profiles can store information about skills or accommodations that a proctor can provide. Similar to the proctor language information described above, a proctor's ability to accommodate a disability or special need can be evaluated by the platform. For example, testing session duration and/or accuracy of test results can be analyzed and used to rebalance proctor assignment over time such that that proctors can be assigned and matched to users in a manner that maximizes the overall efficiency of the system.

In some embodiments, the platform may match users to proctors based on the location and/or time zone of the users and proctors. This may improve the testing experience by matching users to proctors that are close to them geographically or in the same time zone.

In some embodiments, proctors and users can be matched based on the type of test to be taken. As noted above, the platform may be configured to allow for a wide variety of remote health tests or other diagnostics. While users accessing the platform may generally do so in order to take a specific kind of test, proctors may be able to administer more than one type of test. For example, a proctor may be able to provide a proctored testing session for a first type of test and also to provide a proctored testing session for a second type of test. Proctor profiles may include a list of each type of proctored testing session that can be provided by a given proctor. In some embodiments, proctors may need to take specific training and/or receive certain verifications to provide different types of proctored testing sessions.

In some embodiments, proctors that are certified or otherwise able to provide different types of proctored testing sessions can be evaluated by the platform such that users are assigned to the proctor in an efficient manner. For example, if both a proctor A and a proctor B are capable of administering a first type of proctored testing session and a second type of proctored testing session, the platform may evaluate proctor A and B's proficiency with each type of testing session and match users accordingly. For example, the platform may determine that proctor A provides the first type of proctored testing session more quickly than proctor B does. The platform may then assign users taking a test associated with the first type of proctored testing session to proctor A and assign users taking a test associated with the second type of proctored testing session to proctor B.

Another factor that can be considered by the platform in assigning users to proctors may be the users' technical ability or proficiency. As an example, an older user may not be as technically proficient as a younger user. Certain proctors may have more proficiency in providing proctored testing sessions to such older users. Accordingly, the platform may assign such older users to such proctors. In some embodiments, the users themselves may provide an indication of their technical proficiency. For example, during user account creation or a pre-qualification survey, the user may input a technical proficiency score or a comfort score associated with using the remote testing platform. In some embodiments, the platform may make a determination about a user's technical proficiency based factors observable by the system. For example, the system may make a determination about a user's technical proficiency based on an amount of time take by the user to set up his or her account or to complete the pre-qualification survey. As another example, the platform may make a determination about the user's technical proficiency based on the user's age or other factors. In some embodiments, the system may automatically administer a short test to the user to determine technical proficiency, for example, by checking whether the user is able to operate his or her webcam, microphone, and speakers.

As before, the platform may continually or periodically evaluate proctor proficiency in providing proctored testing sessions to less technically proficient users. For example, the platform may analyze elapsed session times or test result accuracy for various proctors and assign less technically proficient users to proctors that can most efficiently and accurately administer tests to such users.

The platform may also consider the strength of users' and proctors' network connections in determining how to assign and match the users and proctors. For example, the platform may evaluate or determine an internet speed, latency, and/or reliability of the network connection for each user and proctor. This information can be used to match proctors and users in a manner that ensures that a stable connection between a user and proctor can be maintained during a testing session.

In some embodiments, the platform may also consider a level of testing verification or scrutiny that is required or desired in determining how to assign and match users to proctors. For example, in some instances, a certain level of proctor scrutiny or involvement may be required to complete and validate a test result. For example, government or other regulatory bodies may require certain steps to be completed in order to validate a test. In such cases, users can be matched with proctors that are capable of providing the needed level or scrutiny. In other example, users may request a certain level or proctor involvement or scrutiny. For example, a user that is generally unsure or uncomfortable with remote testing procedures may request a more involved proctoring session.

Accordingly, users who require or desire a proctoring session with additional verification measures or a higher level of testing scrutiny may be matched with proctors who conduct one-on-one proctoring sessions and/or can provide additional verification services. As one example, users who need verified passes in order to comply with CDC rules or laws may be matched with proctors capable of providing such services. As another example, in some embodiments, users may pay for a premium membership/service for the platform that automatically communicates the users' test results to user-specified entities. For example, the platform can provide users with a with a TSA Pre-Check-like pass service where the user provides additional verification information and performs additional verification processes with the proctor in exchange for a pass that allows users to "skip the line" or otherwise more seamlessly travel or access various venues and other locations.

The system may also consider proctor availability in matching users and proctors. As noted above, the platform may consider various factors in matching users and proctors to improve the efficiency and accuracy of the platform. In some embodiments, however, the most efficient proctors may not be available. Accordingly, the platform can further consider proctor availability. For example, in some embodiments, it may be faster to assign a user to a less proficient proctor with a shorter wait time, rather than assigning the user to more proficient proctor with a longer wait time.

The platform may dynamically match proctors and users upon consideration of one or more of the factors described above as well as others. Further, the platform may continually or periodically evaluate the efficiency and accuracy of proctors based on each of these factors and use this information to continually rebalance and recalibrate the platform to maximize efficiency. For example, the platform may adjust how users are assigned to proctors to reduce testing session times and/or improve testing session accuracy by assigning proctors to users in the most efficient manner.

Additionally, the order in which users are placed in queues for meeting with proctors may be determined based at least in part on one or more of a variety of factors. As noted above, in some instances, a user may be placed into a waiting room while waiting for a proctor to be assigned or while waiting for an assigned proctor to become available (see, for example, FIG. 9, which is described above). The order in which users are matched to proctors and/or assigned to available proctors may also be considered by the system. For example, in some embodiments, a level of testing urgency or priority associated with each of the various users that are to meet with proctors may be considered. The level of testing urgency or priority that is associated with a given user may be a function of one or more of a variety of parameters. These factors may include, for example, how soon the user will be boarding a flight, whether the user is crossing a state or international boarder, how at-risk the user may be, how symptomatic the user may be, the user's current test pass status, the user's occupation or other status, the time spent waiting in queue, and/or a user's membership tier associated with the user platform, among others.

For example, a user that is about to board a flight or travel across state lines or other boarders may be given an advantageous place in the queue in an effort to assure that the travel can be completed. As another example, a more at-risk user may be given an advantageous place in the queue to minimize his or wait time. An at-risk user may be one that has a pre-existing condition or is elderly. For example, the elderly and people with certain health conditions may be placed ahead of others in the queue in order to ensure that they can be tested as soon as possible. As another example, a more symptomatic user may be given an advantageous place in the queue. People who are exhibiting worrisome symptoms may be placed ahead of others in the queue so that they can receive the medical attention they might need sooner. This can improve health outcomes for the particular patient as well as minimize the spread of a contagious disease to others.

A user's place in queue may be assigned in part based upon whether or not the user has a test pass that is currently valid and/or the amount of time remaining until expiration of a user's current test pass. For example, people who do not have test passes that are currently valid and people who have test passes that will be expiring shortly may be placed ahead of others in the queue. The user's occupation or other status may also be considered in determining queue placement. For example, doctors or medical personnel may be placed ahead of others in the queue. Additionally, time spent waiting in queue may also be considered. For example, users who have not been waiting for very long may be placed behind users in the queue who have been waiting for a while. In some embodiments, the platform may provide premium memberships or services that can affect a user's placement in the queue. For example, users that pay for a premium membership or service may be placed ahead of others in the queue.

The user-proctor matching and user queuing techniques and features described above have generally been presented in the context of assigning users to proctors for proctored based testing sessions. However, in some embodiments, different proctors may be provided for different portions of a proctored testing session. Accordingly, the user-proctor matching and user queuing techniques and features described above can be implemented at different stages in proctored testing session along the process. For example, a user may be shifted to different proctors throughout a test, with different proctors providing different stages or steps in the process. Proctors can be evaluated for proficiency and accuracy in providing the different stages of the tests (in some embodiments, for different types of users), and users and proctors can be matched accordingly.

In some embodiments, some phases or steps in a testing process may require more direct supervision, while other stages may require less supervision. In some embodiments, during stages that require more direct supervision a lower ratio of proctors to users may be used, while in stages that require less supervision a higher ratio or proctors to users may be used. Proctors can be evaluated to determine whether they are more proficient in proctoring the steps that involve supervision of a higher number of users or in proctoring the steps that involve supervision of a lower number of users, and the platform may match users and proctors accordingly.

Figure 27:
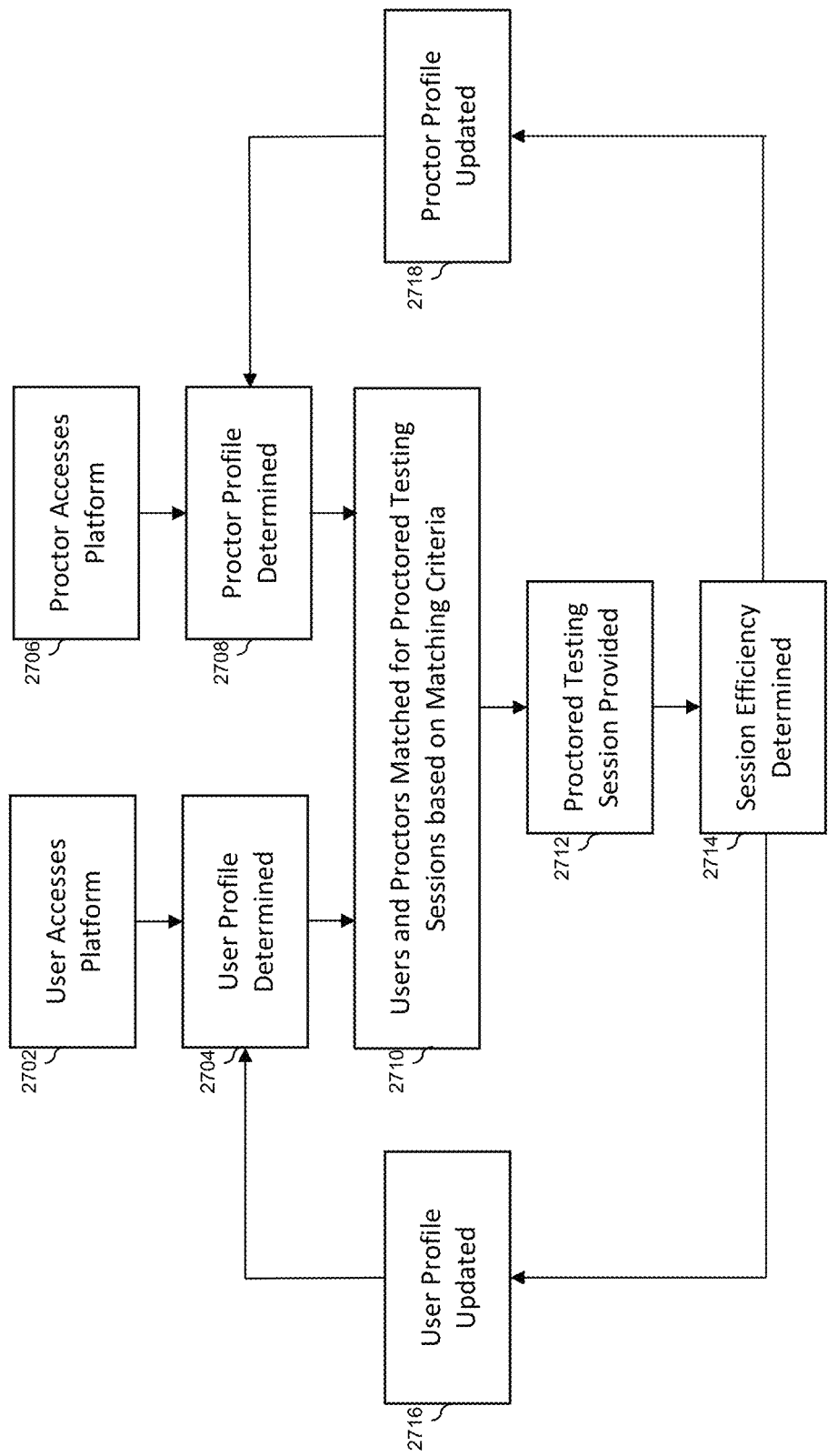
FIG. 27 illustrates an example flowchart for user-proctor matching and assignment according to some embodiments described herein.

FIG. 27 provides a flowchart of an example process that can be implemented in the platform for matching users to proctors and improving the efficiency and accuracy of the platform. As shown in FIG. 27, at 2702, a user accesses the platform. The user may access the platform remotely over a network using a user device as described above. At 2704, information regarding the user may be determined and stored in a profile associated with the user. User information may be determined, for example, during an account creation or pre-qualification survey step in which the user responds to one or more prompts to provide information about the user. In some embodiments, the platform may determine information about the user based on information available to the platform, such as information about the user's network connection. Information about the user may include, for example, information about languages spoken, disabilities or accommodations needed or requested, location and/or time zone, type of test to be taken, an assessment of the user's technical proficiency, information about the user's network connection (e.g., speed, latency, reliability, etc.), and/or a desired or required level of testing scrutiny, among other types of information.

At 2706, proctors access the platform. The proctors may access the platform remotely over a network using a proctor device as described above. At 2708, information regarding the proctor may be determined and stored in a profile associated with the proctor. In some embodiments, proctor profile information is input by the proctor. In some embodiments, proctor profile information is determined by the platform, for example, based on previous proctored testing sessions provided by the proctor. In some embodiments, the information about the proctor may include, for example, information about languages spoken, disability accommodations the proctor can provide, location and/or time zone, types of test to be administered, and/or information about the proctor's network connection (e.g., speed, latency, reliability, etc.), among other types of information.

At 2710, users and proctors are matched for proctored testing sessions based on an analysis of one or more matching criteria by the platform. For example, the platform may consider the information stored in the user and proctor profiles and match users to proctors in a manner that maximizes the efficiency of the system as described above. At 2712, a proctored testing session is provided to the user based on the matching established at 2710. At 2714, the efficiency and/or accuracy of the proctored testing session can be analyzed by the platform and used to update the user profile, at 2716, and/or the proctor profile at 2718. For example, if the testing session takes longer than expected or desired, the proctor profile may be updated such that the proctor will not be matched with that type of user in the future. In this way, the platform can continually evaluate proctors and users and match them in a manner that maximizes the efficiency of the system.

Test Integrity and Verification

In some embodiments, during a remote testing procedure, various steps can be implemented before, during, and after the test in order to ensure test integrity and verify the result of the test. For example, before the test is taken, it can be desirable to verify the user's identify and to verify that the test kit is valid (e.g., to verify that the test kit is one that has been purchased or otherwise obtained through an official channel, has not expired, and has not been previously used). During the test, it can be desirable to verify that any sample obtained is actually obtained from the previously verified user and that all test instructions and procedures are followed correctly. Finally, after the test, it can be desirable to ensure that the test result is obtained from the previously verified test kit and to ensure that the test result is interpreted correctly.

As noted above, it can be important to verify the user's identity before the test is taken. This can be because it ensures that the results will be attributed to the correct person. Verifying the user's identity is particularly important in cases of remote testing as the person being tested is not physically located with the person administering the test. Thus, in many situations, extra precaution may be advantageously taken to correctly identify the user's identity. Verification of the user's identity can be accomplished in several ways. For example, the user can be asked to upload a copy of an official identification (e.g., a driver's license or passport) as part of an account creation or pre-qualification step. In some embodiments, the user may be asked to show the official identification to the proctor during the testing session. During the testing session, the proctor can then compare the uploaded or shown identification to the person's appearance in the video feed. In this way the proctor can verify the user's identity by comparing a live (or other) video feed of the user to an identification card associated with the user. In some embodiments, once the user's identity is verified, the user's identity can be associated with the user's account for future tests. For example, after verification, future verifications may be automated with face matching technology.

In another example, user identification can be achieved using biometrics. For example, in some embodiments, a user accessing the platform may be given the option to perform a biometric initialization, in which the user goes to a physical location where their fingerprint or a unique segment of DNA can be sampled and stored. Thereafter, every test taken can sample their fingerprint or DNA to verify identity. This may also be automated. In other embodiments, biometrics may be performed using biometric features of the user's device. For example, many smartphones today are capable of taking a user's fingerprint or recognizing a user's face. These features may be used to verify the user's identity in some embodiments.

In addition to verifying the user's identity, the test or test kit that will be used during the test may be verified as well. This can be important because it ensures that the test results are scientifically valid and can be trusted. Again, this can be particularly important in the case of remote testing where the user is not physically located with the person administering the test. In one embodiment, the test or test kit can be provided with a unique ID (e.g., a UID or serial number) assigned during manufacture, which can be queried when the test is taken. This can take the form of a printed string of characters, barcode/QR code, NFC/RFID tag, or other. This code may either explicitly encode information associated with the test (such as a test identifier, test expiration date, batch/lot codes, indication of whether this number has been used for a test or not) or it may encode a link to a database entry that includes such information. Prior to beginning the test, the code may be scanned to verify the test kit. If anything is amiss, the test does not proceed and the user may be instructed to obtain a new test kit. In some embodiments, it may be preferable to provide the unique ID in a non-human readable manner. This may provide an advantage in that they are harder to misrepresent. A visible code could be duplicated and used on an expired test, for example.

During a test, a sample may be collected from the user, for example, using the test kit. To ensure the integrity of the test, steps may be taken to ensure that the sample is actually collected from the same user whose identity was verified before beginning the test. Again, this can be especially important in the case of remote tests since the user is not physically located with the person administering the test. It can be important to ensure that a user does not swap in a sample obtained from another user when performing the test. Various mechanisms for verifying that the sample is collected from the previously verified user are possible. For example, during a proctored testing session, the proctor (or an automated system) can observe the sample collection process. For example, in the case of a nasal swab test, the proctor or the automated system can observe the user performing the swab procedure. Such observation can be performed live (e.g., over a live video connection) or through a pre-recorded video. In either event, it may be important that all sample collection materials remain in view of the camera at all times. This would prevent a user from swabbing his or her nose and then switching out the swab with another that has been used by a different person. Additionally, it may be beneficial to positively identify the user during the collection process. This can be accomplished by, for example, checking the user's identity immediately before the sample collection process.

Figure 28:
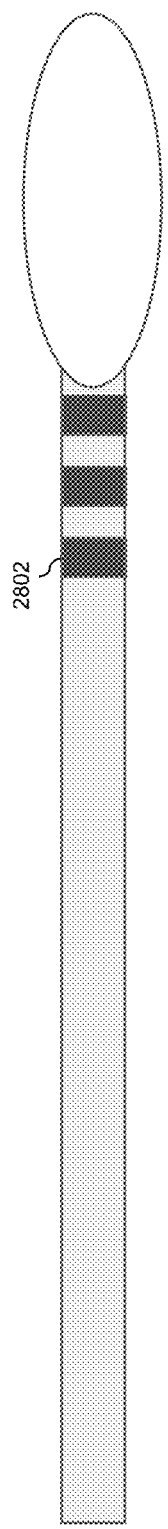
FIG. 28 illustrates an example of a swab that includes markings that can be used by a proctor or an automated system to ensure that testing procedures are followed.

During the test, it is also important to ensure that all test instructions and procedures are followed correctly. This can ensure the accuracy and validity of the test results. Similar to verifying that the sample is obtained from the correct user, ensuring that all test instructions and procedures are followed correctly can be accomplished by directly viewing the testing procedure, either over a live video feed or be watching a recording of the testing process. In some embodiments, such observation is provided by a live proctor. In some embodiments, such observation is provided through an automated system (e.g., a computer system that is configured analyze live or pre-recorded video). In the case of a swab, for example, as shown in FIG. 28, the swab can include stripes or other markings 2802 along its length to be able to quantify swab insertion depth in an orifice, such as a nostril. In this manner, a proctor can easily observe that the swab is inserted to a sufficient depth. Additionally, the automated system can be configured to recognize the stripes or markings 2802 on the swabs in the video to automate determination of proper insertion depth. In some embodiment, in which test a test must sit for a certain amount of time (e.g., dwell example), the user can be instructed to place the test on a suitable surface in view of the camera for an appropriate amount of time. The proctor or system can observe that the test is placed on the appropriate surface and remains in view during the entire dwell length. In the case of a nasal swab COVID-19 test, for example, an appropriate amount of liquid may need to be added to a testing card, a nasal swab may need to be inserted into the nostril to a sufficient depth, the swab must then be correctly applied to the liquid on the card, and the card must be left undisturbed on a flat surface for at least fifteen minutes. Each of these steps can be observed and verified by a proctor and/or an automated system to ensure the integrity of the test.

Additionally, it is important to ensure that submitted test results actually come from the originally verified test or test kit. This can ensure test continuity, making sure that the same test is used throughout the test (e.g., that the test that was verified is the one for which results are obtained). Otherwise, tests could be exchanged during the process, leading to improper results. In some embodiments, this can be accomplished by reverifying the test or test kit throughout the testing procedure. For example, the method that was used previously to determine the test kit was valid (e.g., scanning the unique ID of the test kit) can be repeated to ensure the UID/serial number are the same. In some embodiments, the test kits can be designed such that the test such that the results are reported in a manner that includes the UID/serial number, such as in a custom visible code (barcode, QR code, etc.) or NFC/RFID, so that when the results are read, the UID can be verified. For example, in some embodiments, test results are verified by viewing strips that appear on a test card. The test card can include the unique ID of the test kit near the area at which the strips will appear such that a view of the strips also includes a view of the unique ID.

Finally, it can also be important to ensure that the test results are interpreted correctly. As described previously, in some embodiments, a proctor interprets the test results by viewing strips that appear on a test card, for example, as described above with reference to FIG. 12. In some embodiments, an automated system may interpret the test results. In some embodiments, the test results can be reviewed and verified by another proctor or automated system to provide a second layer of verification.

Test Pass

A test pass can be provided and associated with the platform that is used to identify the user and communicate the user's test results. In some embodiments, the test pass can be provided at and/or used to verify a user's identity at a point of care, such as the location where the test is taken (e.g., a medical facility, a home, a hotel, an airport, a etc.), and also used to verify the user's test results at a point of verification (e.g., a location where the user's results are checked (such as the airport, a hotel, a place of employment, etc.). In some embodiments, the point of care and the point of verification may be different. For example, a user may take the test at his or her home and receive the test pass and then can use the test pass to verify his or her results at the airport. In some embodiments, the point of care and the point of verification may be the same. For example, a user desiring to board a flight at an airport can take a test and receive a test pass at the airport and then use that pass to verify the results and board a flight.

In some embodiments, the test pass can be configured to perform one or more of several functions. For example, the test pass can include proof of the user's identity. For example, in FIG. 5, the test pass includes personal information 502. The personal information can include the user's name and other identifying information such as photo or other biometric information. The test pass can be configured to show this information to prove the user's identity at a point of care (e.g., at medical facility or home at which the test is taken) and at point of verification (e.g., at an airport, stadium, etc., where the test result is checked). In some embodiments, the test pass includes a positive identifier that checks or verifies the user's identity against a driver's license, passport, or other verifiable biometric data. In preferred embodiments, identity verification using the test pass should be simple and quick. Additionally, the test pass should be configured such that the results reported by the pass should be able to be trusted at point of verification. For example, the test pass can ensure that results stored on the pass were gathered using an FDA-approved method. The test pass can also be configured for information security. For example, the test pass can provide the user with a mechanism for controlling who accesses their data and when.

A test pass can be provided in either a physical or virtual manner. For example, a physical test pass may comprise forgery-resistant card provided by the test pass issuer that includes user's name and photo for identification. The physical test pass may also include a barcode, QR code, NFC chip, contact chip, alphanumeric code, or other unique identifier that will access test results from a secure database when scanned. An example is shown in FIG. 5, described above. A virtual test pass may be available over a computer network or through an application. When accessed, it can display a scannable code or use NFC or other means for quick communication at point of verification. In some embodiments, the test pass can be linked to a user's existing ID. For example, test results can be linked to an existing form of ID by name and unique number (driver's license number, passport number, etc.). The user must have this ID at point of care and point of verification, where their name and unique number are used to access results from a secure database.

In some embodiments, each user is provided with a new physical or virtual test pass each time they complete a test. For example, a user may be provided with a new physical test pass indicating the most recent test result, or the user may be provided with a virtual test pass indicating the most recent test result. In other embodiments, in which the user already has a test pass, upon completion of a new test, the existing test pass can be updated to include the most recent result. For example, a machine-readable code on a physical or virtual test pass may be linked to the newest test result.

In some embodiments of a virtual test pass, the user's ID may be verified each time that the virtual test pass is displayed. For example, the user may be required to be biometrically authenticated each time the virtual test pass is to be displayed. As one example, the user may use face recognition on his or her phone in order to verify his or her identity before the virtual test pass can be displayed.

Test Continuity

As described above, the remote testing platform described herein can connect remotely located users with proctors over a network such as the internet. Problems may arise if either the users or the proctors experience poor network connectivity. The platform, however, may implement certain mechanisms and procedures to facilitate remote testing even in circumstances of poor network connectivity. For example, if either the proctor or the user experiences connectivity issues during the proctoring session, the proctoring session may be prematurely terminated, which can be inconvenient for users. However, the platform can be adapted to detect a loss of connection and/or poor connection, and take steps to record images or video of the user and test kit so that testing and proctoring can be resumed if and when connectivity is restored.

The platform may evaluate the strength of the user's network connection. In response to determining that the user's connection has dropped out or slowed down dramatically, the platform may perform one or more operations to begin recording and storing image or video data to a local location (e.g., on the user's hard drive). For example, the user may be participating in a live proctored testing session in which they are actively connected to a live proctor over video. During the session, the platform can monitor the user's network connection. If certain threshold criteria are met, indicating that the user's network connection is unstable or insufficient, the platform may initiate a recording of the user's session. In some embodiments, detection of a network connectivity issue may trigger high full frame rate resolution recording. In some embodiments, the recording is initiated and stored on the user's local machine, such that a network connection is not required for the recording. Depending on the type of test being performed and/or the level of proctor involvement necessary, the testing session may be able to continue, even though the user has lost his or her network connection to the proctor. For example, the user may be provided with prerecorded or written instructions for completing the testing session. Upon regaining connectivity, the recorded data may be uploaded to the platform and provided for proctor (or automated review). For example, once network connectivity is restored, the user's video may be uploaded to the platform where it can be reviewed by a proctor (or an automated system) to determine whether all testing steps were accurately followed. If all testing steps can be verified, the user's test result can also be verified. If one or more of the testing steps cannot be verified, the user may need to redo the test.

In addition to monitoring the user's network connection, the platform may also monitor the proctors' network connection. If a proctor's network connection is determined to be unstable or slow, the platform may perform one or more operations to ensure or facilitate test continuity for users connected to that proctor. For example, the platform may begin recording and storing user image or video data to cloud storage such that the proctor may review the image or video data when his or her network connection is restored. In some embodiments, detection of a network connectivity issue may trigger high full frame rate resolution recording. In some embodiments, the platform may send the recorded image or video data to another proctor or an automated system for review such that the user can continue the proctored testing session without delay. For example, the image or video data may be reviewed (in real-time) using an automated system or by another available proctor. When the original proctor regains network connectivity, in some embodiments, the proctor may be given access to the recorded data for review. In some embodiments, upon determining that a proctor's network connection is unstable, slow, or otherwise not working, one or more users connected to that proctor may be redirected to other proctors. In some embodiments, a backup proctor may be connected to the testing session such that the backup proctor can seamlessly take over in the event that the initial proctor becomes unavailable.

In the event of network connectivity issues (either on the user end or the proctor end), the platform may display messages to the user or the proctor indicating the potential issue and the steps being taken to ensure or facilitate testing continuity. For example, the user may be provided with a notification regarding the connectivity issues, instructions on how to proceed, and a phone number that can be used to contact customer support, etc.

Figure 29:
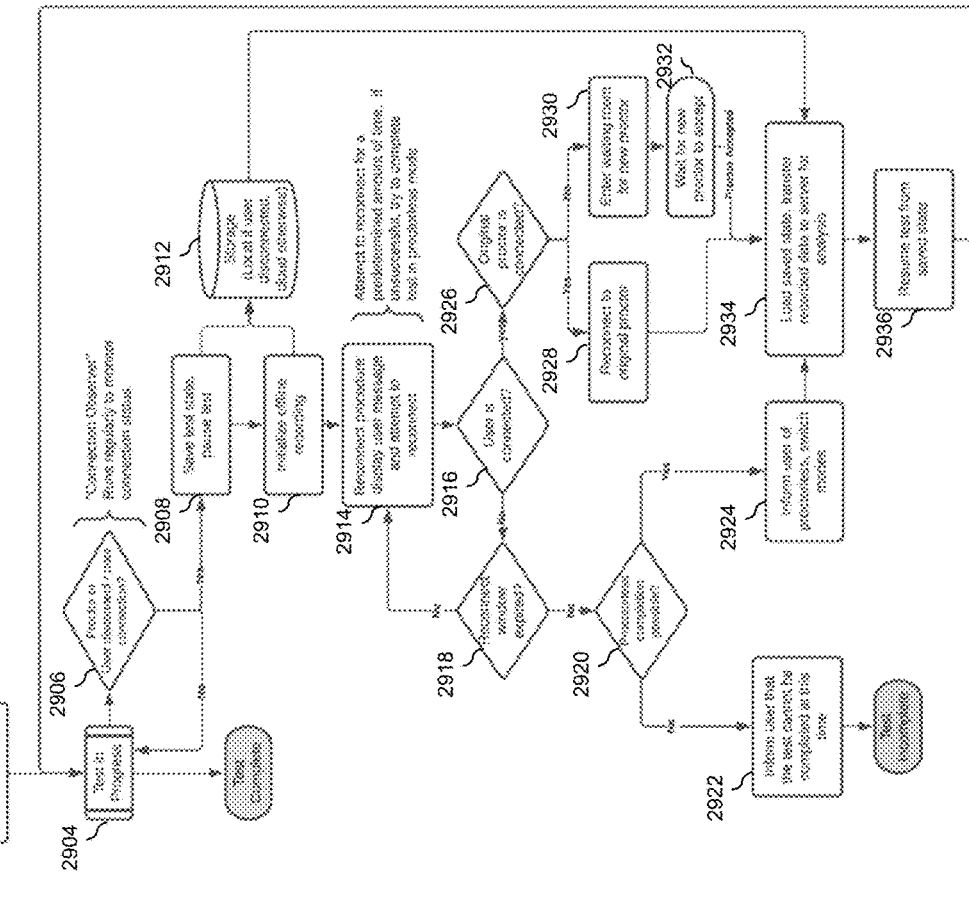
FIG. 29 illustrates an example flowchart for providing test continuity in the event of network connection problems according to some embodiments described herein.

FIG. 29 illustrates an example method for improving or maintaining test continuity in the case of network connection issues. When a user begins a test, the user may be asked at 2902 for their permission to record the testing session. In some embodiments, this may be a requirement for using the platform. At 2904, the proctored testing session begins. This can include establishing a live video link between the user and a proctor. At 2906, the platform monitors user's and the proctor's network connection. For example, a connection observer can run regularly to monitor the connection status. In the event that no network connectivity issues are detected, the testing session can be completed as normal. In the event that network connectivity issues are detected, at 2908, the platform may save the test state and/or pause the test. At 2910, a recording of the testing session may be initialized. At 2912, the recording and/or the test state can be stored. Storage can occur locally (e.g., on the user's machine) in the event that the user has lost network connectivity or storage can occur in the cloud if such storage medium is currently reachable.

At 2914, reconnect procedures may attempt to reestablish connectivity between the user and the platform. For example, the platform may attempt to reconnect the user for a predetermined amount of time (also referred to herein as the "reconnect window"). At 2916, if the user cannot be reconnected, the platform moves to 2918 at which the platform evaluates whether the reconnect window has expired. If it has not, the platform moves back to 2914. If the reconnect window has expired, the platform moves to 2920, at which it determines whether proctorless completion of the test is possible. Proctorless completion may be possible in some circumstances depending on the type of test and/or the stage of the test at which connectivity was lost. If proctorless completion is not possible, the user may be informed at 2922 that the test cannot be completed. The user will need to retest or resume the test once network connectivity is reestablished. If proctorless testing is possible, the user may be informed of the switch to proctorless mode at 2924. At 2934, the saved test state and/or recorded video can be loaded from the server and analyzed. At 2936, the test can be resumed from the saved state and completed in proctorless mode.

Returning to 2916, if the platform determines that the user is connected, the platform may, at 2926, determine whether the original proctor is connected. If the original proctor is connected, the user and proctor can be reconnected and testing can resume as normal. If the original proctor is not connected, at 2930, the user may enter a waiting room where a new proctor can be assigned. At 2932, the new proctor can accept the request and the test can be resumed with the new proctor.

Augmented Reality (AR) Based Testing Guidance

In some embodiments, the platform may provide augmented reality (AR) based testing guidance to users and/or proctors. Because users and proctors generally interact with the platform using devices that include displays, AR-based testing guidance can be overlaid onto the displays to facilitate testing and/or proctoring. For example, graphics can be overlaid onto a live video feed of the test kit (as provided by a camera of the user's device) to help the user properly open, set up, utilize, and/or dispose of the test kit. As a more specific example, in some tests, the user may be required to deposit drops of a solution onto a certain portion of a test card (see, for example, FIG. 30C, described below). The user can be instructed to position the test kit such that it is within the view of the camera and can be viewed on the user's screen. Guidance indicating where to deposit the drops can be overlaid onto the user's screen to indicate where the user should place the drops of solution. As another example, when the user needs to access a swab within the test kit, the location of the swab can be highlighted using AR on the user's screen.

Figure 30A:
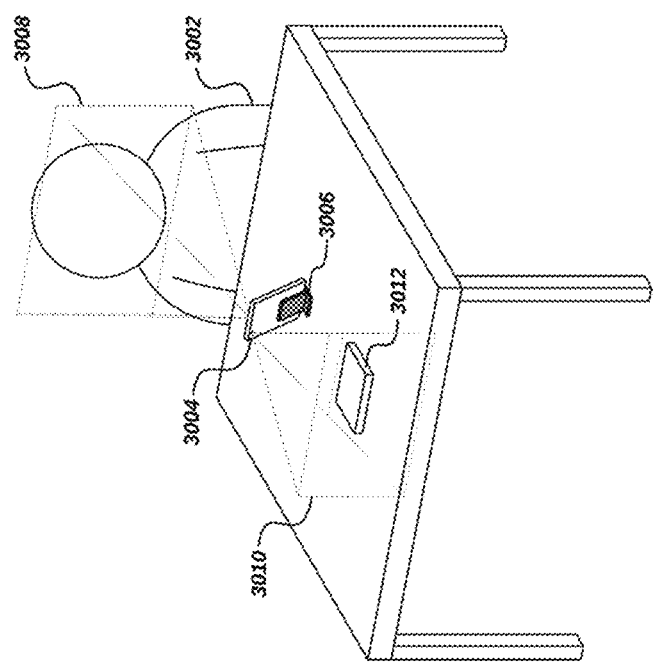
FIG. 30A illustrates a user taking a remote health or diagnostic test using a test kit and a user device, such as a mobile phone, according to some embodiments as described herein.

AR-based guidance can be implemented in a variety of different ways. FIG. 30A illustrates an example set up for providing AR-based guidance. In the illustrated example, a user 3002 accesses the health testing and diagnostic platform using a smartphone 3004. In this example, the smartphone 3004 includes both forward facing and rearward facing cameras. One or both of these cameras can be used during a testing procedure to capture images of, for example, the user 3002 and/or a test kit 3012 used during the testing procedure. Further, the images captured by the forward and/or rearward facing cameras can be displayed to the user on a display of the smartphone 3004. Moreover, AR-based guidance can be added to the images displayed to the user to facilitate and improve the testing experience. Examples of AR-based guidance that can be displayed to the user are shown in FIGS. 30C and 30E, described below.

FIG. 30A also illustrates an example set up of the user 3002, the smartphone 3004, and the test kit 3012, which may be advantageous in some embodiments. In the illustrated example, the user 3002 sits at a table. The test kit 3012 is also positioned on the table in front of the user. The user's smartphone 3004 is positioned on the table between the user 3002 and the test kit 3012. In some embodiments, the smartphone 3004 is supported by a stand 3006, which can, for example, be a component included in the test kit 3012. The smartphone 3004 is positioned (in some embodiments, with the assistance of the stand 3006) such that the user is visible within the field of view (FOV) 3008 of the smartphone's forward-facing camera and the test kit 3012 is positioned within the FOV 3010 of the smartphone's rearward facing camera. Such a set up may be advantageous as it allows the user 3002 and the test kit 3012 to remain within the different FOVs of the forward and rearward facing cameras of the smartphone 3002 during the entire testing procedure. Further, at different portions of the procedure, the output of the frontward or rearward facing camera can be displayed to the user and supplemented with AR-based guidance.

For example, during one portion of the testing procedure, the output of the rearward facing camera (e.g., FOV 3010 in which is positioned the test kit 3012) can be displayed to the user such that the user can view the test kit 3012 on the display of the smartphone 3004. The display can be updated with AR-based guidance to highlight certain areas of the test kit 3012 or items in the test kit 3012 or overlaid with other types of instructions to aid the user in performing the testing procedure. During another portion of the testing procedure, the output of the frontward facing camera (e.g., FOV 3008 in which the user 3002 is positioned) can be displayed to the user such that the user can view his or herself on the display of the smartphone 3004. The display can be updated with AR-based guidance to highlight certain areas of the user (e.g., a nostril) or overlaid with other types of instructions to aid the user in performing the testing procedure.

In some embodiments, the set up illustrated in FIG. 30A and/or use of the stand 3006 can facilitate setting up standard distances between the user 3002, the user device 3004, and the test kit 3012. In some embodiments, the system may benefit from knowing the distances between user 3002, the user device 3004, and the test kit 3012. For example, knowing these distances may allow the system to more easily identify certain elements within the field of view(s) 3008, 3012 of the cameras and/or ensure that all steps that must be observed are accurately captured on the camera. In some embodiments, the stand 3006 can be integrated into the test kit box. For example, a portion of the test kit box can fold out to provide the stand and fix the distance between the test kit and the user device.

Figure 30B:
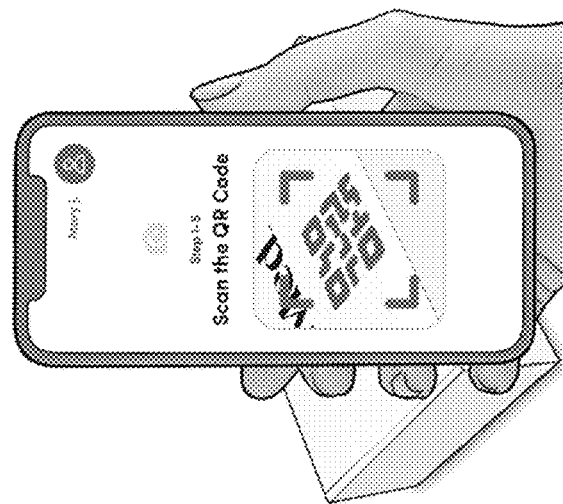
FIG. 30B illustrates a user scanning a QR code included on a test kit using a user device, such as a mobile phone, according to some embodiments as described herein.
Figure 30C:
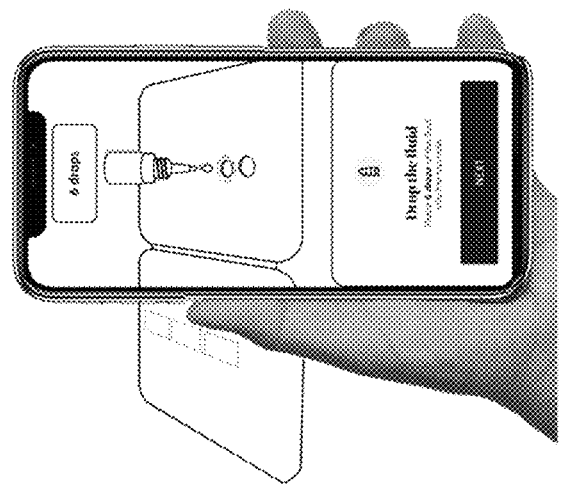
FIG. 30C illustrates an example of augmented reality (AR) based guidance that can be displayed on a user device, such as a mobile phone, wherein AR is used to illustrate a location on a test card to which drops should be applied as part of a remote health testing process, according to some embodiments as described herein.

FIG. 30B illustrates an example in which a user scans a QR code printed on an exterior of a test kit containing test kit materials. In some embodiments, one or more AR features associated with such test kit materials may be provided in response to the system scanning the QR code. For instance, text and/or graphics relating to the test kit materials contained within the box on which the QR code is printed may be overlaid onto the user's screen so as to convey one or more of the following: (i) information about each component stored in the box (e.g., labeling and/or highlighting various components, displaying text or graphics beside various components, etc.); and/or (ii) information regarding the steps that are to be taken by the user in order to take a test using test kit materials contained within the box (e.g., graphical and/or textual instructions presented in a manner that conveys an order of operations, etc.). Other types of information can also be communicated to the user using AR. Although FIG. 30B illustrates a QR code printed on the test kit box, in some embodiments, the QR code that is scanned may be printed on one or more of the test kit materials (rather than the box). In some embodiments, other types of machine-readable codes (e.g., bar codes, etc.) can be used in addition to or in place of the illustrated QR codes. In some embodiments, one or more computer vision techniques may be leveraged to identify test kit materials and packaging instead of or in addition to the aforementioned QR code scanning techniques.

Figure 30D:
FIG. 30D illustrates another example of augmented reality (AR) based guidance that can be displayed on a user device, such as a mobile phone, wherein AR is used to illustrate a nose swab procedure as part of a remote health testing process, according to some embodiments as described herein.
Figure 30E:
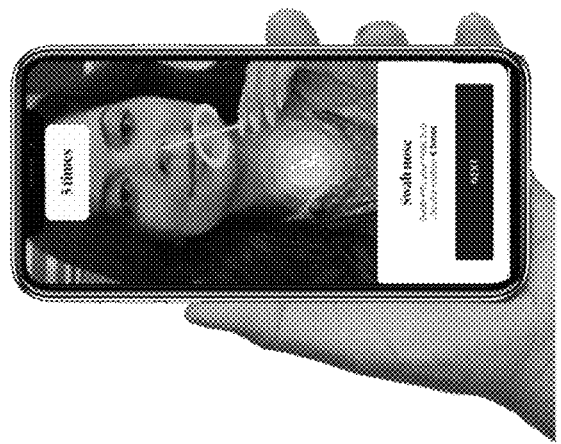
FIG. 30E illustrates another example of augmented reality (AR) based guidance that can be displayed on a user device, such as a mobile phone, wherein AR is used to illustrate further steps in a nose swab procedure as part of a remote health testing process, according to some embodiments as described herein.

FIGS. 30C-30E illustrate several examples of AR-based guidance that can be displayed to a user to facilitate a remote testing procedure. The illustrated examples are not exhaustive, and AR-based guidance can be used in many other ways as well. In the example of FIG. 30C, the AR graphics that are overlaid on the screen include a dropper bottle, drops of solution dripping from the dropper bottle, and a dashed circle outlining the location where drops are to be applied. Such AR-based guidance can be used to illustrate to the user the location on a test card to which a solution should be applied during a testing procedure. In FIG. 30C, textual instructions (e.g., "6 drops," "Drop the fluid," etc.) are also overlaid on the screen.

In some embodiments, AR-based guidance may facilitate sample collection. For example, graphics can be overlaid onto a live video feed of the user (as provided by a camera of the user's device) to help the user properly collect the required biological sample from their person. FIGS. 30D and 30E provide examples illustrating AR-based guidance for sample collection using a nasal swab. In the example of FIG. 30D, the AR graphics that are overlaid on the screen include a dashed circle outlining the particular nostril of the user into which a swab is to be inserted. In FIG. 30D, textual instructions (e.g., "5 times," "Swab nose," etc.) are also overlaid on the screen. In the example of FIG. 30E, the AR graphics that are overlaid on the screen include a curved arrow indicating the direction in which the user is supposed to swab their nostril in a circular motion. In FIG. 30E, textual instructions (e.g., "5 times," "Swab nose," etc.) are also overlaid on the screen.

In the case of sample collection via a nasal swab, for example, as illustrated in FIGS. 30D and 30E, images of the user's face can be augmented with graphics to show the user which nostril to insert the swab (FIG. 30D), the types of movements required to properly collect the mucus sample from the nostril (FIG. 30E), the depth to insert swab, etc. Although the figures have illustrated examples of AR-based guidance in cases where the user device comprises a smartphone, AR-based guidance can also be provided for other types of user device. For example, in the case of a laptop, the aforementioned camera might be a camera on the laptop located above the screen. In the case of a smartphone, the aforementioned camera might be an inward-facing camera on the front of the smartphone above the screen. Accordingly, in some smartphone embodiments (or other embodiments where the user device includes both forward- and rearward-facing cameras) some steps may be performed using the forward-facing camera and some steps can be performed using the rearward-facing camera. The display shown to the user (e.g., on the screen on the front of the device) can change from the forward- to the rearward-facing camera depending on the step being performed. In some embodiments, the change of cameras occurs automatically.

In some examples, the user may place the smartphone in a smartphone stand, and may be instructed to position the test kit in front of the smartphone such that both the user and the test kit are visible in the inward-facing camera on the front of the smartphone above the screen, for example, as described above with respect to FIG. 30A. With continued reference to examples where the user accesses the platform using a smartphone, the user may be instructed to seat themselves at a table (with a flat surface), place the test kit on the table about 1.5 to 2 feet from the edge of the table, place their smartphone 3004 in a smartphone stand 3006 (e.g., that is included in the test kit), and position the smartphone 3004 in the smartphone stand 3006 on the table between themselves and the test kit 3002 such that their face and upper body is within the field of view of the smartphone's inward-facing camera and the test kit is within the field of the smartphone's outward-facing camera. Depending on whether the user is being given test kit guidance or sample collection guidance, the live video feed that's displayed for the user and overlaid with graphics may switch between the outward- and inward-facing cameras.

Artificial Intelligence (AI) Techniques for Proctor Assistance

In some embodiments, the platform may be configured to use proctor-generated data to train an artificial intelligence (AI) system (e.g., a neural network) to facilitate review of test results. For example, for each test performed using a live proctor, an image of the physical test (e.g., as captured by the camera on the user's device upon completion of the test and presented to the proctor for interpretation) can be stored in association with the test result as interpreted by the proctor. For example, proctor-classified positive and negative test result images can be stored. These stored images and the corresponding proctor-determined test results can be used as data for training one or more neural networks to provide accurate test result interpretations. For example, a single neural network could be trained using data captured and generated during proctoring sessions overseen by many different proctors. Alternatively or additionally, a neural network could be trained using data captured and generated during proctoring sessions overseen by one specific proctor. Training of the neural network could be conducted in a training phase, on an ongoing basis, or a combination thereof. In this way, as the platform generates data using live proctors, the data set for training the neural network can grow, increasing the accuracy with which the neural network can analyze the test results.

Once the neural network is sufficiently trained, the neural network can, in some implementations, be used to analyze the test results. In some embodiments, the neural network can be used as a supplement to the proctors' interpretations of the test results. For example, an AI-assisted test result interpretation can be provided to help the proctors analyze the test results. A machine learning model (e.g., the neural network trained in the aforementioned manner) can be used to provide proctors with recommended suggested test result interpretations in real-time based on images of physical tests (as captured upon test completion and presented to proctors for interpretation). The proctors may then be given the option to agree or disagree with each recommendation. This may facilitate faster test interpretation by the proctor and/or generate additional data that could be used to continually train the neural network.

Figure 31:
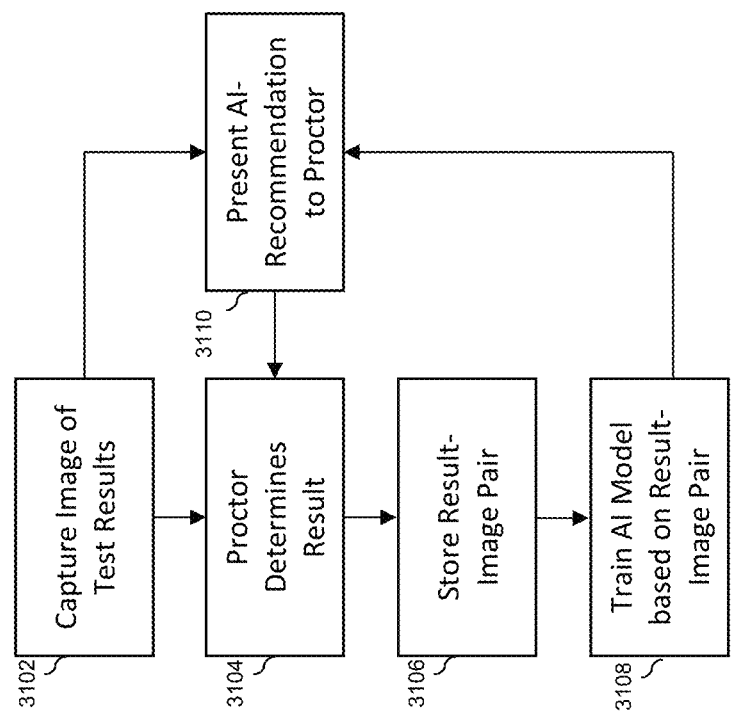
FIG. 31 illustrates an example flowchart for training an artificial intelligence (AI) or machine learning (ML) system to interpret test results according to some embodiments as described herein.

FIG. 31 is a flowchart illustrating an example method for training an artificial intelligence or machine learning system to interpret test results according to one embodiment. At 3102, images of test results can be captured. For example, such images can be taken during a proctored video session. In some embodiments, the images are still images taken from a recording of the proctored video session. In some embodiments, the images comprise video of the test results. At 3104, during a proctored testing session, the proctor can view the test results and make a determination as to whether the results are positive or negative. At 3106, the image of the test result (from 3102) and the determination made by the proctor (at 3104) are stored as a result-image pair. At 3108, result-image pairs can be used to train an AI or machine learning model (such as the neural network described above).

Once the AI model has been trained, the model may, at 3110, present AI-determined recommendations to the proctors during proctored test sessions. For example, during a proctored test session an image of the test results can be captured and displayed to the proctor. The image can also be transmitted to the AI model, which can make a determination as to the result. The AI-determined result can be presented to the proctor as a recommendation. The proctor may make the final determination of the result based on the image of the test results as well as the AI-determined result. When the proctor determines the result, the result-image pair may be stored and used to further refine the training of the AI model.

Computer Systems

Figure 32:
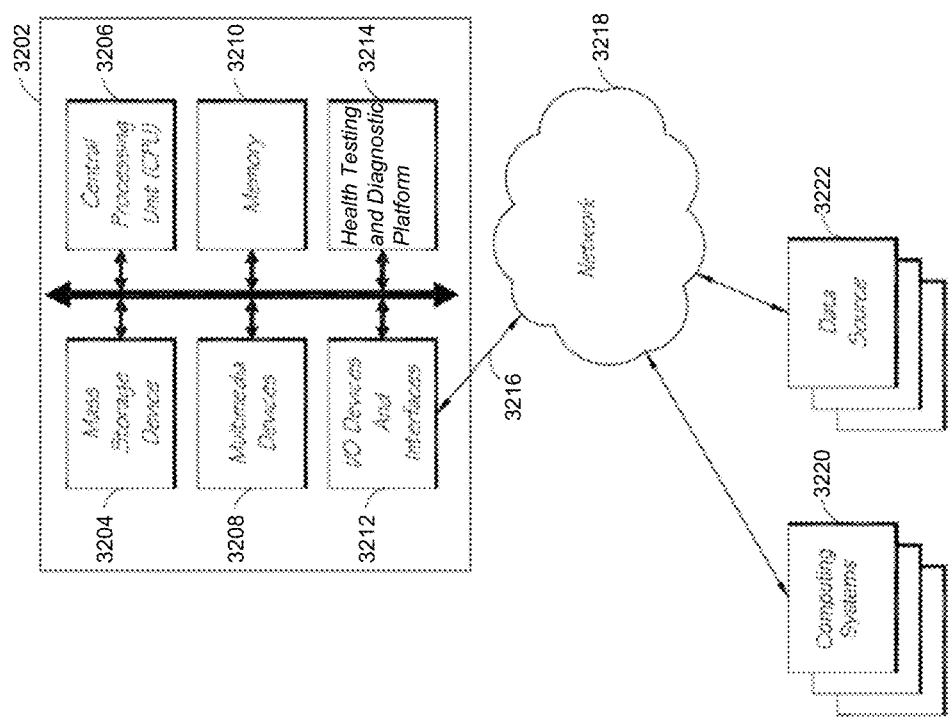
FIG. 32 is a block diagram illustrating an example embodiment of a computer system configured to run software for implementing one or more embodiments of the health testing and diagnostics systems, methods, and devices disclosed herein.

FIG. 32 is a block diagram depicting an embodiment of a computer hardware system configured to run software for implementing one or more embodiments of the health testing and diagnostic systems, methods, and devices disclosed herein.

In some embodiments, the systems, processes, and methods described herein are implemented using a computing system, such as the one illustrated in FIG. 32. The example computer system 3202 is in communication with one or more computing systems 3220 and/or one or more data sources 3222 via one or more networks 3218. While FIG. 32 illustrates an embodiment of a computing system 3202, it is recognized that the functionality provided for in the components and modules of computer system 3202 may be combined into fewer components and modules, or further separated into additional components and modules.

The computer system 3202 can comprise a health testing and diagnostic module 3214 that carries out the functions, methods, acts, and/or processes described herein. The health testing and diagnostic module 3214 is executed on the computer system 3202 by a central processing unit 3206 discussed further below.

In general, the word "module," as used herein, refers to logic embodied in hardware or firmware or to a collection of software instructions, having entry and exit points. Modules are written in a program language, such as JAVA, C or C++, PYPHON or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems and may be stored on or within any suitable computer readable medium or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 3202 includes one or more processing units (CPU) 3206, which may comprise a microprocessor. The computer system 3202 further includes a physical memory 3210, such as random access memory (RAM) for temporary storage of information, a read only memory (ROM) for permanent storage of information, and a mass storage device 3204, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of the computer system 3202 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 3202 includes one or more input/output (I/O) devices and interfaces 3212, such as a keyboard, mouse, touch pad, and printer. The I/O devices and interfaces 3212 can include one or more display devices, such as a monitor, that allows the visual presentation of data to a user. More particularly, a display device provides for the presentation of GUIs as application software data, and multi-media presentations, for example. The I/O devices and interfaces 3212 can also provide a communications interface to various external devices. The computer system 3202 may comprise one or more multi-media devices 3208, such as speakers, video cards, graphics accelerators, and microphones, for example.

The computer system 3202 may run on a variety of computing devices, such as a server, a Windows server, a Structure Query Language server, a Unix Server, a personal computer, a laptop computer, and so forth. In other embodiments, the computer system 3202 may run on a cluster computer system, a mainframe computer system and/or other computing system suitable for controlling and/or communicating with large databases, performing high volume transaction processing, and generating reports from large databases. The computing system 3202 is generally controlled and coordinated by an operating system software, such as z/OS, Windows, Linux, UNIX, BSD, SunOS, Solaris, MacOS, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 3202 illustrated in FIG. 32 is coupled to a network 3218, such as a LAN, WAN, or the Internet via a communication link 3216 (wired, wireless, or a combination thereof). Network 3218 communicates with various computing devices and/or other electronic devices. Network 3218 is communicating with one or more computing systems 3220 and one or more data sources 3222. The health testing and diagnostic module 3214 may access or may be accessed by computing systems 3220 and/or data sources 3222 through a web-enabled user access point. Connections may be a direct physical connection, a virtual connection, and other connection type. The web-enabled user access point may comprise a browser module that uses text, graphics, audio, video, and other media to present data and to allow interaction with data via the network 3218.

Access to the health testing and diagnostic module 3214 of the computer system 3202 by computing systems 3220 and/or by data sources 3222 may be through a web-enabled user access point such as the computing systems' 3220 or data source's 3222 personal computer, cellular phone, smartphone, laptop, tablet computer, e-reader device, audio player, or another device capable of connecting to the network 3218. Such a device may have a browser module that is implemented as a module that uses text, graphics, audio, video, and other media to present data and to allow interaction with data via the network 3218.

The output module may be implemented as a combination of an all-points addressable display such as a cathode ray tube (CRT), a liquid crystal display (LCD), a plasma display, or other types and/or combinations of displays. The output module may be implemented to communicate with input devices 3212 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition, a touch screen may act as a hybrid input/output device. In another embodiment, a user may interact with the system more directly such as through a system terminal connected to the score generator without communications over the Internet, a WAN, or LAN, or similar network.

In some embodiments, the system 3202 may comprise a physical or logical connection established between a remote microprocessor and a mainframe host computer for the express purpose of uploading, downloading, or viewing interactive data and databases on-line in real time. The remote microprocessor may be operated by an entity operating the computer system 3202, including the client server systems or the main server system, an/or may be operated by one or more of the data sources 3222 and/or one or more of the computing systems 3220. In some embodiments, terminal emulation software may be used on the microprocessor for participating in the micro-mainframe link.

In some embodiments, computing systems 3220 who are internal to an entity operating the computer system 3202 may access the health testing and diagnostic module 3214 internally as an application or process run by the CPU 3206.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

The computing system 3202 may include one or more internal and/or external data sources (for example, data sources 3222). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 3202 may also access one or more databases 3222. The databases 3222 may be stored in a database or data repository. The computer system 3202 may access the one or more databases 3222 through a network 3218 or may directly access the database or data repository through I/O devices and interfaces 3212. The data repository storing the one or more databases 3222 may reside within the computer system 3202.

Figure 33:
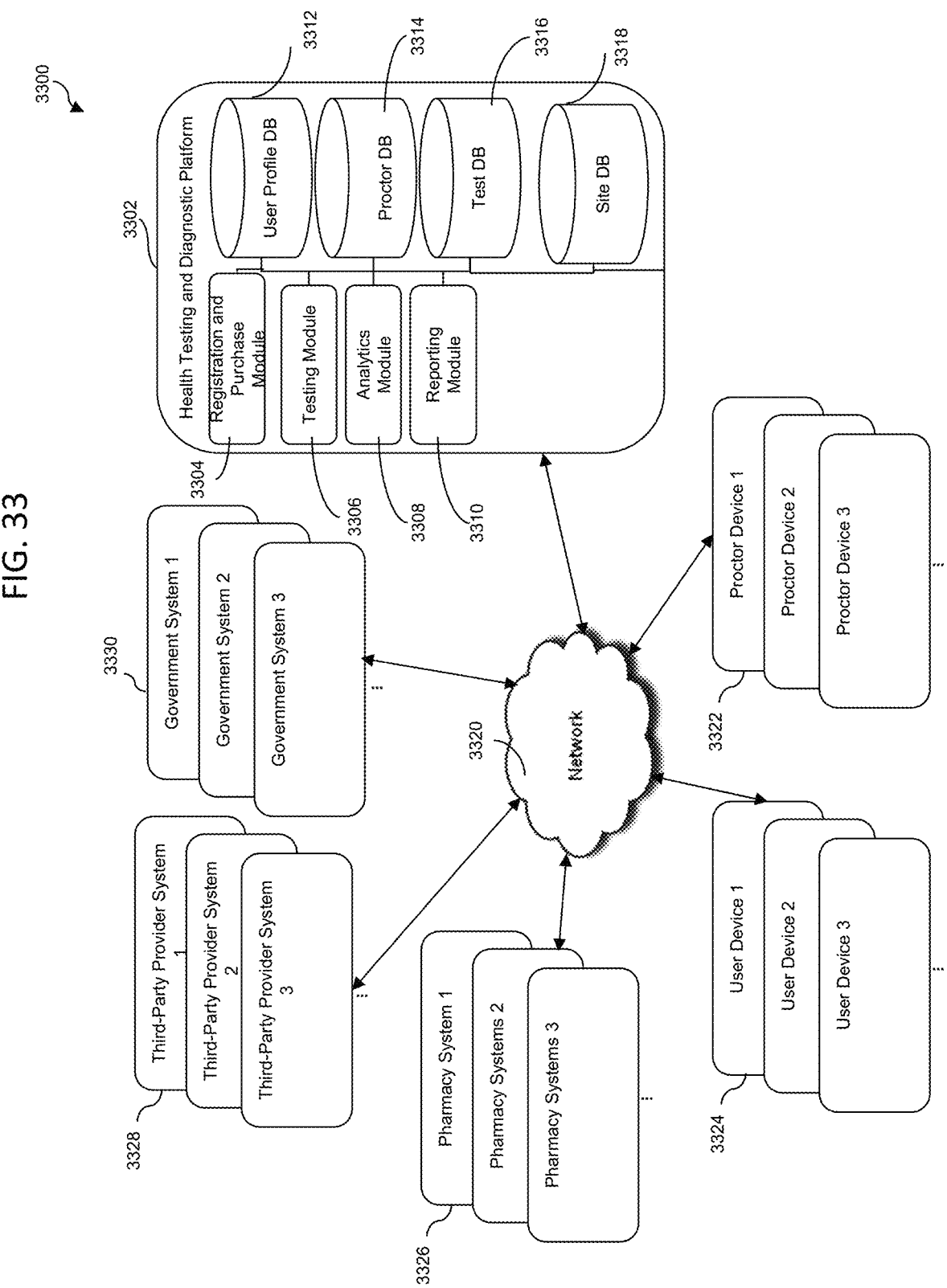
FIG. 33 illustrates another example embodiment of a computer system configured to run software for implementing one or more embodiments of the health testing and diagnostics systems, methods, and devices disclosed herein.

FIG. 33 is a block diagram illustrating an example embodiment of a computer system configured to run software for implementing one or more embodiments of the health testing and diagnostic systems, methods, and devices disclosed herein. In some embodiments, the various systems, methods, and devices described herein may also be implemented in decentralized systems such as, for example, blockchain applications. For example, blockchain technology may be used to maintain user profiles, proctor profiles, test results, test site databases, and/or financing databases or ledgers, dynamically generate, execute, and record testing plan agreements, perform searches, conduct patient-proctor matching, determine pricing, and conduct any other functionalities described herein.

In some embodiments, a health testing and diagnostic platform 3302 may be comprised of a registration and purchase module 3304, a testing module 3306, an analytics module 3308, and a reporting module 3310. The health testing and diagnostic platform 3302 may also comprise a user profile database 3312, a proctor database 3314, a test database 3316, and/or a site database 3318. The health testing and diagnostic platform 2002 can be connected to a network 3320. The network 3320 can be configured to connect the health testing and diagnostic platform 3302 to one or more proctor devices 3322, one or more user devices 3324, one or more pharmacy systems 3326, one or more third-party provider systems 3328, and/or one or more government systems 3330.

The registration and purchase 3304 may function by facilitating patient registration through one or more registration interfaces and in conjunction with the user database 3312, store user registration data. The testing module 3306 may be configured to allow a user to initiate and complete a medical test or visit with a proctor through a series of pre-testing and testing interfaces, as described herein. The analytics module 3308 may be configured to dynamically analyze patient tests across a given population stored in the test database 3316 and provide structured data of the test results. The reporting module 3310 may function by dynamically and automatically reporting test results to government entities, patients, and third parties using one or more interfaces, such as one or more application programming interfaces. Each of the modules can be configured to interact with each other and the databases discussed herein.

ADDITIONAL EMBODIMENTS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense.

Indeed, although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and subcombinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every embodiment.

It will also be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present. The headings provided herein, if any, are for convenience only and do not necessarily affect the scope or meaning of the devices and methods disclosed herein.

Accordingly, the claims are not intended to be limited to the embodiments shown herein, but are to be accorded the widest scope consistent with this disclosure, the principles and the novel features disclosed herein.

What is claimed is:

1. A computer-implemented system for a multi-session proctored examination platform, the computer-implemented system comprising:
    an electronic storage medium comprising computer-executable instructions; and
    one or more processors configured to execute the computer-executable instructions to:
        cause a graphical user interface (GUI) to be displayed on a display of a proctor device, the GUI configured to display to a proctor a graphical representation indicating a plurality of phases associated with a testing protocol for medical diagnostic testing;
        establish a plurality of electronic video conference sessions between the proctor device and a plurality of user computing devices, each of the user computing devices associated with a user of a plurality of users undergoing medical diagnostic testing; and
        for at least one of the plurality of electronic video conference sessions, cause a live video feed of a user to be displayed on the GUI on the proctor device relative to the graphical representation indicating the plurality of phases of the medical diagnostic test to indicate a current phase of the user;
        wherein a position of the live video feed relative to the graphical representation changes location upon completion of each testing phase, such that the GUI is automatically and dynamically updated.

2. The computer-implemented system of claim 1, wherein the one or more processors are further configured to cause content data to be displayed on the plurality of user devices, wherein the content data comprises augmented reality content data for showing each of the plurality of users how to administer the medical diagnostic test.

3. The computer-implemented system of claim 1, wherein the one or more processors are further configured to cause content data to be displayed on the plurality of user devices, wherein the content data comprises virtual reality content data for showing the plurality of users how to administer the medical diagnostic test.

4. The computer-implemented system of claim 2, wherein the proctor can simultaneously conduct each of the plurality of video conference sessions with the plurality of users while monitoring the plurality of users that are viewing the content data.

5. The computer-implemented system of claim 4, wherein the monitoring the plurality of users that are viewing the content data comprises transmitting to the proctor device video data of each of the plurality of users to ensure that the plurality of users are watching the content data.

6. The computer-implemented system of claim 5, wherein the one or more processors are further configured to:
    analyze, based on a computer vision algorithm, the video data to detect a medical diagnostic test device and to determine if the medical diagnostic test device has moved; and
    transmit, based on determining that the medical diagnostic test device has moved, an alert notification to the proctor device to notify the proctor that the medical diagnostic test device has moved.

7. The computer-implemented system of claim 5, wherein the one or more processors are further configured to receive:
    a mute request from the proctor device to mute the proctor for at least one of the plurality of electronic video conference sessions, and
    an unmute request from the proctor device to unmute the proctor associated with the video data being transmitted to at least one of the plurality of users.

8. The computer-implemented system of claim 1, wherein the current phase of each of the plurality of users are different phases.

9. The computer-implemented system of claim 1, wherein the computing system comprises one or more computing systems.

10. The computer-implemented system of claim 1, wherein the one or more processors are further configured to:
    receive a selection of one of the plurality of users, wherein the selection is made by the proctor through the GUI displayed on the proctor device;
    generate content data based on the selection of one of the plurality of users; and
    cause the content data to by displayed on the GUI on the proctor device.

11. The computer-implemented system of claim 1, wherein the one or more processors are further configured to:
    receive a selection of one of the plurality of users, wherein the selection is made by the proctor through the GUI displayed on the proctor device;
    establish an audio channel between the proctor device and the user computing device of the selection of one of the plurality of users; and
    terminate any other audio channel between the proctor device and any other user computing device.

12. A computer-implemented method for a multi-session proctored examination platform, the computer-implemented method comprising:
    causing, by a computer system, a graphical user interface (GUI) to be displayed on a display of a proctor device, the GUI configured to display to a proctor a graphical representation indicating a plurality of phases associated with a testing protocol for medical diagnostic testing;
    establishing, by the computer system, a plurality of electronic video conference sessions between the proctor device and a plurality of user computing devices, each of the user computing devices associated with a user of a plurality of users undergoing medical diagnostic testing; and
    for at least one of the plurality of electronic video conference sessions, causing, by the computer system, a live video feed of a user to be displayed on the GUI on the proctor device relative to the graphical representation indicating the plurality of phases of the medical diagnostic test to indicate a current phase of the user, wherein a position of the live video feed relative to the graphical representation changes location upon completion of each testing phase, such that the GUI is automatically and dynamically updated;
    wherein the computer system comprises a computer processor and an electronic storage medium.

13. The computer-implemented method of claim 12, further comprising causing content data to be displayed on the plurality of user devices, wherein the content data comprises augmented reality content data for showing each of the plurality of users how to administer the medical diagnostic test.

14. The computer-implemented method of claim 12, further comprising causing content data to be displayed on the plurality of user devices, wherein the content data comprises virtual reality content data for showing the plurality of users how to administer the medical diagnostic test.

15. The computer-implemented method of claim 14, wherein the proctor can simultaneously conduct each of the plurality of video conference sessions with the plurality of users while monitoring the plurality of users that are viewing the content data.

16. The computer-implemented method of claim 15, wherein the monitoring the plurality of users that are viewing the content data comprises transmitting to the proctor device video data of each of the plurality of users to ensure that the plurality of users are watching the content data.

17. The computer-implemented method of claim 16, further comprising:
  analyzing, based on a computer vision algorithm, the video data to detect a medical diagnostic test device and to determine if the medical diagnostic test device has moved; and
  transmitting, based on determining that the medical diagnostic test device has moved, an alert notification to the proctor device to notify the proctor that the medical diagnostic test device has moved.

18. The computer-implemented method of claim 12, wherein the current phase of each of the plurality of users are different phases.

19. The computer-implemented method of claim 12, further comprising:
  receiving a selection of one of the plurality of users, wherein the selection is made by the proctor through the GUI displayed on the proctor device;
  generating content data based on the selection of one of the plurality of users; and
  causing the content data to by displayed on the GUI on the proctor device.

20. The computer-implemented method of claim 12, further comprising:
  receiving a selection of one of the plurality of users, wherein the selection is made by the proctor through the GUI displayed on the proctor device;
  establishing an audio channel between the proctor device and the user computing device of the selection of one of the plurality of users; and
  terminating any other audio channel between the proctor device and any other user computing device.

* * * * *